US005474914A

United States Patent [19]

Spaete

[11] Patent Number: 5,474,914

[45] Date of Patent: Dec. 12, 1995

[54] METHOD OF PRODUCING SECRETED CMV GLYCOPROTEIN H

[75] Inventor: Richard Spaete, Belmont, Calif.

[73] Assignee: Chiron Corporation, Emeryville, Calif.

[21] Appl. No.: 921,807

[22] Filed: Jul. 29, 1992

[51] Int. Cl.$^6$ .......................... C12N 15/00; C12P 21/02; C07K 14/00

[52] U.S. Cl. .................. 435/69.1; 435/240.1; 435/252.3; 435/254.1; 435/320.1.69.7; 530/350

[58] Field of Search ............................... 435/69.1, 240.2, 435/320.1, 252.3, 254.11; 536/23.1; 530/395, 350

[56] References Cited

PUBLICATIONS

Buonocore and Rose, *Nature* (1990) 345:625–628.
Gompels and Minson, *J. Virol.* (1989) 63:4744–4755.
Haffar et al., *J. Virol.* (1990) 64:3100–3103.
Hutchinson et al., *J. Virol.* (1992) 66:2240–2250.
Hutchinson et al., Abstract, XVI International Herpes Virus Workshop, Jul. 7–12, 1991.
Kiefer et al., *Growth Factors* (1991) 5:115–127.
Pachl et al., *Virology* (1989) 169: 418–426.
Pancake et al., *J. Virol.* (1983) 47:568–585.
Sambrook and Gething, *Nature* (1989) 342: 224–225.
Spaete et al., *Progress in Cytomegalovirus Research* (M. P. Landini, ed., 1991, pp. 133–136).
Weber, *Nature (1990)* 345: 573–574; and.
WuDunn and Spear, *J. Virol.* (1988) 63:52–58.

*Primary Examiner*—Garnette D. Draper
*Assistant Examiner*—Sally P. Teng
*Attorney, Agent, or Firm*—Barbara G. McClung; Roberta L. Robins; Robert P. Blackburn

[57] ABSTRACT

Methods for the recombinant expression and secretion of viral proteins are disclosed. The methods involve the use of compatible escorts to shuttle the proteins to the cell surface. In this way, egress of recombinantly produced proteins out of the cell is facilitated, resulting in increased yields and easier purification of the desired protein.

6 Claims, 15 Drawing Sheets

```
CTGCAGGCTG TGGGTGGCGT GCCACCGCAC GGACTGATCG TCGGCGTCTG AGTACGTAGT    60

TTTGAACTCA ATCACGTAGC AATACACGAT GCCGCGCGAC CCAGAGTCCG GCGGTAAAAA   120

CACCAACACG CAGTCGGGAA TCCGCCGACT TAATCGTACT TCGATGAAAA GACGGCGACG   180

GTACTTTTGC AACTCGGGTG GGAAAAGGCC TCCCAACAGG CGGTTGAGCG CCACAAATGA   240

GGGAAAGACC CGCAGCAGGC GACGGTAGAT GTCCAGGTGC TTGCGCTTAC CGATCCGCTT   300

ACGCACGTGA GGCAATCTCC GCAGAGCGTT CCCCTTCGAA TCAGCGTCGT CCCCACACCC   360

GGACGGCATG ACTTACTCGC GTGTCCCCTC TTCTCCCTTC GCAGCGGCCA ATGACATCGT   420

ATTAAATAGA CGGAGACGCG ACTTTTGTAA CCCGTAGCGC CGCACCCGGG TGCTCCTTCC   480

TGGGATCCTT TCTCTCCTTC TCTCGGGTGT AACGCCAACC ACCACCTGGA TCACGCCGCT   540

                              Met Arg Pro Gly Leu Pro Ser Tyr Leu
GAACCCAGCG GCGCGGCCGC GCT     ATG CGG CCA GGC CTC CCC TCC TAC CTC   590

Ile Val Leu Ala Val Cys Leu Leu Ser His Leu Leu Ser Ser Arg Tyr
ATC GTC CTC GCC GTC TGT CTC CTC AGC CAC CTA CTT TCG TCA CGA TAT     638

Gly Ala Glu Ala Ile Ser Glu Pro Leu Asp Lys Ala Phe His Leu Leu
GGC GCA GAA GCC ATA TCC GAA CCG CTG GAC AAA GCG TTT CAC CTA CTG     686
```

FIG. 1A

```
Leu Asn Thr Tyr Gly Arg Pro Ile Arg Phe Leu Arg Glu Asn Thr Thr
CTC AAC ACC TAC GGG AGA CCC ATC CGC TTC CTG CGT GAA AAC ACC ACC    734

Gln Cys Thr Tyr Asn Ser Ser Leu Arg Asn Ser Thr Val Val Arg Glu
CAG TGT ACC TAC AAT AGC AGC CTC CGT AAC AGC ACG GTC GTC AGG GAA    782

Asn Ala Ile Ser Phe Asn Phe Phe Gln Ser Tyr Asn Gln Tyr Tyr Val
AAC GCC ATC AGT TTC AAC TTT TTC CAA AGC TAT AAT CAA TAC TAT GTA    830

Phe His Met Pro Arg Cys Leu Phe Ala Gly Pro Leu Ala Glu Gln Phe
TTC CAT ATG CCT CGA TGT CTT TTT GCG GGT CCT CTG GCG GAG CAG TTT    878

Leu Asn Gln Val Asp Leu Thr Glu Thr Leu Glu Arg Tyr Gln Gln Arg
CTG AAC CAG GTA GAT CTG ACC GAA ACC CTG GAA AGA TAC CAA CAG AGA    926

Leu Asn Thr Tyr Ala Leu Val Ser Lys Asp Leu Ala Ser Tyr Arg Ser
CTT AAC ACT TAC GCG CTG GTA TCC AAA GAC CTG GCC AGC TAC CGA TCT    974

Phe Ser Gln Gln Leu Lys Ala Gln Asp Ser Leu Gly Glu Gln Pro Thr
TTT TCG CAG CAG CTA AAG GCA CAG GAC AGC CTA GGT GAA CAG CCC ACC   1022

Thr Val Pro Pro Pro Ile Asp Leu Ser Ile Pro His Val Trp Met Pro
ACT GTG CCA CCA CCC ATT GAC CTG TCA ATA CCT CAC GTT TGG ATG CCA   1070

Pro Gln Thr Thr Pro His Gly Trp Thr Glu Ser His Thr Thr Ser Gly
CCG CAA ACC ACT CCA CAC GGC TGG ACA GAA TCA CAT ACC ACC TCA GGA   1118
```

FIG.1B

```
Leu His Arg Pro His Phe Asn Gln Thr Cys Ile Leu Phe Asp Gly His
CTA CAC CGA CCA CAC TTT AAC CAG ACC TGT ATC CTC TTT GAT GGA CAC     1166

Asp Leu Leu Phe Ser Thr Val Thr Pro Cys Leu His Gln Gly Phe Tyr
GAT CTA CTA TTC AGC ACC GTC ACA CCT TGT TTG CAC CAA GGC TTT TAC     1214

Leu Ile Asp Glu Leu Arg Tyr Val Lys Ile Thr Leu Thr Glu Asp Phe
CTC ATC GAC GAA CTA CGT TAC GTT AAA ATA ACA CTG ACC GAG GAC TTC     1262

Phe Val Val Thr Val Ser Ile Asp Asp Asp Thr Pro Met Leu Leu Ile
TTC GTA GTT ACG GTG TCC ATA GAC GAC GAC ACA CCC ATG CTG CTT ATC     1310

Phe Gly His Leu Pro Arg Val Leu Phe Lys Ala Pro Tyr Gln Arg Asp
TTC GGC CAT CTT CCA CGC GTA CTC TTT AAA GCG CCC TAT CAA CGC GAC     1358

Asn Phe Ile Leu Arg Gln Thr Glu Lys His Glu Leu Leu Val Leu Val
AAC TTT ATA CTA CGA CAA ACT GAA AAA CAC GAG CTC CTG GTG CTA GTT     1406

Lys Lys Asp Gln Leu Asn Arg His Ser Tyr Leu Lys Asp Pro Asp Phe
AAG AAA GAT CAA CTG AAC CGT CAC TCT TAT CTC AAA GAC CCG GAC TTT     1454

Leu Asp Ala Ala Leu Asp Phe Asn Tyr Leu Asp Leu Ser Ala Leu Leu
CTT GAC GCC GCA CTT GAC TTC AAC TAC CTG GAC CTC AGC GCA CTA CTA     1502

Arg Asn Ser Phe His Arg Tyr Ala Val Asp Val Leu Lys Ser Gly Arg
CGT AAC AGC TTT CAC CGT TAC GCC GTG GAT GTA CTC AAA AGC GGT CGA     1550
```

FIG. 1C

```
Cys Gln Met Leu Asp Arg Arg Thr Val Glu Met Ala Phe Ala Tyr Ala
TGT CAG ATG CTG GAC CGC CGC ACG GTA GAA ATG GCC TTC GCC TAC GCA    1598

Leu Ala Leu Phe Ala Ala Ala Arg Gln Glu Glu Ala Gly Ala Gln Val
TTA GCA CTG TTC GCA GCA GCC CGA CAA GAA GAG GCC GGC GCC CAA GTC    1646

Ser Val Pro Arg Ala Leu Asp Arg Gln Ala Ala Leu Leu Gln Ile Gln
TCC GTC CCA CGG GCC CTA GAC CGC CAG GCC GCA CTC TTA CAA ATA CAA    1694

Glu Phe Met Ile Thr Cys Leu Ser Gln Thr Pro Pro Arg Thr Thr Leu
GAA TTT ATG ATC ACC TGC CTC TCA CAA ACA CCA CCA CGC ACC ACG TTG    1742

Leu Leu Tyr Pro Thr Ala Val Asp Leu Ala Lys Arg Ala Leu Trp Thr
CTG CTG TAT CCC ACG GCC GTG GAC CTG GCC AAA CGA GCC CTT TGG ACA    1790

Pro Asn Gln Ile Thr Asp Ile Thr Ser Leu Val Arg Leu Val Tyr Ile
CCG AAT CAG ATC ACC GAC ATC ACC AGC CTC GTA CGC CTG GTC TAC ATA    1838

Leu Ser Lys Gln Asn Gln Gln His Leu Ile Pro Gln Trp Ala Leu Arg
CTC TCT AAA CAG AAT CAG CAA CAT CTC ATC CCC CAG TGG GCA CTA CGA    1886

Gln Ile Ala Asp Phe Ala Leu Lys Leu His Lys Thr His Leu Ala Ser
CAG ATC GCC GAC TTT GCC CTA AAA CTA CAC AAA ACG CAC CTG GCC TCT    1934

Phe Leu Ser Ala Phe Ala Arg Gln Glu Leu Tyr Leu Met Gly Ser Leu
TTT CTT TCA GCC TTC GCG CGT CAA GAA CTC TAC CTC ATG GGC AGC CTC    1982
```

FIG. 1D

```
Val His Ser Met Leu Val His Thr Thr Glu Arg Arg Glu Ile Phe Ile
GTC CAC TCC ATG CTA GTA CAT ACG ACG GAG AGA CGC GAA ATC TTC ATC      2030

Val Glu Thr Gly Leu Cys Ser Leu Ala Glu Leu Ser His Phe Thr Gln
GTA GAA ACG GGC CTC TGT TCA TTA GCC GAG CTA TCA CAC TTT ACG CAG      2078

Leu Leu Ala His Pro His His Glu Tyr Leu Ser Asp Leu Tyr Thr Pro
TTG CTA GCT CAT CCG CAC CAC GAA TAC CTC AGC GAC CTG TAC ACA CCC      2126

Cys Ser Ser Ser Gly Arg Arg Asp His Ser Leu Glu Arg Leu Thr Arg
TGT TCC AGT AGC GGG CGA CGC GAT CAC TCG CTC GAA CGC CTC ACA CGT      2174

Leu Phe Pro Asp Ala Thr Val Pro Thr Thr Val Pro Ala Ala Leu Ser
CTC TTC CCC GAT GCC ACC GTC CCC ACT ACC GTT CCC GCC GCC CTC TCC      2222

Ile Leu Ser Thr Met Gln Pro Ser Thr Leu Glu Thr Phe Pro Asp Leu
ATC CTA TCT ACC ATG CAA CCA AGC ACG CTA GAA ACC TTC CCC GAC CTG      2270

Phe Cys Leu Pro Leu Gly Glu Ser Phe Ser Ala Leu Thr Val Ser Glu
TTT TGT CTG CCG CTC GGC GAA TCC TTC TCC GCG CTG ACC GTC TCC GAA      2318

His Val Ser Tyr Val Val Thr Asn Gln Tyr Leu Ile Lys Gly Ile Ser
CAC GTC AGT TAT GTC GTA ACA AAC CAG TAC CTG ATC AAA GGT ATC TCC      2366

Tyr Pro Val Ser Thr Thr Val Val Gly Gln Ser Leu Ile Ile Thr Gln
TAC CCT GTC TCC ACC ACC GTC GTA GGC CAG AGC CTC ATC ATC ACC CAG      2414
```

FIG. 1E

```
Thr Asp Ser Gln Thr Lys Cys Glu Leu Thr Arg Asn Met His Thr Thr
ACG GAC AGT CAA ACT AAA TGC GAA CTG ACG CGC AAC ATG CAT ACC ACA       2462

His Ser Ile Thr Ala Ala Leu Asn Ile Ser Leu Glu Asn Cys Ala Phe
CAC AGC ATC ACA GCG GCG CTC AAC ATT TCC CTA GAA AAC TGC GCC TTT       2510

Cys Gln Ser Ala Leu Leu Glu Tyr Asp Asp Thr Gln Gly Val Ile Asn
TGC CAA AGC GCC CTA CTA GAA TAC GAC GAC ACG CAA GGC GTC ATC AAC       2558

Ile Met Tyr Met His Asp Ser Asp Asp Val Leu Phe Ala Leu Asp Pro
ATC ATG TAC ATG CAC GAC TCG GAC GAC GTC CTT TTC GCC CTG GAT CCC       2606

Tyr Asn Glu Val Val Val Ser Ser Pro Arg Thr His Tyr Leu Met Leu
TAC AAC GAA GTG GTG GTC TCA TCT CCG CGA ACT CAC TAC CTC ATG CTT       2654

Leu Lys Asn Gly Thr Val Leu Glu Val Thr Asp Val Val Val Asp Ala
TTG AAA AAC GGT ACG GTC CTA GAA GTA ACT GAC GTC GTC GTG GAC GCT       2702

Thr Asp Ser Arg Leu Leu Met Met Ser Val Tyr Ala Leu Ser Ala Ile
ACC GAC AGT CGT CTC CTC ATG ATG TCC GTC TAC GCG CTA TCG GCC ATC       2750

Ile Gly Ile Tyr Leu Leu Tyr Arg Met Leu Lys Thr Cys OP
ATC GGC ATC TAT CTG CTC TAC CGC ATG CTC AAG ACA TGC TGACTGTAGA        2799

ACCTGACAGT TTATGAGAAA AGGGACAGAG AAAGTTAAAG ACATTCACAC AAAATCTTCT     2859

AAAACGGTAC GGGCCCCAAT ACTTAGGGGC ACTCTTGCTC GTTGTAATAA AGTACACGCC     2919
```

FIG. 1F

```
ACACGGTGTG ATGGTACTAT ATGTGTGAGG TCTGTGCGTC TTTATTTACG AGGTACTGTT   2979
GTGGGTCTGG TTACATATCG GGCCTTGGAT ACAAGCTCGG TACACAGCCA AGGTGCGGGA   3039
GACTAGGTC                                                           3048
```

FIG.1G

```
P4
    P1                                                                                                                    1
1 MWSWKCLLFWAVLVTATLCTARPSPTLPEQAQPWGAPVEVESFLVHPGDLLQLRCRLRDDVQSINWLRDGVQLAE        75
2 MWSWKCLLFWAVLVTATLCTARPSPTLPEQAQPWGAPVEVESFLVHPGDLLQLRCRLRDDVQSINWLRDGVQLAE        75
3 MWSWKCLLFWAVLVTATLCTARPSPTLPEQ---------------------------------------------        30
4 MWSWKCLLFWAVLVTATLCTARPSPTLPEQ---------------------------------------------        30
5 MWSWKCLLFWAVLVTATLCTARPSPTLPEQ---------------------------------------------        30
6 MWSWKCLLFWAVLVTATLCTARPSPTLPEQ---------------------------------------------        30
                                                              ARR
  SNRTRITGEEVEVQDSVPADSGLYACVTSSPSGSDTTYFSVNVSDALPSSEDDDDDSSSEEKETDNTKPN            148
  SNRTRITGEEVEVQDSVPADSGLYACVTSSPSGSDTTYFSVNVSDALPSSEDDDDDSSSEEKETDNTKPNRMP          150
  -----------------------------------------------DALPSSEDDDDDSSSEEKETDNTKPN          59
  -----------------------------------------------DALPSSEDDDDDSSSEEKETDNTKPNRMP       61
  -----------------------------------------------DALPSSEDDDDDSSSEEKETDNTKPN          59
  -----------------------------------------------DALPSSEDDDDDSSSEEKETDNTKPNRMP       61
                                                              2
  VAPYWTSPEKMEKKLHAVPAAKTVKFKCPSSGTPNPTLRWLKNGKEFKPDHRIGGYKVRYATWSIIMDSVVPSDK        223
  VAPYWTSPEKMEKKLHAVPAAKTVKFKCPSSGTPNPTLRWLKNGKEFKPDHRIGGYKVRYATWSIIMDSVVPSDK        225
  VAPYWTSPEKMEKKLHAVPAAKTVKFKCPSSGTPNPTLRWLKNGKEFKPDHRIGGYKVRYATWSIIMDSVVPSDK        134
  VAPYWTSPEKMEKKLHAVPAAKTVKFKCPSSGTPNPTLRWLENGKEFKPDHRIGGYKVRYATWSIIMDSVVPSDK        136
  VAPYWTSPEKMEKKLHAVPAAKTVKFKCPSSGTPNPTLRWLKNGKEFKPDHRIGGYKVRYATWSIIMDSVVPSDK        134
  VAPYWTSPEKMEKKLHAVPAAKTVKFKCPSSGTPNPTLRWLKNGKEFKPDHRIGGYKVRYATWSIIMDSVVPSDK        136
                                                                    3               P3
  GNYTCIVENEYGSINHTYQLDVVERSPHRPILQAGLPANKTVALGSNVEFMCKVYSDPQPHIQWLKHIEVNGSKI        298
  GNYTCIVENEYGSINHTYQLDVVERSPHRPILQAGLPANKTVALGSNVEFMCKVYSDPQPHIQWLKHIEVNGSKI        300
  GNYTCIVENEYGSINHTYQLDVVERSPHRPILQAGLPANKTVALGSNVEFMCKVYSDPQPHIQWLKHIEVNGSKI        209
  GNYTCIVENEYGSINHTYQLDVVERSPHRPILQAGLPANKTVALGSNVEFMCKVYSDPQPHIQWLKHIEVNGSKI        211
  GNYTCIVENEYGSINHTYQLDVVERSPHRPILQAGLPANKTVALGSNVEFMCKVYSDPQPHIQWLKHIEVNGSKI        209
  GNYTCIVENEYGSINHTYQLDVVERSPHRPILQAGLPANKTVALGSNVEFMCKVYSDPQPHIQWLKHIEVNGSKI        211
         P2
  GPDNLPYVQILKTAGVNTTDKEMEVLHLRNVSFEDAGEYTCLAGNSIGLSHHSAWLTVLEALEERPAVMTSPLYL        373
  GPDNLPYVQILKTAGVNTTDKEMEVLHLRNVSFEDAGEYTCLAGNSIGLSHHSAWLTVLEALEERPAVMTSPLYL        375
  GPDNLPYVQILKTAGVNTTDKEMEVLHLRNVSFEDAGEYTCLAGNSIGLSHHSAWLTVLEALEERPAVMTSPLYL        284
  GPDNLPYVQILKTAGVNTTDKEMEVLHLRNVSFEDAGEYTCLAGNSIGLSHHSAWLTVLEALEERPAVMTSPLYL        286
  GPDNLPYVQILKVIMAPVFVGQSTGKETTVSGAQVPVGRLSCPRMGSFTLQAHTHLSRDLATSPRTSNRGHKV         284
  GPDNLPYVQILKVIMAPVFVGQSTGKETTVSGAQVPVGRLSCPRMGSFTLQAHTHLSRDLATSPRTSNRGHKV         286
```

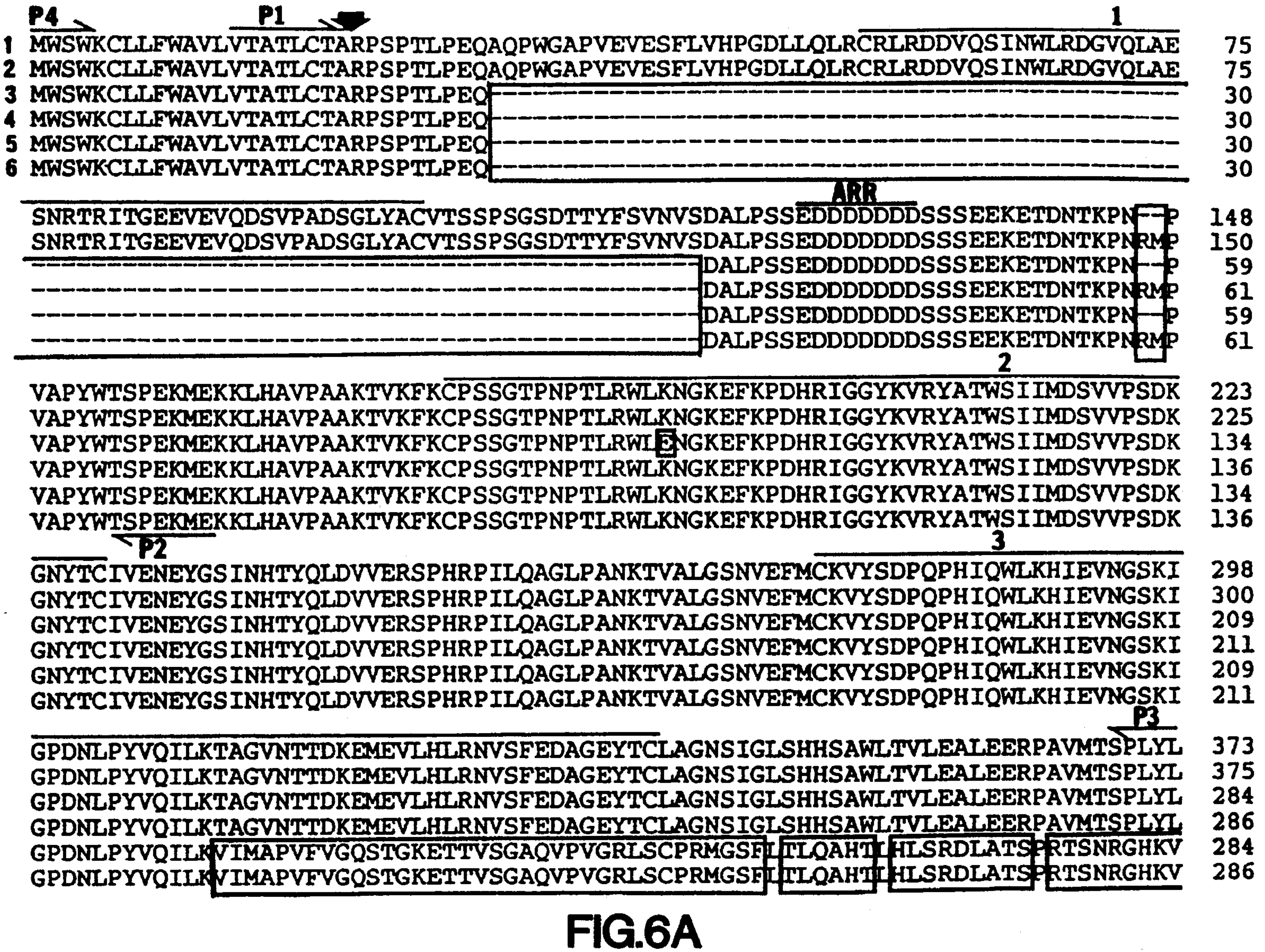

FIG.6A

```
  IM
EIIIYCTGAFLISCMVGSVIVYKMKSGTKKSDFHSQMAVHKLAKSIPLRRQVTVSADSSASMNSGVLLVRPSRLS  448
EIIIYCTGAFLISCMVGSVIVYKMKSGTKKSDFHSQMAVHKLAKSIPLRRQVTVSADSSASMNSGVLLVRPSRLS  450
EIIIYCTGAFLISCMVGSVIVYKMKSGTKKSDFHSQMAVHKLAKSIPLRRQVTVSADSSASMNSGVLLVRPSRLS  359
EIIIYCTGAFLISCMVGSVIVYKMKSGTKKSDFHSQMAVHKLAKSIPLRRQVTVSADSSASMNSGVLLVRPSRLS  361
EVSWEQRAAGMGGAGL*                                                            300
EVSWEQRAAGMGGAGL*                                                            302
                                                                     TK
SSGTPMLAGVSEYELPEDPRWELPRDRLVLGKPLGEGCFGQVVLAEAIGLDKDKPNRVTKVAVKMLKSDATEKDL  523
SSGTPMLAGVSEYELPEDPRWELPRDRLVLGKPLGEGCFGQVVLAEAIGLDKDKPNRVTKVAVKMLKSDATEKDL  525
SSGTPMLAGVSEYELPEDPRWELPRDRLVLGKPLGEGCFGQVVLAEAIGLDKDKPNRVTKVAVKMLKSDATEKDL  434
SSGTPMLAGVSEYELPEDPRWELPRDRLVLGKPLGEGCFGQVVLAEAIGLDKDKPNRVTKVAVKMLKSDATEKDL  436

SDLISEMEMMKMIGKHKNIINLLGACTQDGPLYVIVEYASKGNLREYLQARRPPGLEYCYNPSHNPEEQLSSKDL  598
SDLISEMEMMKMIGKHKNIINLLGACTQDGPLYVIVEYASKGNLREYLQARRPPGLEYCYNPSHNPEEQLSSKDL  600
SDLISEMEMMKMIGKHKNIINLLGACTQDGPLYVIVEYASKGNLREYLQARRPPGLEYCYNPSHNPEEQLSSKDL  509
SDLISEMEMMKMIGKHKNIINLLGACTQDGPLYVIVEYASKGNLREYLQARRPPGLEYCYNPSHNPEEQLSSKDL  511

VSCAYQVARGMEYLASKKCIHRDLAARNVLVTEDNVMKIADFGLARDIHHIDYYKKTTNGRLPVKWMAPEALFDR  673
VSCAYQVARGMEYLASKKCIHRDLAARNVLVTEDNVMKIADFGLARDIHHIDYYKKTTNGRLPVKWMAPEALFDR  675
VSCAYQVARGMEYLASKKCIHRDLAARNVLVTEDNVMKIADFGLARDIHHIDYYKKTTNGRLPVKWMAPEALFDR  584
VSCAYQVARGMEYLASKKCIHRDLAARNVLVTEDNVMKIADFGLARDIHHIDYYKKTTNGRLPVKWMAPEALFDR  586
                             TK
IYTHQSDVWSFGVLLWEIFTLGGSPYPGVPVEELFKLLKEGHRMDKPSNCTNELYMMMRDCWHAVPSQRPTFKQL  748
IYTHQSDVWSFGVLLWEIFTLGGSPYPGVPVEELFKLLKEGHRMDKPSNCTNELYMMMRDCWHAVPSQRPTFKQL  750
IYTHQSDVWSFGVLLWEIFTLGGSPYPGVPVEELFKLLKEGHRMDKPSNCTNELYMMMRDCWHAVPSQRPTFKQL  659
IYTHQSDVWSFGVLLWEIFTLGGSPYPGVPVEELFKLLKEGHRMDKPSNCTNELYMMMRDCWHAVPSQRPTFKQL  661

VEDLDRIVALTSNQEYLDLSMPLDQYSPSFPDTRSSTCSSGEDSVFSHEPLPEEPCLPRHPAQLANGGLKRR*  820
VEDLDRIVALTSNQEYLDLSMPLDQYSPSFPDTRSSTCSSGEDSVFSHEPLPEEPCLPRHPAQLANRGLKRR*  822
VEDLDRIVALTSNQEYLDLSMPLDQYSPSFPDTRSSTCSSGEDSVFSHEPLPEEPCLPRHPAQLANGGLKRR*  731
VEDLDRIVALTSNQEYLDLSMPLDQYSPSFPDTRSSTCSSGEDSVFSHEPLPEEPCLPRHPAQLANGGLKRR*  733
```

FIG.6B

```
                       CGCCAACTGGCTCCTTACCGTCACACT

CTCATCGTGCCGCAGACTTGATGTGCCGCCGCCCGGATTGCGGCTTCTCT    30
                     M  C  R  R  P  D  C  G  F  S     10

                   t*
TTCTCACCTGGACCGGTGGCACTGCTGTGGTGTTGCCTTCTGCTGCCCAT
 F  S  P  G  P  V  A  L  L  W  C  C  L  L  L  P  I

t          t*g*                    c*           c
CGTTTCCTCAGCCACCGTCAGCGTCGCTCCTACCGTCGCCGAGAAAGTTC    130
  V  S  S  A  T  V  S  V  A  P  T  V  A  E  K  V      43

CCGCGGAGTGCCCCGAACTAACGCGTCGATGCCTGTTGGGTGAGGTGTTT
P  A  E  C  P  E  L  T  R  R  C  L  L  G  E  V  F

CAGGGTGACAAGTATGAAAGTTGGCTGCGCCCGTTGGTGAATGTTACCAG    230
 Q  G  D  K  Y  E  S  W  L  R  P  L  V  N  V  T  R     77

ACGCGATGGCCCGCTATCGCAACTTATTCGTTACCGTCCCGTTACGCCGG
  R  D  G  P  L  S  Q  L  I  R  Y  R  P  V  T  P

AGGCCGCCAACTCCGTGCTGTTGGACGATGCTTTCCTGGACACTCTGGCC    330
E  A  A  N  S  V  L  L  D  D  A  F  L  D  T  L  A     110

                                 c
CTGCTGTACAACAATCCGGATCAATTGCGGGCCTTGCTGACGCTGTTGAG
 L  L  Y  N  N  P  D  Q  L  R  A  L  L  T  L  L  S

                                       c
CTCGGACACAGCGCCGCGCTGGATGACGGTGATGCGCGGTTACAGCGAGT    440
  S  D  T  A  P  R  W  M  T  V  M  R  G  Y  S  E      143

GCGGCGATGGCTCGCCGGCCGTGTACACGTGCGTGGACGACCTGTGCCGC
C  G  D  G  S  P  A  V  Y  T  C  V  D  D  L  C  R

GGCTACGACCTCACGCGACTGTCATACGGGCGCAGCATCTTCACGGAACA    540
 G  Y  D  L  T  R  L  S  Y  G  R  S  I  F  T  E  H     177

CGTGTTAGGCTTCGAGCTGGTGCCACCGTCTCTCTTTAACGTGGTGGTGG
  V  L  G  F  E  L  V  P  P  S  L  F  N  V  V  V

CCATACGCAACGAAGCCACGCGTACCAACCGCGCCGTGCGTCTGCCCGTG    640
A  I  R  N  E  A  T  R  T  N  R  A  V  R  L  P  V     210

                             a
AGCACCGCTGCCGCGCCCGAGGGCATCACGCTCTTTTACGGCCTGTACAA
 S  T  A  A  A  P  E  G  I  T  L  F  Y  G  L  Y  N

                                             a
CGCAGTGAAGGAATTCTGCCTGCGTCACCAGCTGGACCCGCCGCTGCTAC    740
  A  V  K  E  F  C  L  R  H  Q  L  D  P  P  L  L      243

GCCACCTAGATAAATACTACGCCGGACTGCCGCCCGAGCTGAAGCAGACG
R  H  L  D  K  Y  Y  A  G  L  P  P  E  L  K  Q  T

CGCGTCAACCTGCCGGCTCACTCGCGCTATGGCCCTCAAGCAGTGGATGC    840
 R  V  N  L  P  A  H  S  R  Y  G  P  Q  A  V  D  A     277

TCGCTAACATTGCTGATAATAAAGGCTCTCTGTTAACCCCCGACGAGCAG
  R  O

GCTCGCGTGTTTTGTCTGAGCGCCGACTGGATCC                    924
                                                      278
```

FIG. 7

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 3048 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 564..2790

( x i ) SEQUENCE DESCRIPTION: SEQ ID NO:1:

```
CTGCAGGCTG TGGGTGGCGT GCCACCGCAC GGACTGATCG TCGGCGTCTG AGTACGTAGT      60

TTTGAACTCA ATCACGTAGC AATACACGAT GCCGCGCGAC CCAGAGTCCG GCGGTAAAAA     120

CACCAACACG CAGTCGGGAA TCCGCCGACT TAATCGTACT TCGATGAAAA GACGGCGACG     180

GTACTTTTGC AACTCGGGTG GGAAAAGGCC TCCCAACAGG CGGTTGAGCG CCACAAATGA     240

GGGAAAGACC CGCAGCAGGC GACGGTAGAT GTCCAGGTGC TTGCGCTTAC CGATCCGCTT     300

ACGCACGTGA GGCAATCTCC GCAGAGCGTT CCCCTTCGAA TCAGCGTCGT CCCCACACCC     360

GGACGGCATG ACTTACTCGC GTGTCCCCTC TTCTCCCTTC GCAGCGGCCA ATGACATCGT     420

ATTAAATAGA CGGAGACGCG ACTTTTGTAA CCCGTAGCGC CGCACCCGGG TGCTCCTTCC     480

TGGGATCCTT TCTCTCCTTC TCTCGGGTGT AACGCCAACC ACCACCTGGA TCACGCCGCT     540

GAACCCAGCG GCGCGGCCGC GCT ATG CGG CCA GGC CTC CCC TCC TAC CTC         590
                          Met Arg Pro Gly Leu Pro Ser Tyr Leu
                           1               5

ATC GTC CTC GCC GTC TGT CTC CTC AGC CAC CTA CTT TCG TCA CGA TAT       638
Ile Val Leu Ala Val Cys Leu Leu Ser His Leu Leu Ser Ser Arg Tyr
 10                  15                  20                  25

GGC GCA GAA GCC ATA TCC GAA CCG CTG GAC AAA GCG TTT CAC CTA CTG       686
Gly Ala Glu Ala Ile Ser Glu Pro Leu Asp Lys Ala Phe His Leu Leu
                 30                  35                  40

CTC AAC ACC TAC GGG AGA CCC ATC CGC TTC CTG CGT GAA AAC ACC ACC       734
Leu Asn Thr Tyr Gly Arg Pro Ile Arg Phe Leu Arg Glu Asn Thr Thr
             45                  50                  55

CAG TGT ACC TAC AAT AGC AGC CTC CGT AAC AGC ACG GTC GTC AGG GAA       782
Gln Cys Thr Tyr Asn Ser Ser Leu Arg Asn Ser Thr Val Val Arg Glu
         60                  65                  70
```

-continued

```
AAC GCC ATC AGT TTC AAC TTT TTC CAA AGC TAT AAT CAA TAC TAT GTA       830
Asn Ala Ile Ser Phe Asn Phe Phe Gln Ser Tyr Asn Gln Tyr Tyr Val
    75                  80                  85

TTC CAT ATG CCT CGA TGT CTT TTT GCG GGT CCT CTG GCG GAG CAG TTT       878
Phe His Met Pro Arg Cys Leu Phe Ala Gly Pro Leu Ala Glu Gln Phe
90                  95                  100                 105

CTG AAC CAG GTA GAT CTG ACC GAA ACC CTG GAA AGA TAC CAA CAG AGA       926
Leu Asn Gln Val Asp Leu Thr Glu Thr Leu Glu Arg Tyr Gln Gln Arg
                110                 115                 120

CTT AAC ACT TAC GCG CTG GTA TCC AAA GAC CTG GCC AGC TAC CGA TCT       974
Leu Asn Thr Tyr Ala Leu Val Ser Lys Asp Leu Ala Ser Tyr Arg Ser
            125                 130                 135

TTT TCG CAG CAG CTA AAG GCA CAG GAC AGC CTA GGT GAA CAG CCC ACC      1022
Phe Ser Gln Gln Leu Lys Ala Gln Asp Ser Leu Gly Glu Gln Pro Thr
        140                 145                 150

ACT GTG CCA CCA CCC ATT GAC CTG TCA ATA CCT CAC GTT TGG ATG CCA      1070
Thr Val Pro Pro Pro Ile Asp Leu Ser Ile Pro His Val Trp Met Pro
    155                 160                 165

CCG CAA ACC ACT CCA CAC GGC TGG ACA GAA TCA CAT ACC ACC TCA GGA      1118
Pro Gln Thr Thr Pro His Gly Trp Thr Glu Ser His Thr Thr Ser Gly
170                 175                 180                 185

CTA CAC CGA CCA CAC TTT AAC CAG ACC TGT ATC CTC TTT GAT GGA CAC      1166
Leu His Arg Pro His Phe Asn Gln Thr Cys Ile Leu Phe Asp Gly His
                190                 195                 200

GAT CTA CTA TTC AGC ACC GTC ACA CCT TGT TTG CAC CAA GGC TTT TAC      1214
Asp Leu Leu Phe Ser Thr Val Thr Pro Cys Leu His Gln Gly Phe Tyr
            205                 210                 215

CTC ATC GAC GAA CTA CGT TAC GTT AAA ATA ACA CTG ACC GAG GAC TTC      1262
Leu Ile Asp Glu Leu Arg Tyr Val Lys Ile Thr Leu Thr Glu Asp Phe
        220                 225                 230

TTC GTA GTT ACG GTG TCC ATA GAC GAC GAC ACA CCC ATG CTG CTT ATC      1310
Phe Val Val Thr Val Ser Ile Asp Asp Asp Thr Pro Met Leu Leu Ile
    235                 240                 245

TTC GGC CAT CTT CCA CGC GTA CTC TTT AAA GCG CCC TAT CAA CGC GAC      1358
Phe Gly His Leu Pro Arg Val Leu Phe Lys Ala Pro Tyr Gln Arg Asp
250                 255                 260                 265

AAC TTT ATA CTA CGA CAA ACT GAA AAA CAC GAG CTC CTG GTG CTA GTT      1406
Asn Phe Ile Leu Arg Gln Thr Glu Lys His Glu Leu Leu Val Leu Val
                270                 275                 280

AAG AAA GAT CAA CTG AAC CGT CAC TCT TAT CTC AAA GAC CCG GAC TTT      1454
Lys Lys Asp Gln Leu Asn Arg His Ser Tyr Leu Lys Asp Pro Asp Phe
            285                 290                 295

CTT GAC GCC GCA CTT GAC TTC AAC TAC CTG GAC CTC AGC GCA CTA CTA      1502
Leu Asp Ala Ala Leu Asp Phe Asn Tyr Leu Asp Leu Ser Ala Leu Leu
        300                 305                 310

CGT AAC AGC TTT CAC CGT TAC GCC GTG GAT GTA CTC AAA AGC GGT CGA      1550
Arg Asn Ser Phe His Arg Tyr Ala Val Asp Val Leu Lys Ser Gly Arg
    315                 320                 325

TGT CAG ATG CTG GAC CGC CGC ACG GTA GAA ATG GCC TTC GCC TAC GCA      1598
Cys Gln Met Leu Asp Arg Arg Thr Val Glu Met Ala Phe Ala Tyr Ala
330                 335                 340                 345

TTA GCA CTG TTC GCA GCA GCC CGA CAA GAA GAG GCC GGC GCC CAA GTC      1646
Leu Ala Leu Phe Ala Ala Ala Arg Gln Glu Glu Ala Gly Ala Gln Val
                350                 355                 360

TCC GTC CCA CGG GCC CTA GAC CGC CAG GCC GCA CTC TTA CAA ATA CAA      1694
Ser Val Pro Arg Ala Leu Asp Arg Gln Ala Ala Leu Leu Gln Ile Gln
            365                 370                 375

GAA TTT ATG ATC ACC TGC CTC TCA CAA ACA CCA CCA CGC ACC ACG TTG      1742
Glu Phe Met Ile Thr Cys Leu Ser Gln Thr Pro Pro Arg Thr Thr Leu
```

-continued 380 385 390

CTG CTG TAT CCC ACG GCC GTG GAC CTG GCC AAA CGA GCC CTT TGG ACA 1790
Leu Leu Tyr Pro Thr Ala Val Asp Leu Ala Lys Arg Ala Leu Trp Thr
395 400 405

CCG AAT CAG ATC ACC GAC ATC ACC AGC CTC GTA CGC CTG GTC TAC ATA 1838
Pro Asn Gln Ile Thr Asp Ile Thr Ser Leu Val Arg Leu Val Tyr Ile
410 415 420 425

CTC TCT AAA CAG AAT CAG CAA CAT CTC ATC CCC CAG TGG GCA CTA CGA 1886
Leu Ser Lys Gln Asn Gln Gln His Leu Ile Pro Gln Trp Ala Leu Arg
430 435 440

CAG ATC GCC GAC TTT GCC CTA AAA CTA CAC AAA ACG CAC CTG GCC TCT 1934
Gln Ile Ala Asp Phe Ala Leu Lys Leu His Lys Thr His Leu Ala Ser
445 450 455

TTT CTT TCA GCC TTC GCG CGT CAA GAA CTC TAC CTC ATG GGC AGC CTC 1982
Phe Leu Ser Ala Phe Ala Arg Gln Glu Leu Tyr Leu Met Gly Ser Leu
460 465 470

GTC CAC TCC ATG CTA GTA CAT ACG ACG GAG AGA CGC GAA ATC TTC ATC 2030
Val His Ser Met Leu Val His Thr Thr Glu Arg Arg Glu Ile Phe Ile
475 480 485

GTA GAA ACG GGC CTC TGT TCA TTA GCC GAG CTA TCA CAC TTT ACG CAG 2078
Val Glu Thr Gly Leu Cys Ser Leu Ala Glu Leu Ser His Phe Thr Gln
490 495 500 505

TTG CTA GCT CAT CCG CAC CAC GAA TAC CTC AGC GAC CTG TAC ACA CCC 2126
Leu Leu Ala His Pro His His Glu Tyr Leu Ser Asp Leu Tyr Thr Pro
510 515 520

TGT TCC AGT AGC GGG CGA CGC GAT CAC TCG CTC GAA CGC CTC ACA CGT 2174
Cys Ser Ser Ser Gly Arg Arg Asp His Ser Leu Glu Arg Leu Thr Arg
525 530 535

CTC TTC CCC GAT GCC ACC GTC CCC ACT ACC GTT CCC GCC GCC CTC TCC 2222
Leu Phe Pro Asp Ala Thr Val Pro Thr Thr Val Pro Ala Ala Leu Ser
540 545 550

ATC CTA TCT ACC ATG CAA CCA AGC ACG CTA GAA ACC TTC CCC GAC CTG 2270
Ile Leu Ser Thr Met Gln Pro Ser Thr Leu Glu Thr Phe Pro Asp Leu
555 560 565

TTT TGT CTG CCG CTC GGC GAA TCC TTC TCC GCG CTG ACC GTC TCC GAA 2318
Phe Cys Leu Pro Leu Gly Glu Ser Phe Ser Ala Leu Thr Val Ser Glu
570 575 580 585

CAC GTC AGT TAT GTC GTA ACA AAC CAG TAC CTG ATC AAA GGT ATC TCC 2366
His Val Ser Tyr Val Val Thr Asn Gln Tyr Leu Ile Lys Gly Ile Ser
590 595 600

TAC CCT GTC TCC ACC ACC GTC GTA GGC CAG AGC CTC ATC ATC ACC CAG 2414
Tyr Pro Val Ser Thr Thr Val Val Gly Gln Ser Leu Ile Ile Thr Gln
605 610 615

ACG GAC AGT CAA ACT AAA TGC GAA CTG ACG CGC AAC ATG CAT ACC ACA 2462
Thr Asp Ser Gln Thr Lys Cys Glu Leu Thr Arg Asn Met His Thr Thr
620 625 630

CAC AGC ATC ACA GCG GCG CTC AAC ATT TCC CTA GAA AAC TGC GCC TTT 2510
His Ser Ile Thr Ala Ala Leu Asn Ile Ser Leu Glu Asn Cys Ala Phe
635 640 645

TGC CAA AGC GCC CTA CTA GAA TAC GAC GAC ACG CAA GGC GTC ATC AAC 2558
Cys Gln Ser Ala Leu Leu Glu Tyr Asp Asp Thr Gln Gly Val Ile Asn
650 655 660 665

ATC ATG TAC ATG CAC GAC TCG GAC GAC GTC CTT TTC GCC CTG GAT CCC 2606
Ile Met Tyr Met His Asp Ser Asp Asp Val Leu Phe Ala Leu Asp Pro
670 675 680

TAC AAC GAA GTG GTG GTC TCA TCT CCG CGA ACT CAC TAC CTC ATG CTT 2654
Tyr Asn Glu Val Val Val Ser Ser Pro Arg Thr His Tyr Leu Met Leu
685 690 695

TTG AAA AAC GGT ACG GTC CTA GAA GTA ACT GAC GTC GTC GTG GAC GCT 2702

-continued

Leu Lys Asn Gly Thr Val Leu Glu Val Thr Asp Val Val Val Asp Ala
700 705 710

ACC GAC AGT CGT CTC CTC ATG ATG TCC GTC TAC GCG CTA TCG GCC ATC 2750
Thr Asp Ser Arg Leu Leu Met Met Ser Val Tyr Ala Leu Ser Ala Ile
715 720 725

ATC GGC ATC TAT CTG CTC TAC CGC ATG CTC AAG ACA TGC T GACTGTAGAA 2800
Ile Gly Ile Tyr Leu Leu Tyr Arg Met Leu Lys Thr Cys
730 735 740

CCTGACAGTT TATGAGAAAA GGGACAGAGA AAGTTAAAGA CATTCACACA AAATCTTCTA 2860

AAACGGTACG GGCCCCAATA CTTAGGGGCA CTCTTGCTCG TTGTAATAAA GTACACGCCA 2920

CACGGTGTGA TGGTACTATA TGTGTGAGGT CTGTGCGTCT TTATTTACGA GGTACTGTTG 2980

TGGGTCTGGT TACATATCGG GCCTTGGATA CAAGCTCGGT ACACAGCCAA GGTGCGGGAG 3040

ACTAGGTC 3048

( 2 ) INFORMATION FOR SEQ ID NO:2:

( i ) SEQUENCE CHARACTERISTICS:
( A ) LENGTH: 742 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Arg Pro Gly Leu Pro Ser Tyr Leu Ile Val Leu Ala Val Cys Leu
1 5 10 15

Leu Ser His Leu Leu Ser Ser Arg Tyr Gly Ala Glu Ala Ile Ser Glu
20 25 30

Pro Leu Asp Lys Ala Phe His Leu Leu Leu Asn Thr Tyr Gly Arg Pro
35 40 45

Ile Arg Phe Leu Arg Glu Asn Thr Thr Gln Cys Thr Tyr Asn Ser Ser
50 55 60

Leu Arg Asn Ser Thr Val Val Arg Glu Asn Ala Ile Ser Phe Asn Phe
65 70 75 80

Phe Gln Ser Tyr Asn Gln Tyr Tyr Val Phe His Met Pro Arg Cys Leu
85 90 95

Phe Ala Gly Pro Leu Ala Glu Gln Phe Leu Asn Gln Val Asp Leu Thr
100 105 110

Glu Thr Leu Glu Arg Tyr Gln Gln Arg Leu Asn Thr Tyr Ala Leu Val
115 120 125

Ser Lys Asp Leu Ala Ser Tyr Arg Ser Phe Ser Gln Gln Leu Lys Ala
130 135 140

Gln Asp Ser Leu Gly Glu Gln Pro Thr Thr Val Pro Pro Pro Ile Asp
145 150 155 160

Leu Ser Ile Pro His Val Trp Met Pro Pro Gln Thr Thr Pro His Gly
165 170 175

Trp Thr Glu Ser His Thr Thr Ser Gly Leu His Arg Pro His Phe Asn
180 185 190

Gln Thr Cys Ile Leu Phe Asp Gly His Asp Leu Leu Phe Ser Thr Val
195 200 205

Thr Pro Cys Leu His Gln Gly Phe Tyr Leu Ile Asp Glu Leu Arg Tyr
210 215 220

Val Lys Ile Thr Leu Thr Glu Asp Phe Phe Val Val Thr Val Ser Ile
225 230 235 240

Asp Asp Asp Thr Pro Met Leu Leu Ile Phe Gly His Leu Pro Arg Val

-continued

| | | | | | | | | | | | | | | | |
|---|---|---|---|---|---|---|---|---|---|---|---|---|---|---|---|
| | | | | 245 | | | | | 250 | | | | | 255 | |
| Leu | Phe | Lys | Ala | Pro | Tyr | Gln | Arg | Asp | Asn | Phe | Ile | Leu | Arg | Gln | Thr |
| | | | 260 | | | | | 265 | | | | | 270 | | |
| Glu | Lys | His | Glu | Leu | Leu | Val | Leu | Val | Lys | Lys | Asp | Gln | Leu | Asn | Arg |
| | | 275 | | | | | 280 | | | | | 285 | | | |
| His | Ser | Tyr | Leu | Lys | Asp | Pro | Asp | Phe | Leu | Asp | Ala | Ala | Leu | Asp | Phe |
| | 290 | | | | | 295 | | | | | 300 | | | | |
| Asn | Tyr | Leu | Asp | Leu | Ser | Ala | Leu | Leu | Arg | Asn | Ser | Phe | His | Arg | Tyr |
| 305 | | | | | 310 | | | | | 315 | | | | | 320 |
| Ala | Val | Asp | Val | Leu | Lys | Ser | Gly | Arg | Cys | Gln | Met | Leu | Asp | Arg | Arg |
| | | | | 325 | | | | | 330 | | | | | 335 | |
| Thr | Val | Glu | Met | Ala | Phe | Ala | Tyr | Ala | Leu | Ala | Leu | Phe | Ala | Ala | Ala |
| | | | 340 | | | | | 345 | | | | | 350 | | |
| Arg | Gln | Glu | Glu | Ala | Gly | Ala | Gln | Val | Ser | Val | Pro | Arg | Ala | Leu | Asp |
| | | 355 | | | | | 360 | | | | | 365 | | | |
| Arg | Gln | Ala | Ala | Leu | Leu | Gln | Ile | Gln | Glu | Phe | Met | Ile | Thr | Cys | Leu |
| | 370 | | | | | 375 | | | | | 380 | | | | |
| Ser | Gln | Thr | Pro | Pro | Arg | Thr | Thr | Leu | Leu | Leu | Tyr | Pro | Thr | Ala | Val |
| 385 | | | | | 390 | | | | | 395 | | | | | 400 |
| Asp | Leu | Ala | Lys | Arg | Ala | Leu | Trp | Thr | Pro | Asn | Gln | Ile | Thr | Asp | Ile |
| | | | | 405 | | | | | 410 | | | | | 415 | |
| Thr | Ser | Leu | Val | Arg | Leu | Val | Tyr | Ile | Leu | Ser | Lys | Gln | Asn | Gln | Gln |
| | | | 420 | | | | | 425 | | | | | 430 | | |
| His | Leu | Ile | Pro | Gln | Trp | Ala | Leu | Arg | Gln | Ile | Ala | Asp | Phe | Ala | Leu |
| | | 435 | | | | | 440 | | | | | 445 | | | |
| Lys | Leu | His | Lys | Thr | His | Leu | Ala | Ser | Phe | Leu | Ser | Ala | Phe | Ala | Arg |
| | 450 | | | | | 455 | | | | | 460 | | | | |
| Gln | Glu | Leu | Tyr | Leu | Met | Gly | Ser | Leu | Val | His | Ser | Met | Leu | Val | His |
| 465 | | | | | 470 | | | | | 475 | | | | | 480 |
| Thr | Thr | Glu | Arg | Arg | Glu | Ile | Phe | Ile | Val | Glu | Thr | Gly | Leu | Cys | Ser |
| | | | | 485 | | | | | 490 | | | | | 495 | |
| Leu | Ala | Glu | Leu | Ser | His | Phe | Thr | Gln | Leu | Leu | Ala | His | Pro | His | His |
| | | | 500 | | | | | 505 | | | | | 510 | | |
| Glu | Tyr | Leu | Ser | Asp | Leu | Tyr | Thr | Pro | Cys | Ser | Ser | Ser | Gly | Arg | Arg |
| | | 515 | | | | | 520 | | | | | 525 | | | |
| Asp | His | Ser | Leu | Glu | Arg | Leu | Thr | Arg | Leu | Phe | Pro | Asp | Ala | Thr | Val |
| | 530 | | | | | 535 | | | | | 540 | | | | |
| Pro | Thr | Thr | Val | Pro | Ala | Ala | Leu | Ser | Ile | Leu | Ser | Thr | Met | Gln | Pro |
| 545 | | | | | 550 | | | | | 555 | | | | | 560 |
| Ser | Thr | Leu | Glu | Thr | Phe | Pro | Asp | Leu | Phe | Cys | Leu | Pro | Leu | Gly | Glu |
| | | | | 565 | | | | | 570 | | | | | 575 | |
| Ser | Phe | Ser | Ala | Leu | Thr | Val | Ser | Glu | His | Val | Ser | Tyr | Val | Val | Thr |
| | | | 580 | | | | | 585 | | | | | 590 | | |
| Asn | Gln | Tyr | Leu | Ile | Lys | Gly | Ile | Ser | Tyr | Pro | Val | Ser | Thr | Thr | Val |
| | | 595 | | | | | 600 | | | | | 605 | | | |
| Val | Gly | Gln | Ser | Leu | Ile | Ile | Thr | Gln | Thr | Asp | Ser | Gln | Thr | Lys | Cys |
| | 610 | | | | | 615 | | | | | 620 | | | | |
| Glu | Leu | Thr | Arg | Asn | Met | His | Thr | Thr | His | Ser | Ile | Thr | Ala | Ala | Leu |
| 625 | | | | | 630 | | | | | 635 | | | | | 640 |
| Asn | Ile | Ser | Leu | Glu | Asn | Cys | Ala | Phe | Cys | Gln | Ser | Ala | Leu | Leu | Glu |
| | | | | 645 | | | | | 650 | | | | | 655 | |
| Tyr | Asp | Asp | Thr | Gln | Gly | Val | Ile | Asn | Ile | Met | Tyr | Met | His | Asp | Ser |
| | | | 660 | | | | | 665 | | | | | 670 | | |

-continued

| | | | | | | | | | | | | | | | |
|---|---|---|---|---|---|---|---|---|---|---|---|---|---|---|---|
| Asp | Asp | Val | Leu | Phe | Ala | Leu | Asp | Pro | Tyr | Asn | Glu | Val | Val | Val | Ser |
| | | 675 | | | | | 680 | | | | | 685 | | | |
| Ser | Pro | Arg | Thr | His | Tyr | Leu | Met | Leu | Leu | Lys | Asn | Gly | Thr | Val | Leu |
| | 690 | | | | | 695 | | | | | 700 | | | | |
| Glu | Val | Thr | Asp | Val | Val | Val | Asp | Ala | Thr | Asp | Ser | Arg | Leu | Leu | Met |
| 705 | | | | | 710 | | | | | 715 | | | | | 720 |
| Met | Ser | Val | Tyr | Ala | Leu | Ser | Ala | Ile | Ile | Gly | Ile | Tyr | Leu | Leu | Tyr |
| | | | | 725 | | | | | 730 | | | | | 735 | |
| Arg | Met | Leu | Lys | Thr | Cys | | | | | | | | | | |
| | | | 740 | | | | | | | | | | | | |

( 2 ) INFORMATION FOR SEQ ID NO:3:

( i ) SEQUENCE CHARACTERISTICS:
( A ) LENGTH: 820 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Trp | Ser | Trp | Lys | Cys | Leu | Leu | Phe | Trp | Ala | Val | Leu | Val | Thr | Ala |
| 1 | | | | 5 | | | | | 10 | | | | | 15 | |
| Thr | Leu | Cys | Thr | Ala | Arg | Pro | Ser | Pro | Thr | Leu | Pro | Glu | Gln | Ala | Gln |
| | | | 20 | | | | | 25 | | | | | 30 | | |
| Pro | Trp | Gly | Ala | Pro | Val | Glu | Val | Glu | Ser | Phe | Leu | Val | His | Pro | Gly |
| | | 35 | | | | | 40 | | | | | 45 | | | |
| Asp | Leu | Leu | Gln | Leu | Arg | Cys | Arg | Leu | Arg | Asp | Asp | Val | Gln | Ser | Ile |
| | 50 | | | | | 55 | | | | | 60 | | | | |
| Asn | Trp | Leu | Arg | Asp | Gly | Val | Gln | Leu | Ala | Glu | Ser | Asn | Arg | Thr | Arg |
| 65 | | | | | 70 | | | | | 75 | | | | | 80 |
| Ile | Thr | Gly | Glu | Glu | Val | Glu | Val | Gln | Asp | Ser | Val | Pro | Ala | Asp | Ser |
| | | | | 85 | | | | | 90 | | | | | 95 | |
| Gly | Leu | Tyr | Ala | Cys | Val | Thr | Ser | Ser | Pro | Ser | Gly | Ser | Asp | Thr | Thr |
| | | | 100 | | | | | 105 | | | | | 110 | | |
| Tyr | Phe | Ser | Val | Asn | Val | Ser | Asp | Ala | Leu | Pro | Ser | Ser | Glu | Asp | Asp |
| | | 115 | | | | | 120 | | | | | 125 | | | |
| Asp | Asp | Asp | Asp | Asp | Ser | Ser | Ser | Glu | Glu | Lys | Glu | Thr | Asp | Asn | Thr |
| | 130 | | | | | 135 | | | | | 140 | | | | |
| Lys | Pro | Asn | Pro | Val | Ala | Pro | Tyr | Trp | Thr | Ser | Pro | Glu | Lys | Met | Glu |
| 145 | | | | | 150 | | | | | 155 | | | | | 160 |
| Lys | Lys | Leu | His | Ala | Val | Pro | Ala | Ala | Lys | Thr | Val | Lys | Phe | Lys | Cys |
| | | | | 165 | | | | | 170 | | | | | 175 | |
| Pro | Ser | Ser | Gly | Thr | Pro | Asn | Pro | Thr | Leu | Arg | Trp | Leu | Lys | Asn | Gly |
| | | | 180 | | | | | 185 | | | | | 190 | | |
| Lys | Glu | Phe | Lys | Pro | Asp | His | Arg | Ile | Gly | Gly | Tyr | Lys | Val | Arg | Tyr |
| | | 195 | | | | | 200 | | | | | 205 | | | |
| Ala | Thr | Trp | Ser | Ile | Ile | Met | Asp | Ser | Val | Val | Pro | Ser | Asp | Lys | Gly |
| | 210 | | | | | 215 | | | | | 220 | | | | |
| Asn | Tyr | Thr | Cys | Ile | Val | Glu | Asn | Glu | Tyr | Gly | Ser | Ile | Asn | His | Thr |
| 225 | | | | | 230 | | | | | 235 | | | | | 240 |
| Tyr | Gln | Leu | Asp | Val | Val | Glu | Arg | Ser | Pro | His | Arg | Pro | Ile | Leu | Gln |
| | | | | 245 | | | | | 250 | | | | | 255 | |
| Ala | Gly | Leu | Pro | Ala | Asn | Lys | Thr | Val | Ala | Leu | Gly | Ser | Asn | Val | Glu |
| | | | 260 | | | | | 265 | | | | | 270 | | |

-continued

| | | | | | | | | | | | | | | | |
|---|---|---|---|---|---|---|---|---|---|---|---|---|---|---|---|
| Phe | Met | Cys | Lys | Val | Tyr | Ser | Asp | Pro | Gln | Pro | His | Ile | Gln | Trp | Leu |
| | | 275 | | | | | 280 | | | | | 285 | | | |
| Lys | His | Ile | Glu | Val | Asn | Gly | Ser | Lys | Ile | Gly | Pro | Asp | Asn | Leu | Pro |
| | 290 | | | | | 295 | | | | | 300 | | | | |
| Tyr | Val | Gln | Ile | Leu | Lys | Thr | Ala | Gly | Val | Asn | Thr | Thr | Asp | Lys | Glu |
| 305 | | | | | 310 | | | | | 315 | | | | | 320 |
| Met | Glu | Val | Leu | His | Leu | Arg | Asn | Val | Ser | Phe | Glu | Asp | Ala | Gly | Glu |
| | | | | 325 | | | | | 330 | | | | | 335 | |
| Tyr | Thr | Cys | Leu | Ala | Gly | Asn | Ser | Ile | Gly | Leu | Ser | His | His | Ser | Ala |
| | | | 340 | | | | | 345 | | | | | 350 | | |
| Trp | Leu | Thr | Val | Leu | Glu | Ala | Leu | Glu | Glu | Arg | Pro | Ala | Val | Met | Thr |
| | | 355 | | | | | 360 | | | | | 365 | | | |
| Ser | Pro | Leu | Tyr | Leu | Glu | Ile | Ile | Ile | Tyr | Cys | Thr | Gly | Ala | Phe | Leu |
| | 370 | | | | | 375 | | | | | 380 | | | | |
| Ile | Ser | Cys | Met | Val | Gly | Ser | Val | Ile | Val | Tyr | Lys | Met | Lys | Ser | Gly |
| 385 | | | | | 390 | | | | | 395 | | | | | 400 |
| Thr | Lys | Lys | Ser | Asp | Phe | His | Ser | Gln | Met | Ala | Val | His | Lys | Leu | Ala |
| | | | | 405 | | | | | 410 | | | | | 415 | |
| Lys | Ser | Ile | Pro | Leu | Arg | Arg | Gln | Val | Thr | Val | Ser | Ala | Asp | Ser | Ser |
| | | | 420 | | | | | 425 | | | | | 430 | | |
| Ala | Ser | Met | Asn | Ser | Gly | Val | Leu | Leu | Val | Arg | Pro | Ser | Arg | Leu | Ser |
| | | 435 | | | | | 440 | | | | | 445 | | | |
| Ser | Ser | Gly | Thr | Pro | Met | Leu | Ala | Gly | Val | Ser | Glu | Tyr | Glu | Leu | Pro |
| | 450 | | | | | 455 | | | | | 460 | | | | |
| Glu | Asp | Pro | Arg | Trp | Glu | Leu | Pro | Arg | Asp | Arg | Leu | Val | Leu | Gly | Lys |
| 465 | | | | | 470 | | | | | 475 | | | | | 480 |
| Pro | Leu | Gly | Glu | Gly | Cys | Phe | Gly | Gln | Val | Val | Leu | Ala | Glu | Ala | Ile |
| | | | | 485 | | | | | 490 | | | | | 495 | |
| Gly | Leu | Asp | Lys | Asp | Lys | Pro | Asn | Arg | Val | Thr | Lys | Val | Ala | Val | Lys |
| | | | 500 | | | | | 505 | | | | | 510 | | |
| Met | Leu | Lys | Ser | Asp | Ala | Thr | Glu | Lys | Asp | Leu | Ser | Asp | Leu | Ile | Ser |
| | | 515 | | | | | 520 | | | | | 525 | | | |
| Glu | Met | Glu | Met | Met | Lys | Met | Ile | Gly | Lys | His | Lys | Asn | Ile | Ile | Asn |
| | 530 | | | | | 535 | | | | | 540 | | | | |
| Leu | Leu | Gly | Ala | Cys | Thr | Gln | Asp | Gly | Pro | Leu | Tyr | Val | Ile | Val | Glu |
| 545 | | | | | 550 | | | | | 555 | | | | | 560 |
| Tyr | Ala | Ser | Lys | Gly | Asn | Leu | Arg | Glu | Tyr | Leu | Gln | Ala | Arg | Arg | Pro |
| | | | | 565 | | | | | 570 | | | | | 575 | |
| Pro | Gly | Leu | Glu | Tyr | Cys | Tyr | Asn | Pro | Ser | His | Asn | Pro | Glu | Glu | Gln |
| | | | 580 | | | | | 585 | | | | | 590 | | |
| Leu | Ser | Ser | Lys | Asp | Leu | Val | Ser | Cys | Ala | Tyr | Gln | Val | Ala | Arg | Gly |
| | | 595 | | | | | 600 | | | | | 605 | | | |
| Met | Glu | Tyr | Leu | Ala | Ser | Lys | Lys | Cys | Ile | His | Arg | Asp | Leu | Ala | Ala |
| | 610 | | | | | 615 | | | | | 620 | | | | |
| Arg | Asn | Val | Leu | Val | Thr | Glu | Asp | Asn | Val | Met | Lys | Ile | Ala | Asp | Phe |
| 625 | | | | | 630 | | | | | 635 | | | | | 640 |
| Gly | Leu | Ala | Arg | Asp | Ile | His | His | Ile | Asp | Tyr | Tyr | Lys | Lys | Thr | Thr |
| | | | | 645 | | | | | 650 | | | | | 655 | |
| Asn | Gly | Arg | Leu | Pro | Val | Lys | Trp | Met | Ala | Pro | Glu | Ala | Leu | Phe | Asp |
| | | | 660 | | | | | 665 | | | | | 670 | | |
| Arg | Ile | Tyr | Thr | His | Gln | Ser | Asp | Val | Trp | Ser | Phe | Gly | Val | Leu | Leu |
| | | 675 | | | | | 680 | | | | | 685 | | | |

-continued

Trp Glu Ile Phe Thr Leu Gly Gly Ser Pro Tyr Pro Gly Val Pro Val
690 695 700

Glu Glu Leu Phe Lys Leu Leu Lys Glu Gly His Arg Met Asp Lys Pro
705 710 715 720

Ser Asn Cys Thr Asn Glu Leu Tyr Met Met Met Arg Asp Cys Trp His
725 730 735

Ala Val Pro Ser Gln Arg Pro Thr Phe Lys Gln Leu Val Glu Asp Leu
740 745 750

Asp Arg Ile Val Ala Leu Thr Ser Asn Gln Glu Tyr Leu Asp Leu Ser
755 760 765

Met Pro Leu Asp Gln Tyr Ser Pro Ser Phe Pro Asp Thr Arg Ser Ser
770 775 780

Thr Cys Ser Ser Gly Glu Asp Ser Val Phe Ser His Glu Pro Leu Pro
785 790 795 800

Glu Glu Pro Cys Leu Pro Arg His Pro Ala Gln Leu Ala Asn Gly Gly
805 810 815

Leu Lys Arg Arg
820

( 2 ) INFORMATION FOR SEQ ID NO:4:

( i ) SEQUENCE CHARACTERISTICS:
( A ) LENGTH: 822 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

Met Trp Ser Trp Lys Cys Leu Leu Phe Trp Ala Val Leu Val Thr Ala
1 5 10 15

Thr Leu Cys Thr Ala Arg Pro Ser Pro Thr Leu Pro Glu Gln Ala Gln
20 25 30

Pro Trp Gly Ala Pro Val Glu Val Glu Ser Phe Leu Val His Pro Gly
35 40 45

Asp Leu Leu Gln Leu Arg Cys Arg Leu Arg Asp Asp Val Gln Ser Ile
50 55 60

Asn Trp Leu Arg Asp Gly Val Gln Leu Ala Glu Ser Asn Arg Thr Arg
65 70 75 80

Ile Thr Gly Glu Glu Val Glu Val Gln Asp Ser Val Pro Ala Asp Ser
85 90 95

Gly Leu Tyr Ala Cys Val Thr Ser Ser Pro Ser Gly Ser Asp Thr Thr
100 105 110

Tyr Phe Ser Val Asn Val Ser Asp Ala Leu Pro Ser Ser Glu Asp Asp
115 120 125

Asp Asp Asp Asp Asp Ser Ser Ser Glu Glu Lys Glu Thr Asp Asn Thr
130 135 140

Lys Pro Asn Arg Met Pro Val Ala Pro Tyr Trp Thr Ser Pro Glu Lys
145 150 155 160

Met Glu Lys Lys Leu His Ala Val Pro Ala Ala Lys Thr Val Lys Phe
165 170 175

Lys Cys Pro Ser Ser Gly Thr Pro Asn Pro Thr Leu Arg Trp Leu Lys
180 185 190

Asn Gly Lys Glu Phe Lys Pro Asp His Arg Ile Gly Gly Tyr Lys Val
195 200 205

-continued

| | | | | | | | | | | | | | | | |
|---|---|---|---|---|---|---|---|---|---|---|---|---|---|---|---|
| Arg | Tyr | Ala | Thr | Trp | Ser | Ile | Ile | Met | Asp | Ser | Val | Val | Pro | Ser | Asp |
| | 210 | | | | | 215 | | | | | 220 | | | | |
| Lys | Gly | Asn | Tyr | Thr | Cys | Ile | Val | Glu | Asn | Glu | Tyr | Gly | Ser | Ile | Asn |
| 225 | | | | | 230 | | | | | 235 | | | | | 240 |
| His | Thr | Tyr | Gln | Leu | Asp | Val | Val | Glu | Arg | Ser | Pro | His | Arg | Pro | Ile |
| | | | | 245 | | | | | 250 | | | | | 255 | |
| Leu | Gln | Ala | Gly | Leu | Pro | Ala | Asn | Lys | Thr | Val | Ala | Leu | Gly | Ser | Asn |
| | | | 260 | | | | | 265 | | | | | 270 | | |
| Val | Glu | Phe | Met | Cys | Lys | Val | Tyr | Ser | Asp | Pro | Gln | Pro | His | Ile | Gln |
| | | 275 | | | | | 280 | | | | | 285 | | | |
| Trp | Leu | Lys | His | Ile | Glu | Val | Asn | Gly | Ser | Lys | Ile | Gly | Pro | Asp | Asn |
| | 290 | | | | | 295 | | | | | 300 | | | | |
| Leu | Pro | Tyr | Val | Gln | Ile | Leu | Lys | Thr | Ala | Gly | Val | Asn | Thr | Thr | Asp |
| 305 | | | | | 310 | | | | | 315 | | | | | 320 |
| Lys | Glu | Met | Glu | Val | Leu | His | Leu | Arg | Asn | Val | Ser | Phe | Glu | Asp | Ala |
| | | | | 325 | | | | | 330 | | | | | 335 | |
| Gly | Glu | Tyr | Thr | Cys | Leu | Ala | Gly | Asn | Ser | Ile | Gly | Leu | Ser | His | His |
| | | | 340 | | | | | 345 | | | | | 350 | | |
| Ser | Ala | Trp | Leu | Thr | Val | Leu | Glu | Ala | Leu | Glu | Glu | Arg | Pro | Ala | Val |
| | | 355 | | | | | 360 | | | | | 365 | | | |
| Met | Thr | Ser | Pro | Leu | Tyr | Leu | Glu | Ile | Ile | Ile | Tyr | Cys | Thr | Gly | Ala |
| | 370 | | | | | 375 | | | | | 380 | | | | |
| Phe | Leu | Ile | Ser | Cys | Met | Val | Gly | Ser | Val | Ile | Val | Tyr | Lys | Met | Lys |
| 385 | | | | | 390 | | | | | 395 | | | | | 400 |
| Ser | Gly | Thr | Lys | Lys | Ser | Asp | Phe | His | Ser | Gln | Met | Ala | Val | His | Lys |
| | | | | 405 | | | | | 410 | | | | | 415 | |
| Leu | Ala | Lys | Ser | Ile | Pro | Leu | Arg | Arg | Gln | Val | Thr | Val | Ser | Ala | Asp |
| | | | 420 | | | | | 425 | | | | | 430 | | |
| Ser | Ser | Ala | Ser | Met | Asn | Ser | Gly | Val | Leu | Leu | Val | Arg | Pro | Ser | Arg |
| | | 435 | | | | | 440 | | | | | 445 | | | |
| Leu | Ser | Ser | Ser | Gly | Thr | Pro | Met | Leu | Ala | Gly | Val | Ser | Glu | Tyr | Glu |
| | 450 | | | | | 455 | | | | | 460 | | | | |
| Leu | Pro | Glu | Asp | Pro | Arg | Trp | Glu | Leu | Pro | Arg | Asp | Arg | Leu | Val | Leu |
| 465 | | | | | 470 | | | | | 475 | | | | | 480 |
| Gly | Lys | Pro | Leu | Gly | Glu | Gly | Cys | Phe | Gly | Gln | Val | Val | Leu | Ala | Glu |
| | | | | 485 | | | | | 490 | | | | | 495 | |
| Ala | Ile | Gly | Leu | Asp | Lys | Asp | Lys | Pro | Asn | Arg | Val | Thr | Lys | Val | Ala |
| | | | 500 | | | | | 505 | | | | | 510 | | |
| Val | Lys | Met | Leu | Lys | Ser | Asp | Ala | Thr | Glu | Lys | Asp | Leu | Ser | Asp | Leu |
| | | 515 | | | | | 520 | | | | | 525 | | | |
| Ile | Ser | Glu | Met | Glu | Met | Met | Lys | Met | Ile | Gly | Lys | His | Lys | Asn | Ile |
| | 530 | | | | | 535 | | | | | 540 | | | | |
| Ile | Asn | Leu | Leu | Gly | Ala | Cys | Thr | Gln | Asp | Gly | Pro | Leu | Tyr | Val | Ile |
| 545 | | | | | 550 | | | | | 555 | | | | | 560 |
| Val | Glu | Tyr | Ala | Ser | Lys | Gly | Asn | Leu | Arg | Glu | Tyr | Leu | Gln | Ala | Arg |
| | | | | 565 | | | | | 570 | | | | | 575 | |
| Arg | Pro | Pro | Gly | Leu | Glu | Tyr | Cys | Tyr | Asn | Pro | Ser | His | Asn | Pro | Glu |
| | | | 580 | | | | | 585 | | | | | 590 | | |
| Glu | Gln | Leu | Ser | Ser | Lys | Asp | Leu | Val | Ser | Cys | Ala | Tyr | Gln | Val | Ala |
| | | 595 | | | | | 600 | | | | | 605 | | | |
| Arg | Gly | Met | Glu | Tyr | Leu | Ala | Ser | Lys | Lys | Cys | Ile | His | Arg | Asp | Leu |
| | 610 | | | | | 615 | | | | | 620 | | | | |
| Ala | Ala | Arg | Asn | Val | Leu | Val | Thr | Glu | Asp | Asn | Val | Met | Lys | Ile | Ala |

-continued 625 630 635 640

Asp Phe Gly Leu Ala Arg Asp Ile His His Ile Asp Tyr Tyr Lys Lys
645 650 655

Thr Thr Asn Gly Arg Leu Pro Val Lys Trp Met Ala Pro Glu Ala Leu
660 665 670

Phe Asp Arg Ile Tyr Thr His Gln Ser Asp Val Trp Ser Phe Gly Val
675 680 685

Leu Leu Trp Glu Ile Phe Thr Leu Gly Gly Ser Pro Tyr Pro Gly Val
690 695 700

Pro Val Glu Glu Leu Phe Lys Leu Leu Lys Glu Gly His Arg Met Asp
705 710 715 720

Lys Pro Ser Asn Cys Thr Asn Glu Leu Tyr Met Met Met Arg Asp Cys
725 730 735

Trp His Ala Val Pro Ser Gln Arg Pro Thr Phe Lys Gln Leu Val Glu
740 745 750

Asp Leu Asp Arg Ile Val Ala Leu Thr Ser Asn Gln Glu Tyr Leu Asp
755 760 765

Leu Ser Met Pro Leu Asp Gln Tyr Ser Pro Ser Phe Pro Asp Thr Arg
770 775 780

Ser Ser Thr Cys Ser Ser Gly Glu Asp Ser Val Phe Ser His Glu Pro
785 790 795 800

Leu Pro Glu Glu Pro Cys Leu Pro Arg His Pro Ala Gln Leu Ala Asn
805 810 815

Arg Gly Leu Lys Arg Arg
820

( 2 ) INFORMATION FOR SEQ ID NO:5:

( i ) SEQUENCE CHARACTERISTICS:
( A ) LENGTH: 731 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Met Trp Ser Trp Lys Cys Leu Leu Phe Trp Ala Val Leu Val Thr Ala
1 5 10 15

Thr Leu Cys Thr Ala Arg Pro Ser Pro Thr Leu Pro Glu Gln Asp Ala
20 25 30

Leu Pro Ser Ser Glu Asp Asp Asp Asp Asp Asp Asp Ser Ser Ser Glu
35 40 45

Glu Lys Glu Thr Asp Asn Thr Lys Pro Asn Pro Val Ala Pro Tyr Trp
50 55 60

Thr Ser Pro Glu Lys Met Glu Lys Lys Leu His Ala Val Pro Ala Ala
65 70 75 80

Lys Thr Val Lys Phe Lys Cys Pro Ser Ser Gly Thr Pro Asn Pro Thr
85 90 95

Leu Arg Trp Leu Glu Asn Gly Lys Glu Phe Lys Pro Asp His Arg Ile
100 105 110

Gly Gly Tyr Lys Val Arg Tyr Ala Thr Trp Ser Ile Ile Met Asp Ser
115 120 125

Val Val Pro Ser Asp Lys Gly Asn Tyr Thr Cys Ile Val Glu Asn Glu
130 135 140

Tyr Gly Ser Ile Asn His Thr Tyr Gln Leu Asp Val Val Glu Arg Ser

-continued

```
145                     150                     155                     160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys Thr Ala Gly
    210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

Gly Leu Ser His His Ser Ala Trp Leu Thr Val Leu Glu Ala Leu Glu
            260                 265                 270

Glu Arg Pro Ala Val Met Thr Ser Pro Leu Tyr Leu Glu Ile Ile Ile
        275                 280                 285

Tyr Cys Thr Gly Ala Phe Leu Ile Ser Cys Met Val Gly Ser Val Ile
    290                 295                 300

Val Tyr Lys Met Lys Ser Gly Thr Lys Lys Ser Asp Phe His Ser Gln
305                 310                 315                 320

Met Ala Val His Lys Leu Ala Lys Ser Ile Pro Leu Arg Arg Gln Val
                325                 330                 335

Thr Val Ser Ala Asp Ser Ser Ala Ser Met Asn Ser Gly Val Leu Leu
            340                 345                 350

Val Arg Pro Ser Arg Leu Ser Ser Ser Gly Thr Pro Met Leu Ala Gly
        355                 360                 365

Val Ser Glu Tyr Glu Leu Pro Glu Asp Pro Arg Trp Glu Leu Pro Arg
    370                 375                 380

Asp Arg Leu Val Leu Gly Lys Pro Leu Gly Glu Gly Cys Phe Gly Gln
385                 390                 395                 400

Val Val Leu Ala Glu Ala Ile Gly Leu Asp Lys Asp Lys Pro Asn Arg
                405                 410                 415

Val Thr Lys Val Ala Val Lys Met Leu Lys Ser Asp Ala Thr Glu Lys
            420                 425                 430

Asp Leu Ser Asp Leu Ile Ser Glu Met Glu Met Met Lys Met Ile Gly
        435                 440                 445

Lys His Lys Asn Ile Ile Asn Leu Leu Gly Ala Cys Thr Gln Asp Gly
    450                 455                 460

Pro Leu Tyr Val Ile Val Glu Tyr Ala Ser Lys Gly Asn Leu Arg Glu
465                 470                 475                 480

Tyr Leu Gln Ala Arg Arg Pro Pro Gly Leu Glu Tyr Cys Tyr Asn Pro
                485                 490                 495

Ser His Asn Pro Glu Glu Gln Leu Ser Ser Lys Asp Leu Val Ser Cys
            500                 505                 510

Ala Tyr Gln Val Ala Arg Gly Met Glu Tyr Leu Ala Ser Lys Lys Cys
        515                 520                 525

Ile His Arg Asp Leu Ala Ala Arg Asn Val Leu Val Thr Glu Asp Asn
    530                 535                 540

Val Met Lys Ile Ala Asp Phe Gly Leu Ala Arg Asp Ile His His Ile
545                 550                 555                 560

Asp Tyr Tyr Lys Lys Thr Thr Asn Gly Arg Leu Pro Val Lys Trp Met
                565                 570                 575
```

-continued

| | | | | | | | | | | | | | | | |
|---|---|---|---|---|---|---|---|---|---|---|---|---|---|---|---|
| Ala | Pro | Glu | Ala | Leu | Phe | Asp | Arg | Ile | Tyr | Thr | His | Gln | Ser | Asp | Val |
| | | | 580 | | | | | 585 | | | | | 590 | | |
| Trp | Ser | Phe | Gly | Val | Leu | Leu | Trp | Glu | Ile | Phe | Thr | Leu | Gly | Gly | Ser |
| | | 595 | | | | | 600 | | | | | 605 | | | |
| Pro | Tyr | Pro | Gly | Val | Pro | Val | Glu | Glu | Leu | Phe | Lys | Leu | Leu | Lys | Glu |
| | 610 | | | | | 615 | | | | | 620 | | | | |
| Gly | His | Arg | Met | Asp | Lys | Pro | Ser | Asn | Cys | Thr | Asn | Glu | Leu | Tyr | Met |
| 625 | | | | | 630 | | | | | 635 | | | | | 640 |
| Met | Met | Arg | Asp | Cys | Trp | His | Ala | Val | Pro | Ser | Gln | Arg | Pro | Thr | Phe |
| | | | | 645 | | | | | 650 | | | | | 655 | |
| Lys | Gln | Leu | Val | Glu | Asp | Leu | Asp | Arg | Ile | Val | Ala | Leu | Thr | Ser | Asn |
| | | | 660 | | | | | 665 | | | | | 670 | | |
| Gln | Glu | Tyr | Leu | Asp | Leu | Ser | Met | Pro | Leu | Asp | Gln | Tyr | Ser | Pro | Ser |
| | | 675 | | | | | 680 | | | | | 685 | | | |
| Phe | Pro | Asp | Thr | Arg | Ser | Ser | Thr | Cys | Ser | Ser | Gly | Glu | Asp | Ser | Val |
| | 690 | | | | | 695 | | | | | 700 | | | | |
| Phe | Ser | His | Glu | Pro | Leu | Pro | Glu | Glu | Pro | Cys | Leu | Pro | Arg | His | Pro |
| 705 | | | | | 710 | | | | | 715 | | | | | 720 |
| Ala | Gln | Leu | Ala | Asn | Gly | Gly | Leu | Lys | Arg | Arg | | | | | |
| | | | | 725 | | | | | 730 | | | | | | |

( 2 ) INFORMATION FOR SEQ ID NO:6:

( i ) SEQUENCE CHARACTERISTICS:
( A ) LENGTH: 733 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Trp | Ser | Trp | Lys | Cys | Leu | Leu | Phe | Trp | Ala | Val | Leu | Val | Thr | Ala |
| 1 | | | | 5 | | | | | 10 | | | | | 15 | |
| Thr | Leu | Cys | Thr | Ala | Arg | Pro | Ser | Pro | Thr | Leu | Pro | Glu | Gln | Asp | Ala |
| | | | 20 | | | | | 25 | | | | | 30 | | |
| Leu | Pro | Ser | Ser | Glu | Asp | Asp | Asp | Asp | Asp | Asp | Asp | Ser | Ser | Ser | Glu |
| | | 35 | | | | | 40 | | | | | 45 | | | |
| Glu | Lys | Glu | Thr | Asp | Asn | Thr | Lys | Pro | Asn | Arg | Met | Pro | Val | Ala | Pro |
| | 50 | | | | | 55 | | | | | 60 | | | | |
| Tyr | Trp | Thr | Ser | Pro | Glu | Lys | Met | Glu | Lys | Lys | Leu | His | Ala | Val | Pro |
| 65 | | | | | 70 | | | | | 75 | | | | | 80 |
| Ala | Ala | Lys | Thr | Val | Lys | Phe | Lys | Cys | Pro | Ser | Ser | Gly | Thr | Pro | Asn |
| | | | | 85 | | | | | 90 | | | | | 95 | |
| Pro | Thr | Leu | Arg | Trp | Leu | Lys | Asn | Gly | Lys | Glu | Phe | Lys | Pro | Asp | His |
| | | | 100 | | | | | 105 | | | | | 110 | | |
| Arg | Ile | Gly | Gly | Tyr | Lys | Val | Arg | Tyr | Ala | Thr | Trp | Ser | Ile | Ile | Met |
| | | 115 | | | | | 120 | | | | | 125 | | | |
| Asp | Ser | Val | Val | Pro | Ser | Asp | Lys | Gly | Asn | Tyr | Thr | Cys | Ile | Val | Glu |
| | 130 | | | | | 135 | | | | | 140 | | | | |
| Asn | Glu | Tyr | Gly | Ser | Ile | Asn | His | Thr | Tyr | Gln | Leu | Asp | Val | Val | Glu |
| 145 | | | | | 150 | | | | | 155 | | | | | 160 |
| Arg | Ser | Pro | His | Arg | Pro | Ile | Leu | Gln | Ala | Gly | Leu | Pro | Ala | Asn | Lys |
| | | | | 165 | | | | | 170 | | | | | 175 | |
| Thr | Val | Ala | Leu | Gly | Ser | Asn | Val | Glu | Phe | Met | Cys | Lys | Val | Tyr | Ser |
| | | | 180 | | | | | 185 | | | | | 190 | | |

-continued

| | | | | | | | | | | | | | | | |
|---|---|---|---|---|---|---|---|---|---|---|---|---|---|---|---|
| Asp | Pro | Gln | Pro | His | Ile | Gln | Trp | Leu | Lys | His | Ile | Glu | Val | Asn | Gly |
| | | 195 | | | | | 200 | | | | | 205 | | | |
| Ser | Lys | Ile | Gly | Pro | Asp | Asn | Leu | Pro | Tyr | Val | Gln | Ile | Leu | Lys | Thr |
| | 210 | | | | | 215 | | | | | 220 | | | | |
| Ala | Gly | Val | Asn | Thr | Thr | Asp | Lys | Glu | Met | Glu | Val | Leu | His | Leu | Arg |
| 225 | | | | | 230 | | | | | 235 | | | | | 240 |
| Asn | Val | Ser | Phe | Glu | Asp | Ala | Gly | Glu | Tyr | Thr | Cys | Leu | Ala | Gly | Asn |
| | | | | 245 | | | | | 250 | | | | | 255 | |
| Ser | Ile | Gly | Leu | Ser | His | His | Ser | Ala | Trp | Leu | Thr | Val | Leu | Glu | Ala |
| | | | 260 | | | | | 265 | | | | | 270 | | |
| Leu | Glu | Glu | Arg | Pro | Ala | Val | Met | Thr | Ser | Pro | Leu | Tyr | Leu | Glu | Ile |
| | | 275 | | | | | 280 | | | | | 285 | | | |
| Ile | Ile | Tyr | Cys | Thr | Gly | Ala | Phe | Leu | Ile | Ser | Cys | Met | Val | Gly | Ser |
| | 290 | | | | | 295 | | | | | 300 | | | | |
| Val | Ile | Val | Tyr | Lys | Met | Lys | Ser | Gly | Thr | Lys | Lys | Ser | Asp | Phe | His |
| 305 | | | | | 310 | | | | | 315 | | | | | 320 |
| Ser | Gln | Met | Ala | Val | His | Lys | Leu | Ala | Lys | Ser | Ile | Pro | Leu | Arg | Arg |
| | | | | 325 | | | | | 330 | | | | | 335 | |
| Gln | Val | Thr | Val | Ser | Ala | Asp | Ser | Ser | Ala | Ser | Met | Asn | Ser | Gly | Val |
| | | | 340 | | | | | 345 | | | | | 350 | | |
| Leu | Leu | Val | Arg | Pro | Ser | Arg | Leu | Ser | Ser | Ser | Gly | Thr | Pro | Met | Leu |
| | | 355 | | | | | 360 | | | | | 365 | | | |
| Ala | Gly | Val | Ser | Glu | Tyr | Glu | Leu | Pro | Glu | Asp | Pro | Arg | Trp | Glu | Leu |
| | 370 | | | | | 375 | | | | | 380 | | | | |
| Pro | Arg | Asp | Arg | Leu | Val | Leu | Gly | Lys | Pro | Leu | Gly | Glu | Gly | Cys | Phe |
| 385 | | | | | 390 | | | | | 395 | | | | | 400 |
| Gly | Gln | Val | Val | Leu | Ala | Glu | Ala | Ile | Gly | Leu | Asp | Lys | Asp | Lys | Pro |
| | | | | 405 | | | | | 410 | | | | | 415 | |
| Asn | Arg | Val | Thr | Lys | Val | Ala | Val | Lys | Met | Leu | Lys | Ser | Asp | Ala | Thr |
| | | | 420 | | | | | 425 | | | | | 430 | | |
| Glu | Lys | Asp | Leu | Ser | Asp | Leu | Ile | Ser | Glu | Met | Glu | Met | Met | Lys | Met |
| | | 435 | | | | | 440 | | | | | 445 | | | |
| Ile | Gly | Lys | His | Lys | Asn | Ile | Ile | Asn | Leu | Leu | Gly | Ala | Cys | Thr | Gln |
| | 450 | | | | | 455 | | | | | 460 | | | | |
| Asp | Gly | Pro | Leu | Tyr | Val | Ile | Val | Glu | Tyr | Ala | Ser | Lys | Gly | Asn | Leu |
| 465 | | | | | 470 | | | | | 475 | | | | | 480 |
| Arg | Glu | Tyr | Leu | Gln | Ala | Arg | Arg | Pro | Pro | Gly | Leu | Glu | Tyr | Cys | Tyr |
| | | | | 485 | | | | | 490 | | | | | 495 | |
| Asn | Pro | Ser | His | Asn | Pro | Glu | Glu | Gln | Leu | Ser | Ser | Lys | Asp | Leu | Val |
| | | | 500 | | | | | 505 | | | | | 510 | | |
| Ser | Cys | Ala | Tyr | Gln | Val | Ala | Arg | Gly | Met | Glu | Tyr | Leu | Ala | Ser | Lys |
| | | 515 | | | | | 520 | | | | | 525 | | | |
| Lys | Cys | Ile | His | Arg | Asp | Leu | Ala | Ala | Arg | Asn | Val | Leu | Val | Thr | Glu |
| | 530 | | | | | 535 | | | | | 540 | | | | |
| Asp | Asn | Val | Met | Lys | Ile | Ala | Asp | Phe | Gly | Leu | Ala | Arg | Asp | Ile | His |
| 545 | | | | | 550 | | | | | 555 | | | | | 560 |
| His | Ile | Asp | Tyr | Tyr | Lys | Lys | Thr | Thr | Asn | Gly | Arg | Leu | Pro | Val | Lys |
| | | | | 565 | | | | | 570 | | | | | 575 | |
| Trp | Met | Ala | Pro | Glu | Ala | Leu | Phe | Asp | Arg | Ile | Tyr | Thr | His | Gln | Ser |
| | | | 580 | | | | | 585 | | | | | 590 | | |
| Asp | Val | Trp | Ser | Phe | Gly | Val | Leu | Leu | Trp | Glu | Ile | Phe | Thr | Leu | Gly |
| | | 595 | | | | | 600 | | | | | 605 | | | |

-continued

Gly Ser Pro Tyr Pro Gly Val Pro Val Glu Glu Leu Phe Lys Leu Leu
610 615 620

Lys Glu Gly His Arg Met Asp Lys Pro Ser Asn Cys Thr Asn Glu Leu
625 630 635 640

Tyr Met Met Met Arg Asp Cys Trp His Ala Val Pro Ser Gln Arg Pro
645 650 655

Thr Phe Lys Gln Leu Val Glu Asp Leu Asp Arg Ile Val Ala Leu Thr
660 665 670

Ser Asn Gln Glu Tyr Leu Asp Leu Ser Met Pro Leu Asp Gln Tyr Ser
675 680 685

Pro Ser Phe Pro Asp Thr Arg Ser Ser Thr Cys Ser Ser Gly Glu Asp
690 695 700

Ser Val Phe Ser His Glu Pro Leu Pro Glu Glu Pro Cys Leu Pro Arg
705 710 715 720

His Pro Ala Gln Leu Ala Asn Gly Gly Leu Lys Arg Arg
725 730

( 2 ) INFORMATION FOR SEQ ID NO:7:

( i ) SEQUENCE CHARACTERISTICS:
( A ) LENGTH: 302 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:7:

Met Trp Ser Trp Lys Cys Leu Leu Phe Trp Ala Val Leu Val Thr Ala
1 5 10 15

Thr Leu Cys Thr Ala Arg Pro Ser Pro Thr Leu Pro Glu Gln Asp Ala
20 25 30

Leu Pro Ser Ser Glu Asp Asp Asp Asp Asp Asp Asp Ser Ser Ser Glu
35 40 45

Glu Lys Glu Thr Asp Asn Thr Lys Pro Asn Pro Asn Pro Val Ala Pro
50 55 60

Tyr Trp Thr Ser Pro Glu Lys Met Glu Lys Lys Leu His Ala Val Pro
65 70 75 80

Ala Ala Lys Thr Val Lys Phe Lys Cys Pro Ser Ser Gly Thr Pro Asn
85 90 95

Pro Thr Leu Arg Trp Leu Lys Asn Gly Lys Glu Phe Lys Pro Asp His
100 105 110

Arg Ile Gly Gly Tyr Lys Val Arg Tyr Ala Thr Trp Ser Ile Ile Met
115 120 125

Asp Ser Val Val Pro Ser Asp Lys Gly Asn Tyr Thr Cys Ile Val Glu
130 135 140

Asn Glu Tyr Gly Ser Ile Asn His Thr Tyr Gln Leu Asp Val Val Glu
145 150 155 160

Arg Ser Pro His Arg Pro Ile Leu Gln Ala Gly Leu Pro Ala Asn Lys
165 170 175

Thr Val Ala Leu Gly Ser Asn Val Glu Phe Met Cys Lys Val Tyr Ser
180 185 190

Asp Pro Gln Pro His Ile Gln Trp Leu Lys His Ile Glu Val Asn Gly
195 200 205

Ser Lys Ile Gly Pro Asp Asn Leu Pro Tyr Val Gln Ile Leu Lys Val
210 215 220

-continued

Ile Met Ala Pro Val Phe Val Gly Gln Ser Thr Gly Lys Glu Thr Thr
225 230 235 240

Val Ser Gly Ala Gln Val Pro Val Gly Arg Leu Ser Cys Pro Arg Met
245 250 255

Gly Ser Phe Leu Thr Leu Gln Ala His Thr Leu His Leu Ser Arg Asp
260 265 270

Leu Ala Thr Ser Pro Arg Thr Ser Asn Arg Gly His Lys Val Glu Val
275 280 285

Ser Trp Glu Gln Arg Ala Ala Gly Met Gly Gly Ala Gly Leu
290 295 300

( 2 ) INFORMATION FOR SEQ ID NO:8:

( i ) SEQUENCE CHARACTERISTICS:
( A ) LENGTH: 302 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Met Trp Ser Trp Lys Cys Leu Leu Phe Trp Ala Val Leu Val Thr Ala
1 5 10 15

Thr Leu Cys Thr Ala Arg Pro Ser Pro Thr Leu Pro Glu Gln Asp Ala
20 25 30

Leu Pro Ser Ser Glu Asp Asp Asp Asp Asp Asp Asp Ser Ser Ser Glu
35 40 45

Glu Lys Glu Thr Asp Asn Thr Lys Pro Asn Arg Met Pro Val Ala Pro
50 55 60

Tyr Trp Thr Ser Pro Glu Lys Met Glu Lys Lys Leu His Ala Val Pro
65 70 75 80

Ala Ala Lys Thr Val Lys Phe Lys Cys Pro Ser Ser Gly Thr Pro Asn
85 90 95

Pro Thr Leu Arg Trp Leu Lys Asn Gly Lys Glu Phe Lys Pro Asp His
100 105 110

Arg Ile Gly Gly Tyr Lys Val Arg Tyr Ala Thr Trp Ser Ile Ile Met
115 120 125

Asp Ser Val Val Pro Ser Asp Lys Gly Asn Tyr Thr Cys Ile Val Glu
130 135 140

Asn Glu Tyr Gly Ser Ile Asn His Thr Tyr Gln Leu Asp Val Val Glu
145 150 155 160

Arg Ser Pro His Arg Pro Ile Leu Gln Ala Gly Leu Pro Ala Asn Lys
165 170 175

Thr Val Ala Leu Gly Ser Asn Val Glu Phe Met Cys Lys Val Tyr Ser
180 185 190

Asp Pro Gln Pro His Ile Gln Trp Leu Lys His Ile Glu Val Asn Gly
195 200 205

Ser Lys Ile Gly Pro Asp Asn Leu Pro Tyr Val Gln Ile Leu Lys Val
210 215 220

Ile Met Ala Pro Val Phe Val Gly Gln Ser Thr Gly Lys Glu Thr Thr
225 230 235 240

Val Ser Gly Ala Gln Val Pro Val Gly Arg Leu Ser Cys Pro Arg Met
245 250 255

Gly Ser Phe Leu Thr Leu Gln Ala His Thr Leu His Leu Ser Arg Asp
260 265 270

-continued

Leu Ala Thr Ser Pro Arg Thr Ser Asn Arg Gly His Lys Val Glu Val
275 280 285

Ser Trp Glu Gln Arg Ala Ala Gly Met Gly Gly Ala Gly Leu
290 295 300

( 2 ) INFORMATION FOR SEQ ID NO:9:

( i ) SEQUENCE CHARACTERISTICS:
( A ) LENGTH: 961 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CGCCAACTGG CTCCTTACCG TCACACTCTC ATCGTGCCGC AGACTTGATG TGCCGCCGCC 60

CGGATTGCGG CTTCTCTTTC TCACCTGGAC CGGTGGCACT GCTGTGGTGT TGCCTTCTGC 120

TGCCCATCGT TTCCTCAGCC ACCGTCAGCG TCGCTCCTAC CGTCGCCGAG AAAGTTCCCG 180

CGGAGTGCCC CGAACTAACG CGTCGATGCC TGTTGGGTGA GGTGTTTCAG GGTGACAAGT 240

ATGAAAGTTG GCTGCGCCCG TTGGTGAATG TTACCAGACG CGATGGCCCG CTATCGCAAC 300

TTATTCGTTA CCGTCCCGTT ACGCCGGAGG CCGCCAACTC CGTGCTGTTG GACGATGCTT 360

TCCTGGACAC TCTGGCCCTG CTGTACAACA ATCCGGATCA ATTGCGGGCC TTGCTGACGC 420

TGTTGAGCTC GGACACAGCG CCGCGCTGGA TGACGGTGAT GCGCGGTTAC AGCGAGTGCG 480

GCGATGGCTC GCCGGCCGTG TACACGTGCG TGGACGACCT GTGCCGCGGC TACGACCTCA 540

CGCGACTGTC ATACGGGCGC AGCATCTTCA CGGAACACGT GTTAGGCTTC GAGCTGGTGC 600

CACCGTCTCT CTTTAACGTG GTGGTGGCCA TACGCAACGA AGCCACGCGT ACCAACCGCG 660

CCGTGCGTCT GCCCGTGAGC ACCGCTGCCG CGCCCGAGGG CATCACGCTC TTTTACGGCC 720

TGTACAACGC AGTGAAGGAA TTCTGCCTGC GTCACCAGCT GGACCCGCCG CTGCTACGCC 780

ACCTAGATAA ATACTACGCC GGACTGCCGC CCGAGCTGAA GCAGACGCGC GTCAACCTGC 840

CGGCTCACTC GCGCTATGGC CCTCAAGCAG TGGATGCTCG CTAACATTGC TGATAATAAA 900

GGCTCTCTGT TAACCCCCGA CGAGCAGGCT CGCGTGTTTT GTCTGAGCGC CGACTGGATC 960

C 961

( 2 ) INFORMATION FOR SEQ ID NO:10:

( i ) SEQUENCE CHARACTERISTICS:
( A ) LENGTH: 278 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

Met Cys Arg Arg Pro Asp Cys Gly Phe Ser Phe Ser Pro Gly Pro Val
1 5 10 15

Ala Leu Leu Trp Cys Cys Leu Leu Leu Pro Ile Val Ser Ser Ala Thr
20 25 30

Val Ser Val Ala Pro Thr Val Ala Glu Lys Val Pro Ala Glu Cys Pro
35 40 45

Glu Leu Thr Arg Arg Cys Leu Leu Gly Glu Val Phe Gln Gly Asp Lys
50 55 60

Tyr Glu Ser Trp Leu Arg Pro Leu Val Asn Val Thr Arg Arg Asp Gly

-continued 65 70 75 80

Pro Leu Ser Gln Leu Ile Arg Tyr Arg Pro Val Thr Pro Glu Ala Ala
85 90 95

Asn Ser Val Leu Leu Asp Asp Ala Phe Leu Asp Thr Leu Ala Leu Leu
100 105 110

Tyr Asn Asn Pro Asp Gln Leu Arg Ala Leu Leu Thr Leu Leu Ser Ser
115 120 125

Asp Thr Ala Pro Arg Trp Met Thr Val Met Arg Gly Tyr Ser Glu Cys
130 135 140

Gly Asp Gly Ser Pro Ala Val Tyr Thr Cys Val Asp Asp Leu Cys Arg
145 150 155 160

Gly Tyr Asp Leu Thr Arg Leu Ser Tyr Gly Arg Ser Ile Phe Thr Glu
165 170 175

His Val Leu Gly Phe Glu Leu Val Pro Pro Ser Leu Phe Asn Val Val
180 185 190

Val Ala Ile Arg Asn Glu Ala Thr Arg Thr Asn Arg Ala Val Arg Leu
195 200 205

Pro Val Ser Thr Ala Ala Ala Pro Glu Gly Ile Thr Leu Phe Tyr Gly
210 215 220

Leu Tyr Asn Ala Val Lys Glu Phe Cys Leu Arg His Gln Leu Asp Pro
225 230 235 240

Pro Leu Leu Arg His Leu Asp Lys Tyr Tyr Ala Gly Leu Pro Pro Glu
245 250 255

Leu Lys Gln Thr Arg Val Asn Leu Pro Ala His Ser Arg Tyr Gly Pro
260 265 270

Gln Ala Val Asp Ala Arg
275

( 2 ) INFORMATION FOR SEQ ID NO:11:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

Met Gly Ser Arg Gly Ser Val Asp Leu Asp Lys
1 5 10

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:12:

Leu Glu Asp Pro Ser Thr
1 5

( 2 ) INFORMATION FOR SEQ ID NO:13:

( i ) SEQUENCE CHARACTERISTICS:
( A ) LENGTH: 30 base pairs
( B ) TYPE: nucleic acid -continued ( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

ATAACGGACC TTGTAGCCTC CAATTCTGTG 30

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

GCGGCGTTTG AGTCCGCCAT TGGCAAGCTG 30

( 2 ) INFORMATION FOR SEQ ID NO:15:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

CCAACCTCTA GAGGATCCAC TGGGATGTGG AGCTGGAAGT GC 42

( 2 ) INFORMATION FOR SEQ ID NO:16:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GTAAGCGGCC GCGGATCCTT ACTACTCCAG GTACAGGGGC GA 42

( 2 ) INFORMATION FOR SEQ ID NO:17:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CCATTTGGAT CCGTCACAGC CACACTCTGC ACCGCT 36

( 2 ) INFORMATION FOR SEQ ID NO:18:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:18:

CCATTTGTC GACTTCCATC TTTTCTGGGGA TGTCCA 36

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GGATCCGCTA GCAGGCCGTC CCCGACCTTG 30

( 2 ) INFORMATION FOR SEQ ID NO:20:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GGATCCAAGC TTTTACTCCA GGTACAGGGG CGA 33

METHOD OF PRODUCING SECRETED CMV GLYCOPROTEIN H

BACKGROUND OF THE INVENTION

1. Technical Field

The present invention relates generally to recombinant production of proteins. More particularly, the invention relates to methods for facilitating egress of recombinantly produced proteins from a host cell using escorts, 2. Background of the Invention A desirable method for the production of proteins involves recombinant expression. However, commercially useful quantities of proteins can be difficult to obtain. This is particularly true with viral glycoproteins where recombinant production does not always mimic expression during viral infection. Specifically, some viral proteins are expressed at the cell surface during viral infection but are expressed intracellularly in recombinant systems. Thus, additional purification steps must be taken in order to isolate the proteins. Additionally, the proteins are susceptible to degradation by intracellular enzymes prior to purification. Such intracellular expression has been observed in herpesvirus systems with respect to glycoprotein H (gH) expression (Gompels and Minson, *J. Virol.* (1989) 63:4744–4755); spaete et al., *Progress in Cytomegalovirus Research.* (M. P. Landini, ed., 1991) pp. 133–136).

Chaperones bind newly synthesized polypeptides and appear to stabilize these polypeptides until they are assembled into their proper native structure or until they are transported to another cellular compartment, i.e., for secretion. Sambrook and Gething, *Nature* (1989) 342:224–225. Gompels and Minson, supra, postulate that additional virus gene products are required for transport of herpes simplex virus type 1 (HSV-1) gH through the endoplasmic reticulum-Golgi network to the cell surface. Similarly, the existence of a viral function which escorts cytomegalovirus (CMV) gH to the cell surface was proposed in Spaete et al., supra. However, CMV UL56, the homologue of herpesvirus ICP18.5 which has been implicated in the egress of viral glycoproteins to the cell surface (Pancake et al., *J. Virol.* (1983) 47:568–585), failed to promote movement of both truncated and full-length forms of CMV gH to the cell surface.

As with gH, cell lines transfected with the gene encoding the human immunodeficiency virus (HIV) type 1 envelope glycoprotein, gp 160, have also failed to process or export the protein. Haffar et al., *J. Virol.* (1990) 63:3100–3103, speculated that this was due to the absence of other viral proteins during recombinant production.

A new HSV glycoprotein, gL, has now been identified (Hutchinson et al., *J. Virol.* (1992) 66:2240–2250, and Hutchinson et al., Abstract, XVI International Herpesvirus Workshop, Jul. 7–12, 1991). This protein is encoded by the UL1 gene of HSV-1. Like gH, gL is not properly processed when expressed in the absence of other HSV polypeptides. However, when HSV gL and HSV gH are coexpressed, the proteins are antigenically similar to those found in infected cells and the proteins are processed and transported to the cell surface. The experimenters postulated that formation of an HSV gL/gH complex was therefore a prerequisite for the processing and transport of both molecules. However, the use of a gL/gH complex as a tool for increasing the recombinant expression of either of the proteins was not addressed.

The fibroblast growth factors (FGFs) are a family of structurally related polypeptides that regulate the growth and differentiation of a diverse number of cell types. Currently, seven distinct gene products have been identified. These include acidic and basic FGFs (Jaye et al., *Science* (1986) 233:541–545; Abraham et al., *Science* (1986) 233:545–548; Abraham et al., *EMBO J* (1986) 5:2523–2528), the product of the int-2 oncogene (Moore et al., *EMBO J* (1986) 5:919–924; Jakobovits et al., *Proc. Natl. Acad. Sci. USA* (1986) 83:7806–7810), a growth factor identified from Kaposi's sarcoma DNA, known as hst-1 or KS-FGF (Bovi et al., *Cell* (1987) 50:729–737; Taira et al., *Proc. Natl. Acad. Sci. USA* (1987) 84:2980–2984), FGF-5 (Zahn et al., *Mol. Cell. Biol.* (1988) 8:3487–3495), FGF-6 (Marics et al., *Oncogene* (1989) 4:335–340) and keratinocyte growth factor, KGF or FGF-7 (Finch et al., *Science* (1989) 245:752–755.

FGF receptors appear to mediate the effects of the various FGFs on cells. Two classes of receptors have been identified for the acidic and basic FGFs and a number of FGF receptors have now been cloned. See, e.g., Kaner et al., *Science* (1990) 248:1410–1413; Mansukhani et al., *Proc. Natl. Acad. Sci. USA* (1990) 87:4378–4382; Dionne et al., *EMBO J* (1990) 9:2685–2692; Mirda and Williams, *Clin. Res.* (1990) 38:310A; and Kiefer et al., *Growth Factors* (1991) 5:115–127. Kiefer et al., supra, cloned an FGF receptor from a human cell line cDNA library. The cDNA encodes a three-immunoglobulin like-domain FGF receptor and is capable of binding both acidic and basic FGFs. A soluble, extracellular domain form of this FGF receptor was produced in a baculovirus expression system and termed EC-FGF.

An FGF receptor has been implicated as a cellular receptor for HSV-1 (Kaner et al., *Science* (1990) 248:1410–1413). The initial HSV-1 virion attachment to cells requires an interaction with heparin like cell associated glycosaminoglycans and may be mediated by HSV envelope glycoproteins gB and gC. WuDunn and Spear, *J. Virol.* (1989) 63:52–58. gB and gD are essential for the secondary interactions at the cell surface that lead to virus entry into cells (Cai et al., *J. Virol.* (1988) 62:2596–2604; Fuller and Spear *Proc. Natl. Acad. Sci. USA* (1987) 84:5454–5458; Ligas and Johnson *J. Virol.* (1988) 62:1486–1494; Johnson et al., *J. Virol.* (1990) 64:2569–2576), and gH is probably also involved in the viral penetration (Fuller et al., *J. Virol.* (1989) 63:3435–3443). The use of an FGF receptor as an escort for increasing recombinant expression of a desired protein has not heretofore been suggested.

DISCLOSURE OF THE INVENTION

The present invention is based on the discovery that escort proteins can significantly enhance the expression of viral glycoproteins at the cell surface. Accordingly, proteins are secreted from the transformed cell, thereby dramatically increasing protein yields without further extensive manipulation and purification required.

Accordingly, in one embodiment, the present invention is directed to a method for recombinantly producing a protein comprising coexpressing in a host cell a first gene encoding the protein with a second gene encoding an escort, under conditions whereby the protein is secreted from the host cell.

In still another embodiment, the invention is directed to a method for recombinantly producing CMV gH comprising coexpressing in a host cell a first gene encoding the gH with a second gene encoding soluble FGF receptor, under conditions whereby the gH is secreted from the host cell.

In another embodiment, the subject invention is directed to a method for recombinantly producing an immunologically reactive truncated CMV gH wherein the truncated gH lacks all or a portion of a transmembrane binding domain which is present in native human CMV gH. The method comprises coexpressing in a host cell a first gene encoding the truncated gH with a second gene encoding soluble FGF receptor, under conditions whereby the truncated gH is secreted from the host cell.

In yet another embodiment, the invention is directed to a method for recombinantly producing CMV gH comprising coexpressing in a host cell a first gene encoding the gH with a second gene encoding UL115, under conditions whereby the gH is secreted from the host cell.

In another embodiment, the subject invention is directed to a method for recombinantly producing an immunologically reactive truncated CMV gH wherein the truncated gH lacks all or a portion of a transmembrane binding domain which is present in native human CMV gH, the method comprising coexpressing in a host cell a first gene encoding the truncated gH with a second gene encoding UL115, under conditions whereby the truncated gH is secreted from the host cell.

In still another embodiment, the invention pertains to a complex comprising a recombinant, immunologically reactive herpesvirus polypeptide and an escort.

These and other embodiments of the subject invention will readily occur to those of skill in the art in light of the disclosure herein.

BRIEF DESCRIPTION OF THE DRAWINGS

FIGS. 1A–1G depict (SEQ. ID NO:1) and (SEQ. ID NO:2) is the nucleotide sequence of the CMV Towne gH gene. The DNA sequence and the predicted amino acid sequence are shown. The putative TATA, CAT and polyadenylation sequences have been underlined. Potential N-linked glycosylation sites are overlined and the predicted signal sequence and transmembrane domain are boxed. The locations of p86 tryptic peptides used in the initial identification of gH are indicated by the broken lines ($Gln_{354}$ to $Pro_{364}$ and $Gln_{370}$ to $Gln_{377}$).

FIGS. 6A–6B (SEQ. ID NO:3), (SEQ. ID NO:4), (SEQ. ID NO:5), (SEQ. ID NO:6), (SEQ. ID NO:7), and (SEQ. ID NO:8) depict an amino acid sequence comparison of the six different human FGF receptor forms. Sequences have been aligned for maximum identity and those that differ or are deleted have been boxed. Various domains (abbreviations as in FIG. 5) and regions used for PCR primers (P1–P4) are indicated above sequence 1 (flg5). The putative signal peptidase cleavage site is also indicated (↓). Sequence 2 was from A. Isacchi et al., *Nucleic Acids Res.* (1990) 18:1906, and sequences 3–6 were from D. E. Johnson et al., *Mol. Cell. Biol.* (1990) 10:4728–4736.

FIG. 7 (SEQ. ID NO:9) and (SEQ. ID NO:10) is a comparison of the nucleotide sequence of the UL115 open reading frame (ORF) from CMV strain Towne with strain AD169. The Towne sequence is shown in its entirety along with the predicted single letter amino acid code translation product. Nucleotide differences in the AD169 strain sequence are shown above the Towne sequence in lower case letters. Asterisked base changes indicate those changes that result in an amino acid change in the AD169 gene product.

DETAILED DESCRIPTION OF THE INVENTION

Figure 2:
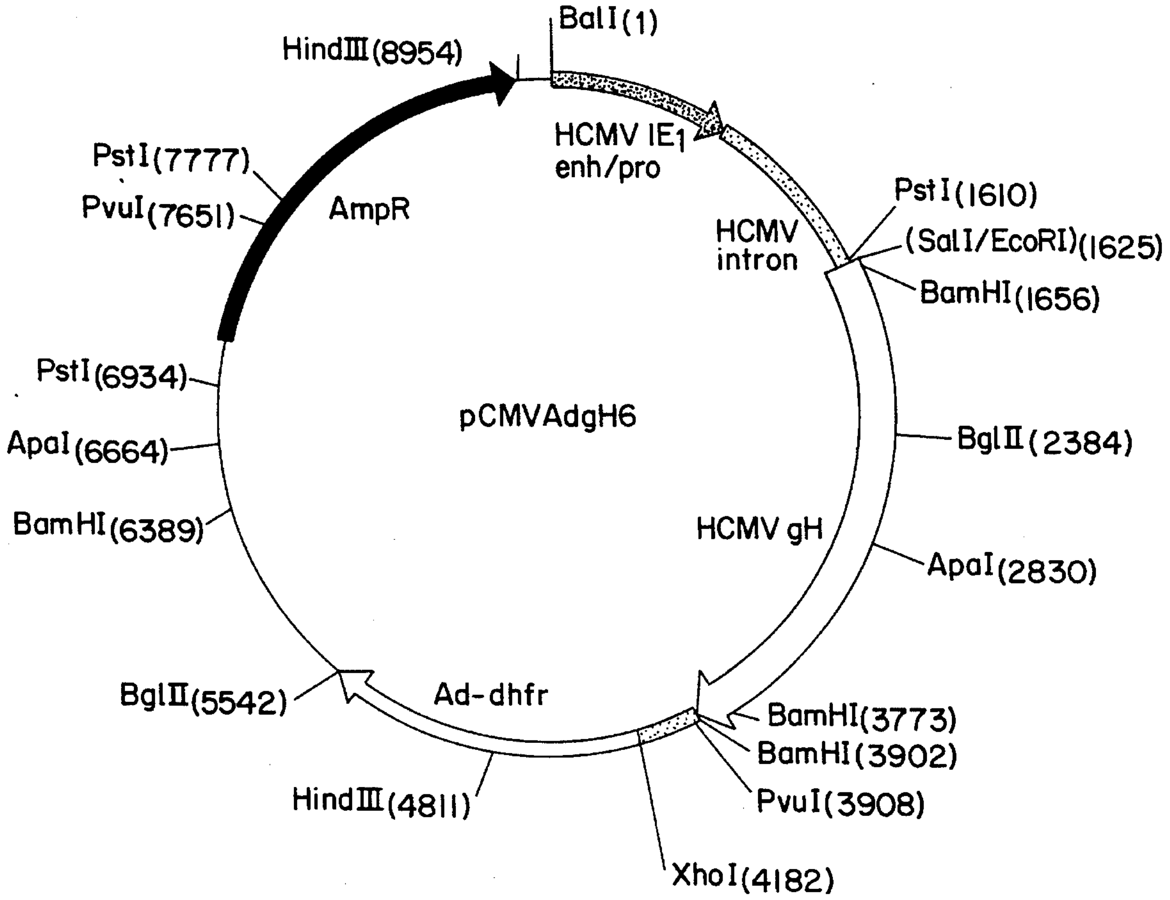
FIG. 2 is a diagram of pCMAdgH6, a CMV gH mammalian expression vector encoding a truncated gH gene.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like.

A polypeptide is "immunologically reactive" when it includes one or more epitopes and thus elicits antibodies that neutralize infectivity, and/or mediate antibody-complement or antibody dependent cell cytotoxicity to provide protection to an immunized host. Immunological reactivity may be determined in a standard immunoassay, such as a competition assay, as is known in the art.

A "fragment" of a reference polypeptide is any contiguous amino acid sequence found in the reference polypeptide. Such fragments will usually be at least 5 amino acids in length, preferably at least about 10 to 15 amino acids in length. There is no critical upper limit to the length of the fragment which could comprise nearly the full-length of the protein sequence or even a fusion protein. Preferably, the fragment encodes an epitope from the polypeptide, most preferably a neutralizing epitope. A first polypeptide comprises a fragment of another polypeptide even if the homologous domain in the first polypeptide is flanked by amino acid sequences which are not fragments of the other polypeptide.

The term "escort" as used herein is defined functionally as any compound capable of associating with a protein coexpressed therewith, thereby facilitating transport of the protein to the cell surface where the protein can be secreted. By way of example, the soluble human FGF receptor and CMV UL115 have been found to be capable of forming complexes with CMV gH, thereby aiding egress of the gH through the host cell. Similarly, HSV gL has been shown to form a complex with HSV gH such that the two proteins can be transported to the cell surface for secretion. Accordingly, these molecules are considered "escorts" in the context of the present invention. It is not necessary that the full-length protein be present in order to serve an escort function. Indeed, the soluble FGF receptor is a truncated molecule having only the extracellular domain (described further below). Other escorts and proteins with which they interact are described more fully below.

"Cytomegalovirus gH or CMV gH polypeptide" refers to a polypeptide comprising a fragment of native human CMV gH. Thus, the term includes both polypeptides comprising the native sequence of gH (full-length and truncated), as well as analogs thereof. Preferred analogs are those which are substantially homologous to the corresponding native amino acid sequence, and most preferably encode at least one native gH epitope, such as a neutralizing epitope. A particularly preferred class of CMV gH polypeptides are truncated molecules lacking a sufficient portion of the C-terminal transmembrane domain, to promote efficient expression and/or secretion of the CMV gH polypeptide at high levels from the host cell. It is believed that about 25 C-terminal amino acid residues (residues 718 to 742 of strain Towne, FIGS. 1A–1G) comprise the transmembrane domain, but other regions may also be critical to transmembrane binding. Deletions of all or parts of such domains that eliminate or substantially decrease transmembrane binding, as well as sequences adjacent to these domains are desired. Typically, at least about 5 amino acids will be deleted, preferably at least about 10 residues, and most preferably from at least about 20 residues to 34 residues will be deleted from the C-terminus of the native sequence. Examples of such deletions from one strain are the residues numbered in FIGS. 1A–1G, 732 to 742, 722 to 742, 720 to 742, 718 to 742 and 712 to 742. Of course, other functional deletions can be readily defined by those of ordinary skill by constructing and screening deletions from the same or other domains by expressing the polypeptides in host cells. The only true upper limit to the deletions is the practical limitations of retaining useful epitopes (e.g., neutralizing epitopes). Typically, however, the deletions will not constitute more than about 100 amino acids of the native gH sequence, particularly the 100 C-terminal residues. It should also be understood that "deletion" of a portion of a transmembrane domain means only that the particular native amino acid sequences do not appear in the polypeptide, and that other amino acids (such as hydrophilic residues) can be substituted for the deleted residues.

The term "gL" refers to the gene product of the UL10RF of HSV. The gene encoding HSV-1 gL has been previously described. McGeoch et al., *J. Gen. Virol.* (1988) 69:1531–1574. Nucleotide sequence analysis predicts a protein of 224 amino acids with a putative signal sequence and a single site for attachment of N-linked oligosaccharides. The HSV-1 gL protein appears to exist as a 30 kDa precursor form and a 40 kDa mature form. For a further description of HSV-1 gL, see, Hutchinson et al., *J. Virol.* (1992) 66:2240–2250, and Hutchinson et al., Abstract, XVI International Herpesvirus Workshop, Jul. 7–12, 1991. As with gH, the gL for use in the present invention may be a gL polypeptide, either the full-length molecule or an active fragment thereof. Additionally, the term encompasses analogs of the native sequence which are substantially homologous and immunologically reactive. Thus, amino acid substitutions, deletions and additions are contemplated herein that do not destroy the immunoreactivity of the protein.

By "UL115" is meant a protein substantially homologous to the gene product of the CMV UL115 ORF, which retains the escort function of the native protein. The strain Towne and AD169 CMV nucleotide sequences for full-length UL115 are depticted in FIG. 7. In both strains, the UL115 ORF is 834 bp in length and encodes a primary translation product of 278 amino acids. UL115 appears to be the CMV homologue to HSV-1 gL, which is encoded by the UL1 gene of HSV-1. (See, Hutchinson et al., *J. Virol.* (1992) 66:2240–2250, and Hutchinson et al., Abstract, XVI International Herpesvirus Workshop, Jul. 7–12, 1991, for a further discussion of HSV gL.) A "UL115 polypeptide" is a contiguous sequence of amino acids derived from UL115. The polypeptide may consist of the native sequence or may include substitutions, additions or deletions, so long as the molecule retains the ability to form complexes with a protein coexpressed therewith and escort the protein to the cell surface for secretion. The formation of such complexes can be monitored using assays such as immunoprecipitation, described further in the examples.

The term "FGF receptor" or "FGF-R" as used herein refers to the human FGF receptor or a fragment thereof which binds FGF in the presence of heparin. The FGF receptor has an amino acid sequence substantially as depicted in FIGS. 6A–6B. The term "rFGF-R" refers to active FGF-R prepared by recombinant means. A preferred form of rFGF-R is soluble rFGF-R ("sFGF-R" or "EC-FGF"), which is a truncated form obtained by expressing only the extracellular domain. It is surprisingly found that the truncated form is able to act as an escort for viral glycoproteins. The preferred sFGF-R of the invention is a 58 kDa glycoprotein which binds bFGF with a $K_d$ of 2–5 nM. As with UL115, an "FGF receptor polypeptide" is a contiguous sequence of amino acids derived from the FGF receptor which may consist of the native sequence or may include substitutions, additions or deletions, so long as the molecule retains the ability to form complexes with a protein coexpressed therewith and escort the protein to the cell surface for secretion. The formation of such complexes can be monitored using assays such as immunoprecipitation, described further in the examples.

By "HSV gH" or "HSV gH polypeptide" is meant the art-recognized gH protein from herpes simplex virus, as well as active fragments and analogs thereof. Thus, as above, the term captures amino acid substitutions, deletions and additions which do not destroy the immunoreactivity of the protein. HSV-1 gH has an apparent molecular weight of approximately 110,000 and the gene encoding this protein has been sequenced. (Gompels and Minson, *Virology* (1986) 153:230–247; McGeoch and Davison, *Nucleic Acids Res.* (1986) 14:4281–4292.) The gene has been expressed in mammalian cells. Gompels and Minson, *J. Virol.* (1989) 63:4744–4755.

The term "complex" as used herein denotes any association of an escort with a compatible protein, regardless of the nature of the association. Accordingly, the term captures molecules which are covalently bound to one another as well as those associated with each other via electrostatic and other forces. Complexes can be detected using assays such as immunoprecipitation, described in the examples.

"Operably linked" refers to a juxtaposition wherein the components so described are in a relationship permitting them to function in their intended manner. A regulatory element "operably linked" to a structural sequence is ligated in such a way that expression of the structural sequence is achieved under conditions compatible with the regulatory elements.

"Recombinant" as used herein to describe a polynucleotide means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines" "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

A "regulatory element" refers to a polynucleotide sequence which effects the expression of a coding sequence to which it is linked. The term includes promoters, terminators, and when appropriate, leader sequences and enhancers.

A "replicon" is any genetic element, e.g., plasmid, cosmid, chromosome, virus, or phage, that behaves as an autonomous unit of polynucleotide replication within a cell.

A sequence which is "substantially homologous" to a reference sequence shares at least about 50% sequence homology, preferably at least about 75%, more preferably at least about 85%, and most preferably at least about 90% to 95%. The term "substantially homologous" as used herein also includes proteins showing sequence identity to the reference sequence.

"Transformation," as used herein, refers to the insertion of an exogenous polynucleotide into a host cell, irrespective of the method used for insertion: for example, direct uptake, transduction, or f-mating. The exogenous polynucleotide may be maintained as a nonintegrated vector, for example, a plasmid, or alternatively, may be integrated into the host genome.

A "vector" is a replicon in which a heterologous polynucleotide segment is attached, so as to bring about the replication and/or expression of the attached segment, such as a plasmid, transposon, phage, etc.

"Coexpression" as used herein refers to the expression of two or more different proteins in a host cell. The polynucleotides encoding for the proteins can be harbored in a single plasmid, either under the control of the same regulatory elements or under the control of separate elements. Thus, the production of a fusion protein including active portions of the two or more protein sequences would be considered "coexpressed" for purposes of the present definition as would the expression of two genes as a dicistronic construct employing an internal ribosome entry site. Similarly, proteins expressed from the same vector but driven by separate regulatory elements, would also be considered "coexpressed." The term also refers to the expression of two or more proteins from separate constructs. Thus, the expression of proteins encoded from genes present on separate vectors in a host cell would also be considered "coexpression" for purposes of the present invention.

Modes of Carrying Out the Invention

The present invention is based on the discovery of particular escorts capable of shuttling proteins coexpressed therewith to the cell surface where the expressed products can be secreted. Protein yields are thereby increased due to facilitated egress of the proteins and purification of the expressed product can be easily accomplished. Without being bound by a particular theory, it appears that the escort allows egress from the host cell by associating with the protein, thereby providing for release of the protein from the endoplasmic reticulum. It is possible that the escort hides a retention signal and/or confers a tertiary conformation on the protein which permits such egress.

The present invention will find use with a wide variety of proteins. Indeed, almost any desired protein can be produced using a compatible escort. Thus, the invention permits increased yields of such useful products as viral and bacterial antigens for use in vaccines and diagnostics, peptide hormones and drugs for use in pharmaceuticals, and marker proteins and the like with a wide variety of uses. Antibodies raised against these proteins are also useful as diagnostics.

The present invention is particularly useful in the production of viral glycoproteins, especially those glycoproteins which are expressed intracellularly in recombinant systems. For example, the present invention will find use for the expression of a wide variety of proteins from the herpesvirus family, including proteins derived from herpes simplex virus (HSV), varicella zoster virus (VZV), Epstein-Barr virus (EBV), cytomegalovirus (CMV) and other human herpesviruses such as HHV6 and HHV7. Proteins from other viruses, such as but not limited to, proteins from the hepatitis family of viruses, including hepatitis A virus (HAV), hepatitis B virus (HBV), hepatitis C virus (HCV), the delta hepatitis virus (HDV) and hepatitis E virus (HEV), as well as retrovirus proteins such as from HTLV-I and HTLV-II and proteins from the human immunodeficiency viruses (HIVs), such as HIV-1 and HIV-2, can also be conveniently expressed using the present system. (See, e.g. Chee et al., *Cytomegaloviruses* (J. K. McDougall, ed., Springer-Verlag 1990) pp. 125–169, for a review of the protein coding content of cytomegalovirus; McGeoch et al., *J. Gen. Virol.* (1988) 69:1531–1574, for a discussion of the various HSV-1 encoded proteins; Baer et al., *Nature* (1984) 310:207–211, for the identification of protein coding sequences in an EBV genome, Davison and Scott, *J. Gen. Virol.* (1986) 67:1759–1816, for a review of VZV; Houghton et al., *Hepatology* (1991) 14:381–388, for a discussion of the HCV genome; and Sanchez-Pescador et al., *Science* (1985) 227:484–492, for an HIV genome.)

The above proteins are coexpressed with a compatible escort such that the protein of interest can be efficiently secreted from the host cell. Compatible escorts will be readily identifiable by assaying for the formation of complexes between the putative escort and the protein of interest, using known techniques such as electrophoresis and immunoprecipitation. The detection of such complexes is described further in the examples and in Hutchinson et al., *J. Virol.* (1992) 66:2240–2250.

By way of example, HSV-1 gL (encoded by the UL1 ORF) has been found to form a complex with HSV-1 gH (encoded by the UL22 ORF) (Hutchinson et al., *J. Virol.* (1992) 66:2240–2250). When gH and gL are coexpressed, they are present at the cell surface, unlike gH and gL expressed in the absence of other viral proteins. Proteins functionally and/or structurally homologous to HSV-1 gH and gL are found throughout the herpesvirus family. For instance, the EBV ORF BKRF2 encodes the EBV homologue of HSV-1 gL and ORF BXLF2 encodes the homologue for gH (termed gp85). Baer et al., *Nature* (1984) 310:207–211; Heineman et al., *J. Virol.* (1988) 62:1101–1107. Similarly, gene 60 of VZV is the VZV homologue of HSV UL1 and encodes a protein termed VZV37. Davison and Scott, *J. Gen. Virol.* (1986) 67:1759–1816, McGeoch et al., *J. Gen. Virol.* (1988) 69:1531–1574; Cranage et al., *J. Virol.* (1988) 62:1416–1422. Likewise, CMV gH (encoded by UL75) is the homologue to HSV-1 gH (Pachl et al., *Virology* (1989) 169:418–426; Cranage et al., *J. Virol.* (1988) 62:1416–1422; Chee et al., *Cytomegaloviruses* (J. K. McDougall, ed., Springer-Verlag 1990) pp. 125–169). The HHVs also encode gH (as well as other herpesvirus protein) analogs. Accordingly, glycoprotein homologues, found in other herpesviruses, are also encompassed by the present invention. Other herpesvirus glycoproteins which will be conveniently expressed using escorts include the various HSV glycoproteins, including HSV gB and HSV gD; CMV gB; and the HHV homologues to these proteins.

Of particular interest is the present discovery that CMV UL115 is the homologue of HSV gL. As described further herein, like HSV-1 gL and gH, when UL115 and CMV gH are coexpressed, the two proteins form complexes and are secreted from the host cell. As with CMV gL, the FGF receptor has been found to serve an escort function with CMV gH and may function as an escort for other homologous herpesvirus proteins.

As explained above, the hepatitis viral products will also be conveniently expressed using the present system. By way of example, the HCV genome encodes several viral proteins, including E1 (also known as E) and E2 (also known as E2/NSI). (See, Houghton et al., *Hepatology* (1991) 14:381–388, for a discussion of HCV proteins, including E1 and E2, and EPO publication No. 388,232, for the HCV genomic sequence). These proteins are membrane associated asialoglycoproteins when expressed in recombinant systems. The HCV virus may gain entry into host cells during infection through either the asialoglycoprotein receptor found on hepatocytes, or through the mannose receptor found on hepatic endothelial cells and macrophages. (See, Exekowitz et al., *J. Exp. Med.* (1990) 176:1785–1794; Kurata et al., *J. Biol. Chem.* (1990) 265:11295–11298; Schuffenecker et al., *Cytogenet. Cell. Genet.* (1991) 56:99–102; and Sastry et al., *J. Immunol.* (1991) 147:692–697 for a discussion of mannose and asialoglycoprotein receptors.) The mannose receptor has been cloned (Taylor et al., *J. Biol. Chem.* (1990) 265:12156–12162), as has the asialoglycoprotein receptor (Drickamer et al., *J. Biol. Chem.* (1984) 259:770–778; Spiess et al., *Proc. Natl. Acad. Sci. USA* (1985) 82:6465–6469; McPhaul and Berg, *Proc. Natl. Acad. Sci. USA* (1986) 83:8863–8867; McPhaul and Berg, *Mol. Cell. Biol.* (1987) 7:1841–1847). These receptors will find use as escorts for the recombinant production of HCV proteins such as E1 and E2.

The expression of HIV proteins can also be facilitated using the present methods. The HIV env gene encodes the envelope proteins of the virus, including the glycoproteins gp160, gp120 and gp41. As explained above, gp160 is not properly processed or transported in recombinant systems. (Haffar et al., *J. Virol.* (1990) 6.4:3100–3103.) Furthermore CD4, the cellular receptor for HIV, appears to play a role in protein transport. Specifically, a CD4 mutant, modified to contain a specific retention signal for the endoplasmic reticulum, successfully blocks secretion of gp120 and surface expression of gp160. Buonocore and Rose, *Nature* (1990) 345:625–628. Accordingly, the use of CD4 as an escort for facilitating expression of the HIV envelope proteins is also contemplated herein.

Additional examples of proteins and compatible escorts for coexpression therewith will readily occur to those of skill in the art in view of the above discussion.

A. Isolating the Desired Gene

As explained above, the proteins and escorts for use with the present invention can be recombinantly produced. DNA encoding the protein of interest can be genomic, cDNA or synthetic DNA. Methods for obtaining or synthesizing DNA for subsequent cloning are well known in the art. For example, the desired protein can be purified and the amino acid sequence determined by repetitive cycles of Edman degradation, followed by amino acid analysis by HPLC. Other methods of amino acid sequencing are also known in the art. Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*:

Vol. I, supra; *Nucleic Acid Hybridization*, supra; *Oligonucleotide Synthesis*, supra; T. Maniatis et al., supra.

First, a DNA library is prepared. Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge *Nature* (1981) 292:756; Nambair et al. *Science* (1984) 223:1299; Jay et al. *J. Biol. Chem.* (1984) 259:6311.

B. Expression Systems

Once the appropriate coding sequence for the desired protein and escort are isolated or synthesized, they can be coexpressed in a variety of different expression systems; for example those used with mammalian cells, baculoviruses, bacteria, and yeast. For coexpression, two or more plasmids encoding the desired products can be employed. Alternatively, a single construct, encoding both the desired protein and the escort, can be used. The single construct can either consist of a chimeric DNA molecule encoding for a fusion protein including the escort and desired protein, or can include DNAs coding for two separate products.

i. Mammalian Systems

Mammalian expression systems are known in the art and will find use in the subject invention. Mammalian expression systems will include a mammalian promoter which is any DNA sequence capable of binding mammalian RNA polymerase and initiating the downstream (3') transcription of a coding sequence (e.g., structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation (Sambrook et al., *Molecular Cloning: A Laboratory Manual, 2nd ed.*, supra.

Mammalian viral genes are often highly expressed and have a broad host range. Therefore, sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from nonviral genes, such as the murine metallothionein gene, also provide useful promoter sequences. Expression may be either constitutive or regulated (inducible), depending on the promoter and can be induced with glucocorticoid in hormone-responsive cells.

Enhancer elements can also be used. The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter (Maniatis et al., *Science* (1987) 236:1237; Alberts et al. (1989) *Molecular Biology of the Cell,* 2nd ed.). Enhancer elements derived from viruses may be particularly useful because they typically have a broader host range. Examples include the SV40 early gene enhancer (Dijkema et al., *EMBO J.* (1985) 4:761) and the enhancer/promoters derived from the long terminal repeat (LTR) of the Rous Sarcoma Virus (Gorman et al., *Proc. Natl. Acad. Sci. USA* (1982b) 79:6777) and from human cytomegalovirus (Boshart et al., *Cell* (1985) 41:521). Additionally, some enhancers are regulatable and become active only in the presence of an inducer, such as a hormone or metal ion (Sassone-Corsi and Borelli, Trends Genet. (1986) 2:215; Maniatis et al., *Science* (1987) 236:1237).

The desired proteins and escorts can also be expressed as fusion proteins comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus tripartite leader is an example of a leader sequence that provides for secretion of a foreign protein in mammalian cells.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., *Cell* (1985) 41:349; Proudfoot and Whitelaw (1988) "Termination and 3' end processing of eukaryotic RNA. In Transcription and Splicing (ed. B. D. Hames and D. M. Glover); Proudfoot, *Trends Biochem. Sci.* (1989) 14:105). These sequences direct the transcription of an mRNA which can be translated into the polypeptide encoded by the DNA. Examples of transcription terminator/polyadenylation signals include those derived from SV40 (Sambrook et al. (1989) "Expression of cloned genes in cultured mammalian cells" in *Molecular Cloning: A Laboratory Manual*).

Some genes may be expressed more efficiently when introns (also called intervening sequences) are present. Several cDNAs, however, have been efficiently expressed from vectors that lack splicing signals (also called splice donor and acceptor sites) (see, e.g., Gothing and Sambrook, *Nature* (1981) 293:620). Introns are intervening noncoding sequences within a coding sequence that contain splice donor and acceptor sites. They are removed by a process called "splicing," following polyadenylation of the primary transcript (Nevins, *Ann. Rev. Biochem.* (1983) 52:441; Green, *Ann. Rev. Genet.* (1986) 20:671; Padgett et al., *Ann. Rev. Biochem.* (1986) 55:1119; Krainer and Maniatis, (1988) "RNA splicing" in *Transcription and splicing* (ed. B. D. Hames and D. M. Glover)).

Typically, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 (Gluzman, *Cell* (1981) 23:175) or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a procaryotic host for cloning and amplification. Examples of such mammalian-bacteria shuttle vectors include pMT2 (Kaufman et al., *Mol. Cell. Biol.* (1989) 9:946) and pHEBO (Shimizu et al., *Mol. Cell. Biol.* (1986) 6:1074).

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotides encoding the desired protein and escort can also be inserted into a suitable insect expression vector, where they are operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene into the baculovirus genome); and appropriate insect host cells and growth media.

After inserting the DNA sequences encoding the desired protein and escort into one or more transfer vectors, the vector(s) and the wild type viral genome are transfected into an insect host cell where the vector(s) and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequences encoding the protein and escort into the baculovirus genome, the above described components, comprising a promoter, leader (if desired), coding sequence of interest, and transcription termination sequence, are typically assembled into an intermediate transplacement construct (transfer vector). This construct may contain a single gene and operably linked regulatory elements; multiple genes, each with its own set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31).

The plasmid usually also contains the polyhedrin polyadenylation signal (Miller et al. *Ann. Rev. Microbiol.* (1988) 42:177) and a procaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression" in: *The Molecular Biology of Baculoviruses* (ed. Walter Doerfler); EPO Publication Nos. 127,839 and 155,476; and the gene encoding the p10 protein Vlak et al., *J. Gen. Virol.* (1988) 69:765.

DNA encoding suitable signal sequences can be derived from genes for secreted insect or baculovirus proteins, such as the baculovirus polyhedrin gene (Carbonell et al. *Gene* (1988) 73:409). Alternatively, since the signals for mammalian cell post-translational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of noninsect origin, such as those derived from genes encoding human α-interferon, Maeda et al., *Nature* (1985) 315:592; human gastrin-releasing peptide, Lebacq-Verheyden et al., *Molec. Cell. Biol.* (1988) 8:3129; human IL-2, Smith et al., *Proc. Nat'l Acad. Sci. USA* (1985) 82:8404; mouse IL-3, (Miyajima et al., Gene (1987) 58:273; and human glucocerebrosidase, Martin et al., *DNA* (1988) 7:99, can also be used to provide for secretion in insects.

A recombinant polypeptide or polyprotein when expressed intracellularly will generally include suitable translation initiation signals preceding an ATG start signal. If desired, methionine at the N-terminus may be cleaved from the mature protein by in vitro incubation with cyanogen bromide.

After insertion of the desired DNA sequences, an insect cell host is cotransformed with the heterologous DNA of the transfer vector(s) and the genomic DNA of wild type baculovirus—usually by cotransfection. The promoter and transcription termination sequence of the construct will typically comprise a 2–5 kb section of the baculovirus genome. Methods for introducing heterologous DNA into the desired site in the baculovirus virus are known in the art. (See Summers and Smith, supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., *Bioessays* (1989) 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Thus, the expression system provides a visual screen allowing recombinant viruses to be distinguished from wild-type virus. The polyhedrin protein, which is produced by the native virus, is produced at very high levels in the nuclei of infected cells at late times after viral infection. Accumulated polyhedrin protein forms occlusion bodies which also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al., eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (PCT Publication No. WO 89/046699; Carbonell et al., *J. Virol.* (1985) 56:153; Wright, *Nature* (1986) 321:718; Smith et al., *Mol. cell. Biol.* (1983) 3:2156; and see generally, Fraser, et al., *In Vitro Cell. Dev. Biol.* (1989) 25:225).

Cells and cell culture media are commercially available for both direct and fusion expression of heterologous polypeptides in a baculovirus/expression system; cell culture technology is generally known to those skilled in the art. See, e.g., Summers and Smith supra.

The infected insect cells may then be grown in an appropriate nutrient medium, which allows for expression of the recombinant product. The product may be purified by such techniques as chromatography, e.g., HPLC, affinity chromatography, ion exchange chromatography, etc.; electrophoresis; density gradient centrifugation; solvent extraction, or the like, As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain expression, infected cells are incubated under conditions which allow expression of the recombinant coding sequences. These conditions will vary, depending upon the host cell selected. However, the conditions are readily ascertainable to those of ordinary skill in the art, based upon what is known in the art.

iii. Bacterial Systems

Bacterial expression techniques are known in the art. Bacterial expression systems will include a bacterial promoter which is any DNA sequence capable of binding bacterial RNA polymerase and initiating the downstream (3") transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence which, if present, is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al., *Annu. Rev. Genet.* (1984) 18:173). Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature* (1977) 198:1056), and maltose. Additional examples include promoter sequences derived from biosynthetic enzymes such as tryptophan (trp) (Goeddel et al., *Nuc. Acids. Res.* (1980) 8:4057; Yelverton et al., *Nucl. Acids Res.* (1981) 9:731; U.S. Pat. No. 4,738,921; EPO Publication Nos. 036,776 and 121,775). The b-lactamase (bla) promoter system (Weissmann (1981) "The cloning of interferon and other mistakes" in *Interferon* 3 (ed. I. Gresser)), bacteriophage lambda PL (Shimatake et al., *Nature* (1981) 292:128) and T5 (U.S. Pat. No. 4,689,406) promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551, 433). For example, the tac promoter is a hybrid trp-lac promoter comprised of both trp promoter and lac operon sequences that is regulated by the lac repressor (Amann et al., *Gene* (1983) 25:167; de Boer et al., *Proc. Natl. Acad. Sci.* (1983) 80:21). Furthermore, a bacterial promoter can include naturally occurring promoters of nonbacterial origin that have the ability to bind bacterial RNA polymerase and initiate transcription. A naturally occurring promoter of nonbacterial origin can also be coupled with a compatible RNA polymerase to produce high levels of expression of some genes in prokaryotes. The bacteriophase T7 RNA polymerase/promoter system is an example of a coupled promoter system (Studier et al., *J. Mol. Biol.* (1986) 189:113; Tabor et al., *Proc Natl. Acad. Sci.* (1985) 82:1074). In addition, a hybrid promoter can also be comprised of a bacteriophage promoter and an *E. coli* operator region (EPO Publication No. 267,851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (Shine et al., *Nature* (1975) 254:34).

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo or in vitro incubation with a bacterial methionine N-terminal peptidase (EPO Publication No. 219,237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, a bacteriophage lambda gene can be linked at the 5' terminus of a foreign gene and expressed in bacteria. The resulting fusion protein preferably retains a site for a processing enzyme (factor Xa) to cleave the bacteriophage protein from the foreign gene (Nagai et al. (1984) *Nature* 309:810). Fusion proteins can also be made with sequences from the lacZ (Jia et al., *Gene* (1987) 60:197), trpE (Allen et al., *J. Biotechnol.* (1987) 5:93; Makoff et al., *J. Gen. Microbiol.* (1989) 135:11), and Chey (EPO Publication No. 324,647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g., ubiquitin specific processing-protease) to cleave the ubiquitin from the foreign protein. Through this method, native foreign proteins can be isolated (Miller et al., *Bio/Technology* (1989) 7:698).

Alternatively, foreign proteins can also be secreted from the cell by creating chimeric DNA molecules that encode a fusion protein comprised of a signal peptide sequence fragment that provides for secretion of the foreign protein in bacteria (U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) (Masui et al., (1983), in: *Experimental Manipulation of Gene Expression*; Ghrayeb et al., *EMBO J.* (1984) 3:2437) and the *E. coli* alkaline phosphatase signal sequence (phoA) (Oka et al., *Proc. Natl. Acad. Sci.* (1985) 82:7212). As an additional example, the signal sequence of the alpha-amylase gene from various Bacillus strains can be used to secrete heterologous proteins from *B. subtilis* (Palva et al., *Proc. Natl. Acad. Sci. USA* (1982) 79:5582; EPO Publication No. 244, 042).

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Publication No. 127,328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline (Davies et al., *Ann. Rev. Microbiol.* (1987) 32:469). Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: Bacillus subtilis (Palva et al., *Proc. Natl. Acad. Sci. USA* (1982) 79:5582; EPO Publication Nos. 036,259 and 063,953; PCT Publication No. WO 84/04541], *E. coli* (Shimatake et al., *Nature* (1981) 292:128; Amann et al., *Gene* (1985) 40:183; Studier et al., *J. Mol. Biol.* (1986) 189:113; EPO Publication Nos. 036,776, 136,829 and 136, 907), *Streptococcus cremoris* (Powell et al., *Appl. Environ. Microbiol.* (1988) 54:655); *Streptococcus lividans* (Powell et al., *Appl. Environ. Microbiol.* (1988) 54:655), Streptomyces lividans (U.S. Pat. No. 4,745,056).

Methods for introducing exogenous DNA into bacterial hosts are well known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See, e.g., (Masson et al., *FEMS Microbiol. Lett.* (1989) 60:273; Palva et al., *Proc. Natl. Acad. Sci. USA* (1982) 79:5582; EPO Publication Nos. 036,259 and 063,953; PCT Publication No. WO 84/04541, Bacillus), (Miller et al., *Proc. Natl. Acad. Sci.* (1988) 85:856; Wang et al., *J. Bacteriol.* (1990) 172:949, Campylobacter), (Cohen et al., *Proc. Natl. Acad. Sci. USA* (1973) 69:2110; Dower et al., *Nucleic Acids Res.* (1988) 16:6127; Kushner (1978) "An improved method for transformation of *Escherichia coli* with ColE1-derived plasmids" in *Genetic Engineering: Proceedings of the International Symposium on Genetic Engineering* (eds. H. W. Boyer and S. Nicosia); Mandel et al., *J. Mol. Biol.* (1970) 53:159; Taketo *Biochim. Biophys. Acta* (1988) 949:318; Escherichia), (Chassy et al., *FEMS Microbiol. Lett.* (1987) 44:173 Lactobacillus); (Fiedler et al., *Anal. Biochem* (1988) 170:38, Pseudomonas); (Augustin et al., *FEMS Microbiol. Lett.* (1990) 66:203, Staphylococcus), (Barany et al., *J. Bacteriol.* (1980) 144:698; Harlander (1987) "Transformation of *Streptococcus lactis* by electroporation," in: *Streptococcal Genetics* (ed. J. Ferretti and R. Curtiss III); Perry et al., *Infec. Immun.* (1981) 32:1295; Powell et al., *Appl. Environ. Microbiol.* (1988) 54:655; Somkuti et al., *Proc. 4th Evr. Cong. Biotechnology* (1987) 1:412, Streptococcus).

iv. Yeast Expression

Yeast expression systems are also known to one of ordinary skill in the art. A yeast promoter is used in such systems and is any DNA sequence capable of binding yeast RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of an UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publication No. 284,044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publication No. 329,203). The yeast PHO5 gene, encoding acid phosphatase, also provides useful promoter sequences (Myanohara et al., *Proc. Natl. Acad. Sci. USA* (1983) 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publication No. 164,556). Furthermore, a yeast promoter can include naturally occurring promoters of nonyeast origin that have the ability to bind yeast RNA polymerase and initiate transcription. Examples of such promoters are described in, inter alia, Cohen et al., *Proc. Natl. Acad. Sci. USA* (1980) 77:1078; Henikoff et al., *Nature* (1981) 283:835; Hollenberg et al., *Curr. Topics Microbiol. Immunol.* (1981) 96:119; Hollenberg et al., (1979) "The Expression of Bacterial Antibiotic Resistance Genes in the Yeast Saccharomyces cerevisiae" in: *Plasmids of Medical, Environmental and Commercial Importance* (eds. K. N. Timmis and A. Puhler); Mercerau-Puigalon et al., *Gene* (1980) 11:163; Panthier et al., *Curr. Genet.* (1980) 2:109.

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See, e.g., EPO Publication No. 196,056. Another example is a ubiquitin fusion protein. Such a fusion protein is made with the ubiquitin region that preferably retains a site for a processing enzyme (e.g., ubiquitin-specific processing protease) to cleave the ubiquitin from the foreign protein. Through this method, therefore, native foreign protein can be isolated (see, e.g., PCT Publication No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (EPO Publication No. 012,873; JPO Publication No. 62,096,086) and the A-factor gene (U.S. Pat. No. 4,588,684). Alternatively, leaders of nonyeast origin, such as an interferon leader, exist that also provide for secretion in yeast (EPO Publication No. 060,057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; EPO Publication No. 324,274). Additional leaders employing an alpha-factor leader fragment that provides for secretion include hybrid alpha-factor leaders made with a presequence of a first yeast, but a pro-region from a second yeast alphafactor. (See, e.g., PCT Publication No. WO 89/02463.)

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of such sequences include those found in association with sequences coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., *Gene* (1979) 8:17–24), pCl/1 (Brake et al., *Proc. Natl. Acad. Sci USA* (1984) 81:4642–4646), and YRp17 (Stinchcomb et al., *J. Mol. Biol.* (1982) 158:157). In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect of the vector and the foreign protein on the host. See, e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., *Methods in Enzymol.* (1983) 101:228–245). An integrating vector may be directed to a specific locus in yeast by selecting the appropriate homologous sequence for inclusion in the vector. See Orr-Weaver et al., supra. One or more expression constructs may integrate, possibly affecting levels of recombinant protein produced (Rine et al., *Proc. Natl. Acad. Sci. USA* (1983) 80:6750). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metals. For example, the presence of CUP1 allows yeast to grow in the presence of copper ions (Butt et al. *Microbiol, Rev.* (1987) 51:351).

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz et al., *Mol. Cell. Biol.* (1986) 6:142), *Candida maltosa* (Kunze et al., *J. Basic Microbiol.* (1985) 25:141), *Hansenula polymorpha* (Gleeson et al., *J. Gen. Microbiol.* (1986) 132:3459; Roggenkamp et al., *Mol. Gen. Genet.* (1986) 202:302), *Kluyveromyces fragilis* (Das et al., *J. Bacteriol.* (1984) 158:1165), *Kluyveromyces lactis* (De Louvencourt et al., *J. Bacteriol.* (1983) 154:737; Van den Berg et al., *Bio/Technology* (1990) 8:135), *Pichia guillerimondii* (Kunze et al., *J. Basic Microbiol.* (1985) 25:141), *Pichia pastoris* (Cregg et al., *Mol. Cell. Biol.* (1985) 5:3376; U.S. Pat. Nos. 4,837,148 and 4,929,555), *Saccharomyces cerevisiae* (Hinnen et al., *Proc. Natl. Acad. Sci. USA* (1978) 75:1929; Ito et al., *J. Bacteriol.* (1983) 153:163), *Schizosaccharomyces pombe* (Beach and Nurse, *Nature* (1981) 300:706), and *Yarrowia lipolytica* (Davidow et al., *Curr. Genet.* (1985) 10:380471; Gaillardin et al., *Curr. Genet.* (1985) 10:49).

Methods of introducing exogenous DNA into yeast hosts are well known in the art, and typically include either the transformation of spheroplasts or of intact yeast cells treated with alkali cations. Transformation procedures usually vary with the yeast species to be transformed. See, e.g., Kurtz et al., *Mol. cell. Biol.* (1986) 6:142; Kunze et al., *J. Basic Microbiol.* (1985) 25:141; Candida); (Gleeson et al., *J. Gen. Microbiol.* (1986) 132:3459; Roggenkamp et al., *Mol. Gen. Genet.* (1986) 202:302; Hansenula); (Das et al., *J. Bacteriol.* (1984) 158:1165; De Louvencourt et al., *J. Bacteriol.* 154:1165; Van den Berg et al. (1990) *Bio/Technology* (1983) 8:135; Kluyveromyces); (Cregg et al., *Mol. Cell. Biol.* (1985) 5:3376; Kunze et al., *J. Basic Microbiol.* (1985) 25:141; U.S. Pat. Nos. 4,837,148 and 4,929,555; Pichia); (Hinnen et al., *Proc. Natl. Acad. Sci. USA* (1978) 75;1929; Ito et al., *J. Bacteriol.* (1983) 153:163); Saccharomyces); (Beach and Nurse, *Nature* (1981) 300:706; Schizosaccharomyces); (Davidow et al., *Curr. Genet.* (1985) 10:39; Gaillardin et al., *Curr. Genet.* (1985) 10:49; Yarrowia).

C. Purification of the Desired Polypeptide

Once expressed and secreted, the polypeptide of interest can be purified from collected media using any of several techniques known in the art. Convenient techniques include affinity chromatography and immunoprecipitation, (see, e.g., Weir and Moss, (1985)). For example, CMV gH can be easily purified using Murine monoclonal antibody 1G6 (Rasmussen et al., PNAS (1984) 81:876880), either by immunoprecipitation or affinity column chromatography. For affinity chromatography, the ligand may be covalently coupled to solid supports such as cellulose, polystyrene, polyacrylamide, crosslinked dextran, beaded agarose or controlled pore glass using bifunctional coupling agents that react with functional groups on the support and functional groups (i.e., reactive amino acid side chains) on the ligand molecule. See *Scientific Foundations of clinical Biochemistry*, vol. 1, pp. 202 et seq. (1978). The resulting ligand-bearing solid phase is contacted with disruptates of cells transformed with the gene encoding the protein of interest or conditioned media from the same, using reducing conditions, pH, ionic strength, temperature (typically physiological), and residence times that permit the desired polypeptide to bind to the immobilized ligand. The cells may be disrupted by sonication, lysing or other methods. The solid phase is separated from the disruptate after the incubation and washed with buffer to remove residual unbound disruptate. The protein is eluted from the solid phase by passing an elutant that dissociates hydrogen bonds through the bed. Bases that lower the pH to below about 3 or NaCl solutions above about 2M are commonly used elutants.

If monoclonal antibodies are used, these can be prepared by selection of an antibody raised against the protein of interest. Monoclonal antibodies to the protein may be made by the somatic cell hybridization techniques described initially by Kohler and Milstein, *Nature* (1975) 256:495–497. The procedure involves immunizing a host animal (typically a mouse because of the availability of murine myelomas) with the protein of interest.

Antibody-producing cells (e.g., peripheral blood lymphocytes, and splenocytes) are taken from the immunized host and mixed with a suitable tumor fusion partner in a liquid growth medium containing a fusogen such as polyethylene glycol of molecular weight 2000 to 5000. After the fusion, the cells are washed to remove residual fusion medium and incubated in a selective growth medium (i.e., a growth medium containing additives to which the parent tumor line is sensitive) such as HAT medium. Only hybrid cells that possess the parent noncancerous cells' ability to survive culture in the selective medium and the parent tumor cells' immortality survive culture in the selective medium. Surviving hybrids may be expanded and their culture media screened for the presence of appropriate antibodies by radioimmunoassay (RIA), a microneutralization assay that detects inhibition of viral cytopathic effect (CPE) in cell cultures, or other assays that detect antiviral activity (e.g., plaque reduction). Positive cultures may be screened for their ability to recognize and bind to the desired protein by immunoprecipitating labeled infected cell extracts with the positive cultures and analyzing the precipitate by SDS-PAGE for the presence of a labeled protein component. Hybrids that produce antibody that binds specifically to the protein may be subcloned and grown in vitro or in vivo by known procedures. The antibody may be isolated from the resulting culture medium or body fluid, as the case may be, by conventional procedures for isolating immunoglobulins.

Below are examples of specific embodiments for carrying out the present invention. The examples are offered for illustrative purposes only, and are not intended to limit the scope of the present invention in any way.

Examples

Example 1

Nucleotide and Amino Acid Sequencing of CMV gH

The two main laboratory isolates of human CMV are AD169 (Rasmussen, L., et al., *Proc. Natl. Acad. Sci. USA* (1984) 81:876–880), and strain Towne (Pachl, C., et al., *Virology* (1989) 169:418–426). Both strains encode a gH, and these glycoproteins share substantial sequence similarity and are immunologically cross-reactive. Other strains of CMV can readily be used for the source of gH sequences.

The identification and isolation of the 3910 bp HindIII to PstI fragment of the strain Towne CMV genome, which contains a 2226 bp gH open reading frame is described in Pachl, C., et al., *Virology* (1989) 169:418–426, and shown in FIGS. 1A–1G & 2. The gH sequence is 742 amino acids (84.3 kD) and has the characteristics of a membrane glycoprotein.

Immunologically equivalent fragments of human CMV gH, for example, from AD169 or strain Towne, may be identified by making analogs of the polynucleotide sequence encoding the protein that are truncated at the 3' and/or 5' ends of the sequence and/or have one or more internal deletions, expressing the analog polynucleotide sequences, and determining whether the resulting fragments immunologically react with a CMV antibody or induce the production of such antibodies in vivo, particularly neutralizing antibodies. For example, deletion within or encompassing a 13 amino acid hydrophobic peptide (residues $Met_{340}$ to $Ala_{352}$) may facilitate secretion of gH. Similarly, deletions from within or encompassing the 34 residues (709–742) from the C-terminal transmembrane and internal regions, facilitate secretion. Deletions of the last 22 and 23 C-terminal residues are described in the examples, below. These fragments retain either the first two or three amino acids, respectively, of the putative gH transmembrane domain.

Example 2

Cloning Truncated Human CMV gH in a Mammalian system

For this example, human CMV virus was grown in cultures of human foreskin fibroblast (HF) cells with Dulbecco's modified Eagle (DME) medium (Gibco Laboratories, Grand Island, N.Y.), as described by Spaete and Mocarski, *J. Virol.* (1985) 56:135–143, but supplemented with 10% fetal calf serum (FCS). COS 7 cells were grown in the same medium described for HF cells.

Plasmid pRL108a (LaFemina and Hayward (1980) in *Animal Virus Genetics* (B. N. fields, R. Jaenisch, and C. F. Fox, Eds.) Vol. 28, pp. 39–55, Academic Press, New York), encodes the HindIII H fragment of CMV (Towne) cloned into plasmid pBR322. The gH gene was subcloned from the CMV (Towne) HindIII H fragment (pRL108a) as a 5.15 kb EcoRI to NcoI fragment and inserted into plasmid pGEM2 (Promega, Madison, Wis.), generating plasmid pXgH5. Expression plasmid pSVgH2 was constructed by isolating a 2577 bp SmaI to TthlllI (partial) fragment, encoding the gH gene, from plasmid pXgH5. This fragment was treated with Klenow fragment to blunt the ends and ligated into the SmaI site of the SV40-based expression plasmid pSV7d (Truett et al., *DNA* (1988) 4:333–349, generating plasmid pSVgH2.

Expression plasmids encoding truncated gH were constructed which contain a gH gene in which most of the transmembrane region of gH was deleted by removal of the last 22 amino acids from the C-terminus of gH. These constructs retain the first three amino acids of the gH transmembrane domain, ($Leu_{718}$-$Leu_{719}$-$Met_{720}$). Two of these constructs, pSVgH6a and pSVgH6b, differed from each other in the polylinker sequences at the 3' end of gH. For pSVgH6a, an additional ten amino acids were encoded by the polylinker region, 3' to (SEQ. NO:11) $Met_{720}$ ($Gly_{721}$-$Ser_{722}$-$Arg_{723}$-$Gly_{724}$ -$Ser_{725}$-$Val_{726}$-$Asp_{727}$-$Leu_{728}$-$Asp_{729}$-$Lys_{730}$) and for pSVgH6b, an additional six amino acids were encoded by the polylinker (SEQ. NO:12) ($Leu_{721}$-$Glu_{722}$-$Asp_{723}$-$Pro_{724}$-$Ser_{725}$-$Thr_{726}$). Plasmids pSVgH6a and pSVgH6b were generated by isolating a 2262 bp EcoRI plus BsphI (partial) fragment from pSVgH2. This fragment was then ligated to EcoRI plus SmaI cut pSV7d (for pSVgH6a) or to EcoRI plus XbaI cut pSV7d (for pSVgH6b). A third plasmid, pCMAdgH6 (FIG. 2, ATCC Accession No. 69035), bearing a truncated gH gene as above, was generated by cloning a 2775 bp EcoRI to SalI gH fragment from plasmid pSVgH6b into the SalI site of plasmid pCMVAdhfr (Spaete et al. *J. Virol.* (1990) 64:2922–2931). This gH fragment encodes a 22 amino acid C-terminally truncated gH lacking the transmembrane and cytoplasmic domains (including the six additional amino acids encoded by the polylinker of pSVgH6b as described above), and includes the selectable dhfr gene.

Plasmid pCMAdgH6 was used to transfect Chinese hamster ovary (CHO) cell line 171 as described previously. (Spaete et al., *Progress in Cytomegalovirus Research* (M. P. Landini, ed., 1991) pp. 133–136). Briefly, CHO cell line 171 is a 0.1 μM methotrexate amplified derivative of parent cell line CR-7, transfected with pCMAdgH6. Media from transfected cells was analyzed by a standard ELISA to screen for positive clones. RIP analysis of medium conditioned by growth of cell line 171 was not positive for truncated gH.

Example 3

Cloning Full-length Human CMV gH in a Baculovirus System

Figure 3:
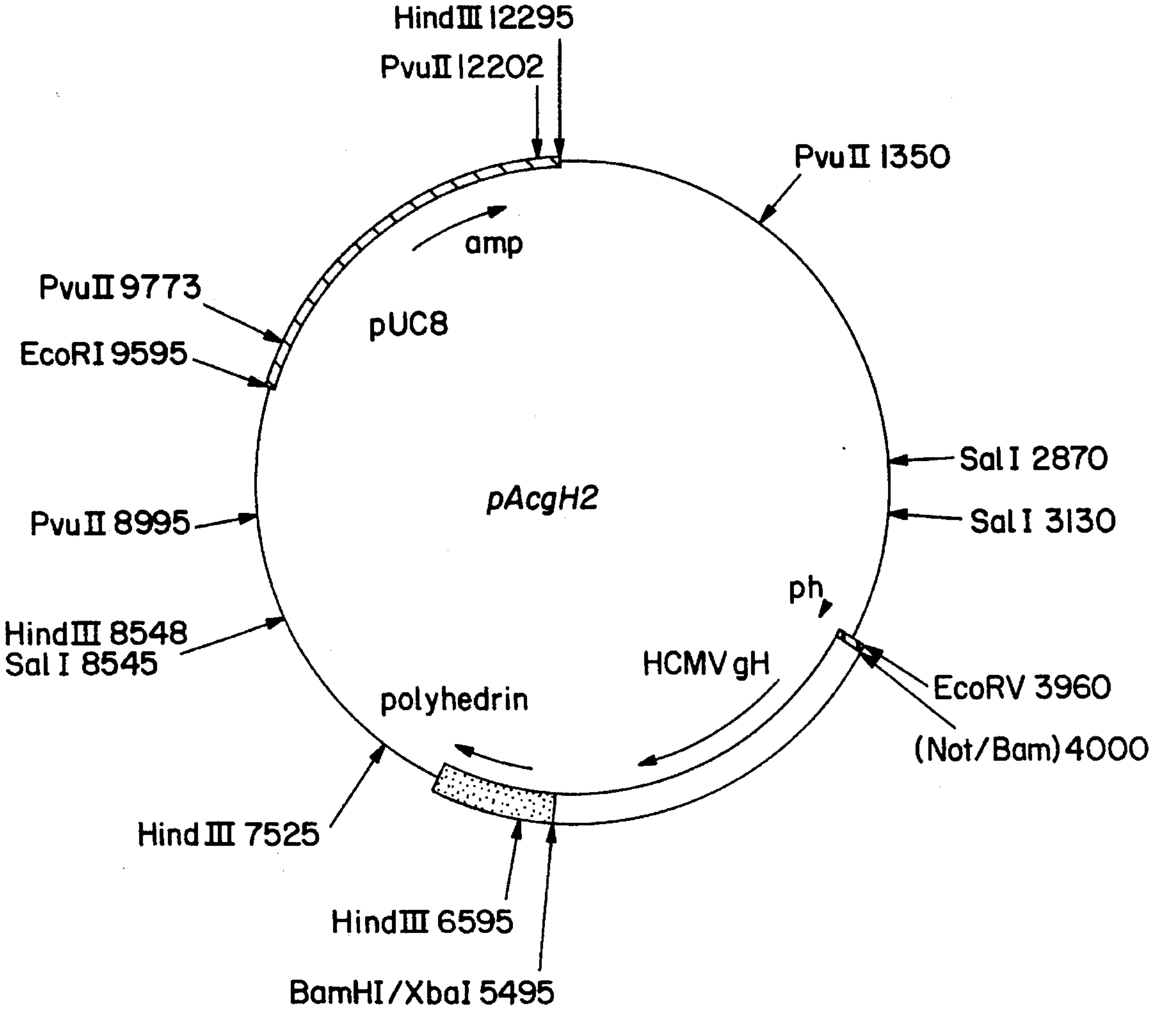
FIG. 3 is a diagram of pACgH2, a CMV gH baculovirus transfer vector in which the gH coding sequence has been spliced into the BamH1 site of pAc373.

A baculovirus-gH transfer vector encoding full-length gH (gH2) was prepared as follows. Baculovirus vector pAc373 (Smith et al., *Proc. Natl. Acad. Sci.* (1985) 82:8404–8408) was cut with BamHI and the 2495 bp NotI to XbaI gH fragment of plasmid pSVgH2 (described in example 2) was filled and ligated into this BamHI site. The resulting plasmid, designated pACgH2 (see FIG. 3), encodes a gH construct where transcription is driven by the baculovirus polyhedrin gene promoter. This DNA plasmid was mixed with wildtype baculovirus viral DNA, the mixture was transfected into cells derived from *Spodoptera frugiperda* (Sf9 cells), and recombinant plaques were isolated and plaque purified. Several recombinant virus clones were used to infect cells, and at four to six days after infection, cell lysates and conditioned media were analyzed by ELISA and Western blot. No extracellular expression of full-length gH (pACgH2) was detected.

Extracellular expression of gH in Sf9 cells infected with a recombinant baculovirus containing pACgH2 was also analyzed by radioimmunoprecipitation (RIP), using monoclonal IG6 or human sera. No gH-specific bands were detected from RIPs of baculovirus-pACgH2 (full-length gH) media, indicating that extracellular expression was not achieved.

To test whether full-length gH was expressed intracellularly, Sf9 cells were infected at a MOI of 5 with gH2 (full-length gH). Five days post infection, the cells were stained with a monoclonal antibody against gH, as the primary antibody. Cells were incubated with goat $F(ab')^2$ anti-mouse IgG-FITC conjugate, treated with paraformaldehyde and analyzed for cell surface gH expression on a Coulter EPICS-C flow cytometer. As a positive control, cells were infected with truncated gH (described below), fixed with paraformaldehyde and permeabilized with detergent before primary antibody treatment to visualize intracellular gH expression. Intracellular staining was observed with both full-length and truncated gH. Thus, full-length gH and truncated gH are expressed intracellularly.

Example 4

Cloning Truncated Human CMV gH in a baculovirus system

Figure 4:
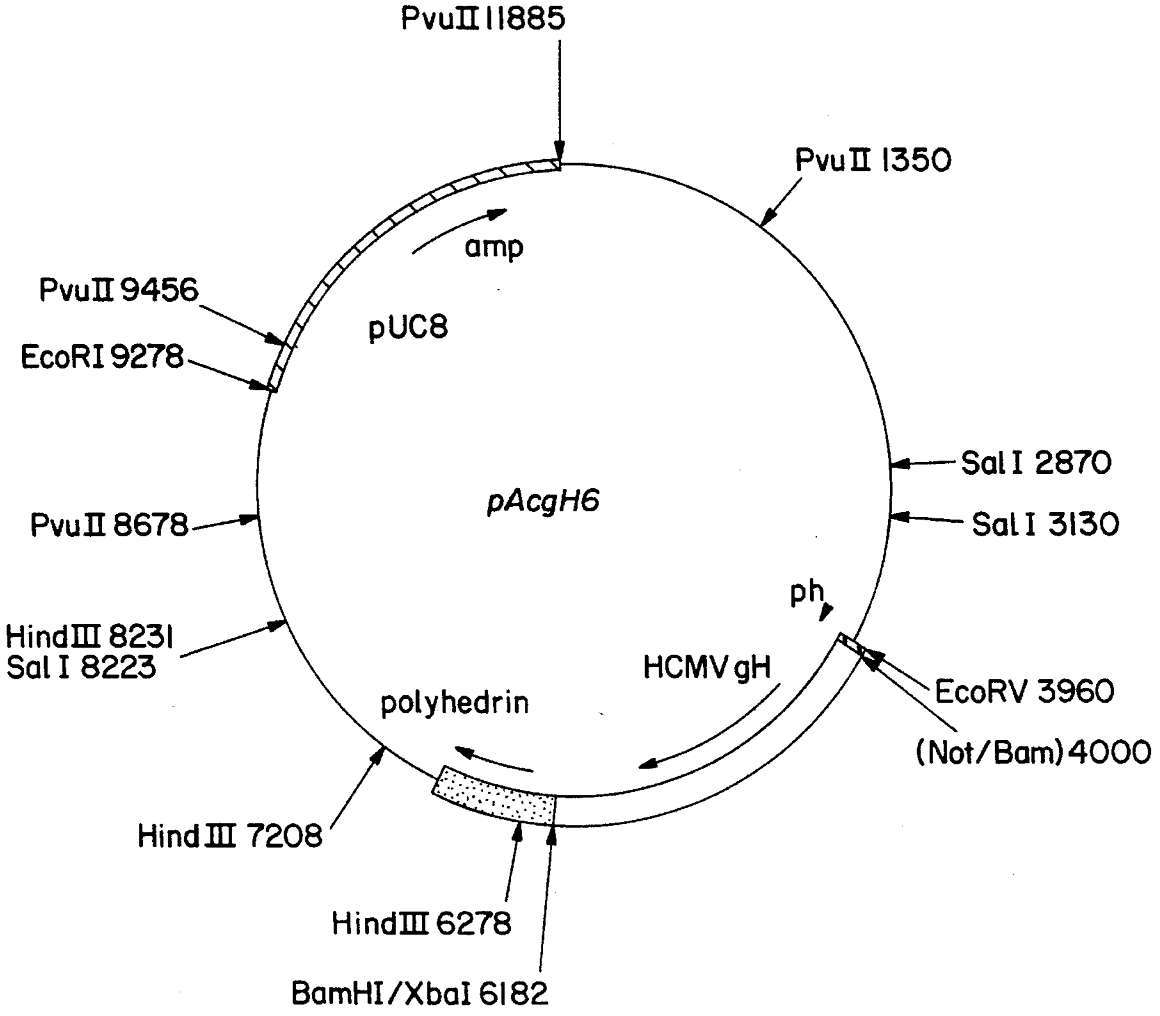
FIG. 4 is a diagram of the truncated gH transfer vector (pACgH6) in which the CMV gH coding sequence has been spliced into the BamH1 site of pAc373.

A baculovirus-gH transfer vector encoding a fragment of gH, lacking a C-terminal domain, was prepared. Baculovirus vector pAc373 (Smith et al., *Proc. Natl. Acad. Sci.* (1985) 82:8404–8408) was cut with BamHI and the 2178 bp NotI to SalI fragment from pCM6-H6 was filled and ligated into this BamHI site. pCM6-H6 was constructed by ligation of an EcoRI/SalI gH fragment from pSVgH6b (as described in Example 2) to EcoRI/SalI digested mammalian cell expression vector pCMV6c (Chapman et al., *Nuc. Acids Res.* (1991) 19:3979–3986). The resulting plasmid, designated pACgH6 (ATCC Accession No. 68373, see FIG. 4) encodes a gH construct where transcription is driven by the baculovirus polyhedrin gene promoter. In this truncated gH segment most of the transmembrane region of gH was deleted by removal of the last 23 amino acids from the C-terminus of gH. The fragment retains only the first two amino acids of the gH transmembrane domain (Leu718-Leu719, FIGS. 1A–1G).

The plasmid was mixed with wild-type baculovirus viral DNA, used to cotransfect *Spodoptera frugiperda* cells and recombinant plaques were isolated and plaque purified. Several recombinant virus clones were used to infect cells, and at four to six days after infection, cell lysates and conditioned media were analyzed by ELISA and Western blot.

For all the pACgH6 containing clones, ELISA analysis showed gH reactivity for the culture media, indicating that truncated gH was expressed extracellularly in this system. While ELISA analysis of cell lysates was unable to detect the intracellular presence of truncated gH, RIP analysis was positive for truncated gH, indicating a low but detectable intracellular presence of truncated gH.

Example 5

Cloning and characterization of the FGF Receptor

A. Oligonucleotide Synthesis

Oligonucleotide adapters, probes and sequencing primers were synthesized by the phosphoramidite method using Applied Biosystems (Foster City, Calif.) model 380A and 380B synthesizers, purified by polyacrylamide gel electrophoresis and desalted on SEP-PAK $C_{18}$ cartridges (Waters, Milford, Mass.). The oligonucleotide probes used for screening the cDNA library were complementary to nucleotides 1–30 (SEQ. NO:13) (5' -ATAACGGACCTTGTAGCCTCCAATTCTGTG-3') and nucleotides 1840–1869 (5' -GCGGCGTTTGAGTCCGCCATTGGCAAGCTG-3') of the published flg nucleic acid sequence (Ruta et al., *Oncogene* (1988) 3:9–15). The two PCR primers used to amplify the extracellular region of the FGF receptor (flg5) cDNA consisted of a sense primer, P4 (SEQ. NO:15) (5' -CCAACCTCTAGAGGATCCACTGGGATGTGGAGCTGGAAGTGC-3') containing the ribosome binding site plus amino acids 1–6 of flg5 and an antisense primer, P3 (SEQ. NO:16) (5' -GTAAGCGGCCGCGGATCCTTACTACTCCAGGTACAGGGGCGA-3') containing amino acids 369–374 of flg5 and directly followed by a termination codon. Both primers contain BamHI sites to facilitate cloning into pAc373. Two additional PCR primers were used to identify two and three immunoglobulin like domain FGF receptors in various tissues. They were a sense primer, P1 (SEQ. NO:17) (5' -CCATTTGGATCCGTCACAGCCACACTCTGCACCGCT-3') encoding amino acids 14 to 21 of flg5 and an antisense primer P2 (SEQ. NO:18) (5' -CCATTTGTCGACTTCCATCTTTTCTGGGGATGTCCA-3') encoding the complement of amino acids 154 to 161 of flg5. The primers contain BamHI and SalI sites to facilitate cloning into M13 sequencing plasmids.

B. RNA Isolation and Construction and Screening of the cDNA Library

RNA was isolated by the guanidinium thiocyanate method (J. M. Chirgwin et al., *Biochem.* (1979) 18:5294–5299) with modifications (G. J. Freeman et al., *Proc. Natl. Acad. Sci. USA* (1983) 80:4094–4098). Poly(A)$^+$ RNA was purified by a single fractionation over oligo(dT) cellulose (H. Aviv & P. Leder, *Proc. Natl. Acad. Sci. USA* (1972) 69:1408–1412). The construction and screening of the Hep G2 library in λZAP has been described (Zapf et al., *J. Biol. Chem.* (1990) 265:14892–14898). The probes were labeled with $T_4$ polynucleotide kinase and [$\gamma$-$^{32}$P]-ATP (Sambrook et al., (1989) *Molecular Cloning: A Laboratory Manual* 2nd Ed. (Cold Spring Harbor Laboratory, Cold Spring Harbor, N.Y.) to a specific activity of $1–2\times10^8$ cpm/mg. Approximately 600,000 recombinant phages from the Hep G2 cDNA library were screened on duplicate nitrocellulose filters (Millipore, HATF 137), with two flg oligonucleotide probes. Areas of plaques that hybridized to both probes were further purified.

C. Plasmid Isolation, Subcloning and Sequencing

Bluescript SK(–) plasmids containing the putative flg cDNA inserts were released from λZAP by the M13 rescue/excision protocol described by the supplier (Stratagene). Plasmid DNA was isolated by the alkaline lysis method (Sambrook et al., (1989) *Molecular Cloning: A Laboratory Manual* 2nd Ed. (Cold Spring Harbor Laboratory, Cold Spring Harbor, N.Y.)). The cDNA inserts containing the putative flg sequence were excised from the Bluescript SK(–) vector by BglII or EcoRI digestion and fractionated by agarose gel electrophoresis. Inserts were excised from the gel and passively eluted for 16 h with gentle shaking in 10 mM Tris-hydrochloride, pH 7.5, 1 mM EDTA (TE), purified on elutip-D columns (Schleicher and Schuell) and subcloned into M13 sequencing vectors (Yanisch-Perron et al., *Gene* (1985) 33:103–119). PCR-amplified DNA was similarly purified. DNA sequencing was performed by the dideoxy chain termination method (Sanger et al., *Proc. Natl. Acad. Sci. USA* (1977) 74:5463–5467) using M13 primers as well as specific internal primers. Ambiguous regions were resolved using 7-deaza-2' -deoxyguanosine-5' -triphosphate (Barr et al., *Biotechniques* (1986) 4:428–432) and Sequenase (US Biochemicals).

Figure 5:
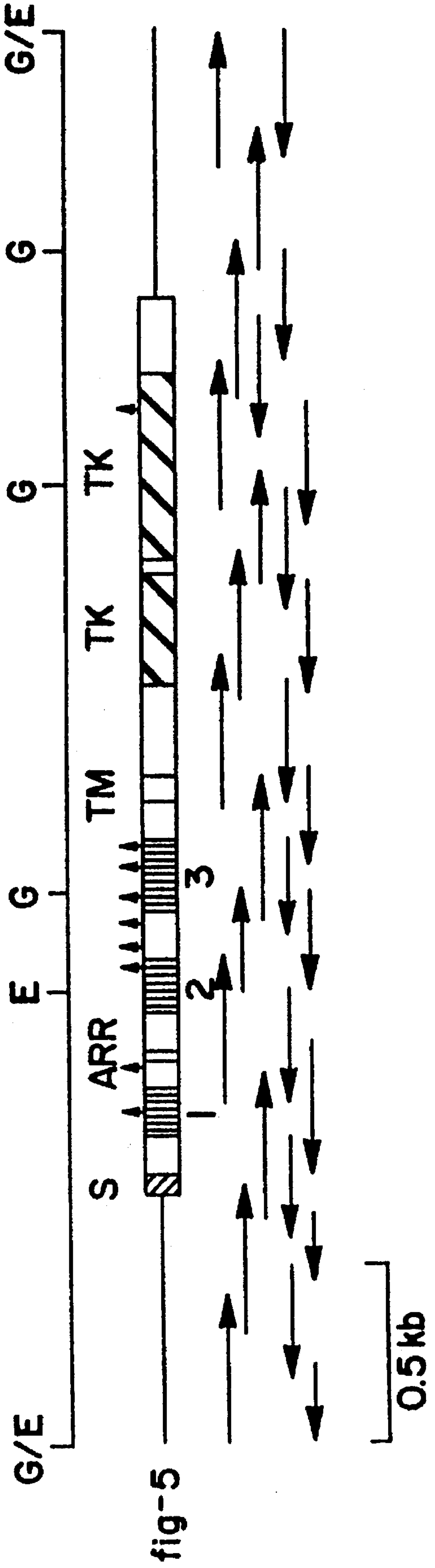
FIG. 5 depicts a schematic diagram of the human FGF receptor cDNA (flg5) and sequencing strategy. The translated regions are boxed, and various shaded domains are indicated: S, signal peptide; 1–3, immunoglobulin like-domains 1–3; ARR, acidic amino acid rich region; TM, transmembrane region; TK, tyrosine kinase domains. Potential Asn-linked glycosylation sites are also indicated (♦) as are the BglII (G) and EcoRI (E) restriction endonuclease sites. Although shown, the location of the most carboxyl-terminal consensus glycosylation site most likely precludes its use. Sequences were obtained by using M13 primers and specific internal primers. Arrows indicate the direction and extent of individual sequencing runs. The DNA sequence is in the Genbank and EMBL data bases, and accession numbers are available from these organizations.

To isolate full-length FGF receptor encoded cDNAs, 600,000 recombinants from a λZAP-human hepatoma cell line (Hep G2) cDNA library were screened with oligonucleotide probes derived from the 5' - and 3' -ends of a partial flg cDNA (Ruta et al., *Oncogene* (1988) 3:9–15). Six clones were identified that hybridized to both probes. BglII restriction endonuclease digestion of the cDNA inserts and gel analysis suggested that three of the six clones contained the complete coding sequence. Four BglII fragments of 1.6, 1.1, 0.6, and 0.55 Kb and two EcoRI fragments of 2.7 and 1.2 Kb were identified in the longest cDNA clone, flg5 (FIG. 5). BglII and EcoRI sites are also present in the flanking adapters that were used to make the cDNA library. The BglII and EcoRI fragments of flg5 cDNA were isolated, cloned into M13 mp19 and sequenced. A detailed sequencing strategy is shown in FIG. 5. The flg5 cDNA encodes a protein of 820 amino acids and is flanked by 671 and 753 nucleotides of 5' - and 3' -untranslated regions, respectively. The encoded protein revealed a structure that included a signal peptide, three extracellular immunoglobulin like domains, an acidic amino acid-rich region, a transmembrane domain and a split intracellular tyrosine kinase domain. These domains have been identified previously on the chicken (Lee et al., *Science* (1989) 245:57–60), the mouse (Reid et al., *Proc. Natl. Acad. Sci. USA* (1990) 87:1596–1600) and most recently, several human FGF receptors deduced from cDNA sequences (Isacchi et al., *Nuc. Acids Res.* (1990) 18:1906; Johnson et al., *Mol. Cell Biol.* (1990) 10:4728–4736). The encoded receptor also contains eight consensus N-linked glycosylation sites in the extracellular region and one in the cytoplasmic tyrosine kinase domain.

The amino acid sequence encoded by flg5 cDNA is shown in FIGS. 6A–6B (top row). For comparison, five other previously identified forms of the human FGF receptors are shown (Isacchi et al., supra; Johnson et al., supra) and are aligned for maximum amino acid sequence identity. The identified structural domains are indicated above the flg5 sequence, as are regions corresponding to the PCR primers. The putative signal peptidase cleavage site (von Heijne, *Nuc. Acids Res.* (1986) 14:4683–4690) after $Ala_{21}$ is indicated (↓). Differences or deletions of amino acids are boxed. The three most notable differences between the six FGF receptors are: i) a large deletion near the N-terminus in FGF receptors 3–6 ($aa_{31-119}$) that spans the entire first immunoglobulin like domain; ii) truncation of receptors 5 and 6, which differ from the other FGF receptors in their carboxyl terminal amino acids ($aa_{221-300}$ and $aa_{223-302}$ respectively), with consequent deletion of their transmembrane and cytoplasmic domains; and iii) deletion of amino acids 148 and 149 in FGF receptors 1, 3 and 5. Other differences in FGF receptor-3 ($aa_{101}$) and FGF receptor-2 ($aa_{817}$) are also noted. The partial flg sequence is not shown, but has an N-terminal amino acid corresponding to position 198 of FGF receptor-1. Accordingly, it may be encoded by the cDNAs of FGF receptors 1, 2, 3 or 4. It is important to note however, that the flg sequence displays a difference from FGF receptors 1–4 in the tyrosine kinase domain at $aa_{670-674}$, due to three nucleic acid deletions flanking this region that results in a limited frame shift.

D. PCR Amplification

Amplification reactions were performed according to the supplier of the PCR kit (Perkin Elmer Cetus). PCR primers and template were at a final concentration of 1 mM and 0.1–0.5 mg/mL, respectively. The cDNA encoding flg5 was used as a template DNA for the construction of EC-FGF receptor in pAc373. For expression studies, template DNA was reverse transcribed from mRNA as described (Zapf et al., supra). 30 cycles of PCR were performed using a Perkin Elmer Cetus DNA thermal cycler Each cycle consisted of a 94° C. 1 min denaturation step; a 55° C., 2 min annealing step; and a 72° C., 3 min extension step. The extension step in the last cycle was 7 min.

E. Construction of Recombinant EC-FGF Receptor Virus

The PCR amplified DNA fragment encoding the extracellular domain of the FGF receptor was digested with BamHI, gel purified and ligated to BamH1 cut, calf intestinal phosphatase-treated pAc373. Recombinant plasmids were analyzed for EC-FGF receptor cDNAs inserted in the correct orientation by restriction endonuclease digestion and agarose gel electrophoresis.

The recombinant plasmid was cotransfected with wild-type AcMNPV viral DNA into Sf9 cells by the calcium phosphate transfection procedure (Summers and Smith, supra). Recombinant viruses were identified in the first round of plaque screening by hybridization with flg5 cDNA that was $^{32}P$-labeled by replacement synthesis (Sambrook et al., supra). The recombinant viruses were further purified by visual screening for the occlusion negative phenotype in two additional rounds.

The recombinant baculovirus that expressed EC-FGF receptor was constructed by ligating PCR-amplified DNA encoding amino acids 1–374 of the flg5 cDNA into the BamH1 site of the baculovirus transfer vector pAc373. The PCR primers contained flanking BamH1 sites to facilitate cloning. In addition, the 5' sense primer (P4) contained, directly upstream from the initiation codon, the −1 to −5 nucleotides of the flg5 cDNA sequence that are implicated in ribosome binding (Kozak, M., *Nuc. Acids. Res.* (1984) 12:857–87239). The 3'-antisense primer (P3) contained two termination codons TAG and TAA directly after amino acid 374. Cotransfection of Sf9 cells with AcMNPV viral DNA and the recombinant construct (pAc373-EC-FGF receptor) by the calcium phosphate method (Summers and Smith, supra) generated recombinant baculovirus that were subsequently purified by plaque hybridization and visual screening.

Example 6

FGF Receptor Binding and Activity Assays.

A. Radioreceptor assay

The effects of the EC-FGF receptor on the binding of radioiodinated basic FGF to its receptor was examined using a radioreceptor assay as described in the art. Briefly, baby hamster kidney cells were maintained in Hepes (25 mM) buffered DMEM supplemented with 5% calf serum and antibiotics and were grown to subconfluence in 24-well dishes. The cells were washed twice with phosphate buffered saline and incubated for 3 hours at 4° C. with the indicated concentrations of the peptides and 1 ng (100,000 cpm) of labelled basic FGF in 300 μL of DMEM containing 0.1% gelatin. The medium was aspirated and the cells washed twice with 0.5 mL PBS and twice with 0.5 mL of PBS containing 2M NaCl. The amount of $^{125}I$-FGF bound to the high affinity receptor was determined by quantitating the amount of radioactivity in the cell lysate obtained with 0.1% Triton® X-100 in PBS, pH 8.4.

B. Mitogenesis assay

The effects of the peptides on mitogenesis was determined using Swiss 3T3 fibroblasts as described. Briefly, cells were plated at a concentration of 20,000 cells/well in 96 microwells and grown for two days in Hepes (25 mM) buffered DMEM containing 10% fetal calf serum and antibiotics. On the third day, the cells were washed twice with DMEM with no additives and the cells synchronized by a further incubation for two days in 0.5% fetal calf serum. At the time of assay, the test substances (basic FGF, EC-FGFR or both together) were added directly to the cells in 10 μL of DMEM supplemented with 0.1% BSA. Eighteen hours later, 1 μCi of $^3H$-thymidine was added to the cells, and 24 hours after the addition of the peptides, the media was aspirated, the cells washed with PBS and the proteins precipitated with 50% trichloroacetic acid. After three washes, the cells were solubilized overnight with 1 N NaOH and the amount of radioactivity incorporated into DNA was determined by scintillation counting.

C. *Cell* Proliferation Assays

The EC-FGF receptor was tested for its ability to inhibit basic FGF stimulated adrenal capillary endothelial (ACE) cell proliferation. Aliquots of receptor preparation were added to ACE cells and four days later, the cell number was established using a Coulter particle counter. For comparison purposes, 2 ng/ml of recombinant human basic FGF increased cell proliferation from 27,500±2,100 cells/well to 133,300±1,800 cells/well.

D. Receptor dependent tyrosine phosphorylated

Swiss 3T3 cells were treated at 37° C. for 5 minutes with no additives or with basic FGF (15 ng/mL), EC-FGF receptor (10 mg/mL) or basic FGF (15 ng/mL) and EC-FGF (10 mg/mL) added together. The cells were then harvested in a 2.5×Laemmli's buffer, the proteins separated on 8% polyacrylamide SDS-PAGE gels and the presence of tyrosine phosphorylated proteins examined by Western blotting with a specific anti-phosphotyrosine antibody.

The FGF binding properties of EC-FGF receptor was determined using a soluble binding assay (adapted from the assay described by Robinson et al., *J. Immunol. Meth.* (1990) 132:63–71). EC-FGF receptor, attached to concanavalin A coated plastic wells, was incubated with $^{125}I$-bFGF and increasing concentrations of bFGF. Scatchard analysis of $^{125}I$-FGF binding indicated a $K_d$ of less than 5 nM. An completely accurate $K_d$ determination was not possible due to the nonspecific binding of $^{125}I$-FGF. Several blocking agents included in the assays, such as BSA, gelatin and heparan sulfate, were ineffective at blocking the nonspecific binding of $^{125}I$-FGF at low concentrations of $^{125}I$-FGF.

The biological activity of the EC-FGF receptor was tested in several additional assay systems. First, the addition of EC-FGF receptor to endothelial cells in culture was shown to inhibit the proliferative effect of basic FGF. Because this cell type is known to synthesize basic FGF, it was suspected that the recombinant receptor might inhibit basal endothelial cell growth. As predicted, the expressed EC-FGF receptor can inhibit basal cell proliferation. Specificity of this effect was studied by incubating various cell types, that do not synthesize basic FGF, with the EC-FGF receptor. No effects were observed on BHK cells, A431 cells or on CHO cells. As expected, however, the addition of EC-FGF receptor to 3T3 cells inhibited the mitogenic response to basic FGF. Furthermore, it was observed that the EC-FGF receptor inhibited the growth of melanoma cells, a cell type previously shown to be dependent on the autocrine production of basic FGF.

To establish that the FGF/EC-FGF receptor complex did not recognize the basic FGF receptor, two experiments were performed. First, the addition of the EC-FGF receptor preparation to BHK cells during the radioreceptor assay prevented the binding of $^{125}I$-basic FGF to its receptor indicating that it binds basic FGF. The binding of $^{125}I$-basic FGF to its low affinity receptor was also inhibited. Secondly, basic FGF fails to activate the tyrosine phosphorylation of either its cell membrane receptor or the characteristic 90 kDa substrate identified by Coughlin et al., *J. Biol. Chem.* (1988) 263:988–993 when incubated in the presence of EC-FGF receptor.

Example 7

Cloning of UL115

A. pUL115

Plasmid pUL115 (ATCC Accession No. 69036) is a staging vector which contains the UL115 ORF. This plasmid was constructed as follows. Plasmid pRL103 (LaFemina and Hayward (1980) in *Animal Virus Genetics* (B. N. fields, R. Jaenisch, and C. F. Fox, Eds.) Vol. 28, pp. 39–55, Academic Press, New York) contains the CMV Towne strain HindIII C fragment cloned into HindIII of pBR322. Plasmid pRL103 was cut with restriction enzymes BamHI and BstEII and the 1053 bp fragment was isolated and purified from a 1% agarose gel. This 1053 bp fragment was cut with NarI and the 957 bp BamHI/NarI fragment containing the UL115 ORF was isolated. pBluescript II KS±vector (Stratagene) was digested with BamHI and AccI and the 2915 bp vector ligated to the 957 bp BamHI/NarI fragment, creating pUL115. This ligation destroyed the AccI and NarI sites and retained the BamHI site.

B. pVLUL115

Plasmid pVLUL115 is a baculovirus expression vector incorporating the UL115 ORF and was constructed as follows. The pUL115 staging vector was digested with BamHI and KpnI and the 981 bp fragment was gel isolated and purified. Plasmid pVL1392 (Webb and Summers, *J. Meth. Cell Mol. Biol.* (1990) 2:173–188) was cut with BamHI and PstI to obtain a 9249 bp vector fragment. The 981 bp and 9249 bp fragments were then ligated in the presence of Klenow to produce pVLUL115. The resulting ligation restored the BamHI site and destroyed the PstI and KpnI sites to produce a 10,230 bp plasmid.

C. pMCUL115

Plasmid pMCUL115 is a mammalian cell expression vector with the MCMV immediate early promoter used to drive transcription of the UL115 gene. This plasmid was constructed as follows. pUL115 was digested with Asp718 and XbaI to remove UL115 from the bluescript vector. Then the pmcsr vector was digested with Asp718 and XbaI. The Asp718-XbaI UL115 fragment was then ligated directly into the pmcsr Asp718-XbaI sites restoring both sites. The resulting plasmid was termed pMCUL115.

D. pMCUL115neo

Plasmid pMCUL115neo is a PSV2neo-based mammalian expression vector which contains the UL115 ORF whose expression is promoted by the MCMV immediate early promoter, along with the neomycin selectable marker. The plasmid was constructed as follows. pMCUL115 was digested with SfiI and XbaI, and a 2.3 kb fragment was isolated, gel purified, and Genecleaned. Vector pSV2neo (Southern and Berg, *J. Molec. and App. Gen.* (1982) 1:327–341) was digested with EcoRI and BamHI and a 4.5 kb fragment was gel purified, isolated and Genecleaned. Both the 4.5 kb vector and the 2.3 kb MCUL115 fragments were treated with Klenow to prepare for blunt end ligation.

The vector was phosphatased, phenol chloroform extracted and ethanol precipitated. Blunt end ligation of the 4.5 kb vector and the 2.3 kb MCMV-UL115 fragment resulted in pMCUL115neo.

Example 8

Coexpression of CMV gH and UL! 15 in a Recombinant Baculovirus Vector

Recombinant baculovirus vectors expressing full length (gH2) and C-terminally truncated gH (gH6), were generated as described in Examples 3 and 4, respectively. A recombinant baculovirus (rBV) vector expressing the gene product of the UL115 ORF was generated by cotransfection of wildtype baculovirus DNA with transfer vector pVLUL115 (Example 7B) as described in Examples 3 and 4. Recombinant baculovirus vector rBVgH6 expressing truncated gH was used in coinfection experiments with rBVUL115 in SF9 cells. Cells were infected or coinfected at a MOI of 1, labeled with [$^{35}$S]cysteine, and lysates and supernatants were examined for expression by radioimmunoprecipitation using murine monoclonal antibody (MAb) 14–4b (Urban et al., *J. Virol.* (1992) 66:1303–1311) which is a conformational dependent neutralizing antibody specific for CMV gH. The results showed that rBVUL115 and rBVgH6 expressed maximally at two days post infection (dpi), and that a prominant protein migrating at 32 kDa was precipitated or coprecipitated with gH by the monoclonal antibody. Western blot analysis of lysates or supernatants using rabbit antiserum raised against a peptide from UL115 reacted specifically with UL115 gene product. Accordingly, this evidenced the presence of a CMV gH/UL115 complex.

Example 9

Coexpression of CMV gH and UL115 in Mammalian Cells

Figure 8:
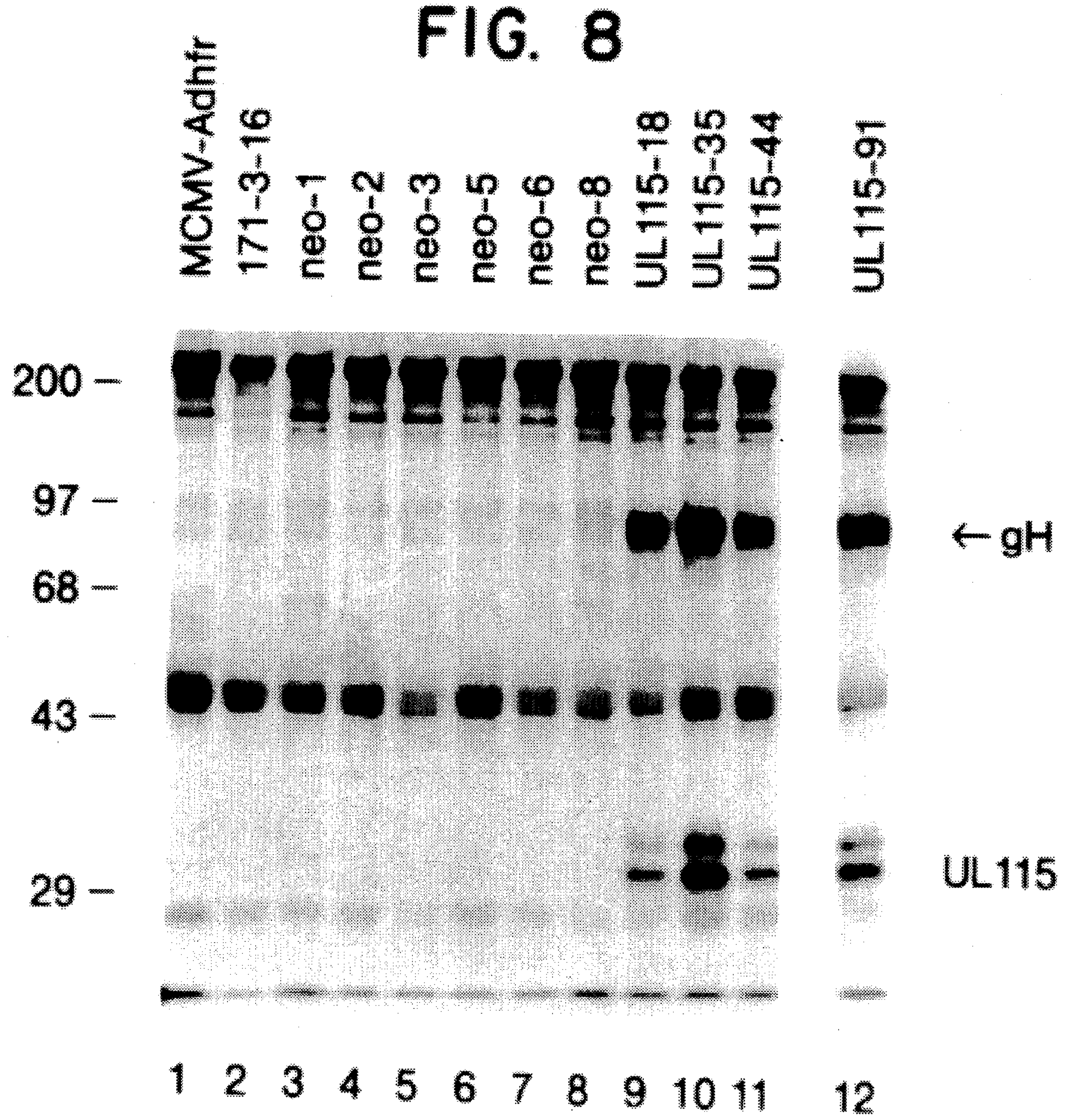
FIG. 8 is a representation of an autoradiogram showing that coexpression of the gene product of the UL115 open reading frame with gH results in secretion of gH. A stable gH expressing CHO cell line 171 was transfected with: (1) plasmid pFGFrtpaneo expressing truncated $FGF_r$ to generate cell line 171-3-16 (lane 2), (2) vector control plasmid pSV2neo to generate cell lines 171-neo-1, 171-neo-2, 171-neo-3, 171-neo-5, 171-neo-6, 171-neo-8 (lanes 3–8), and (3) plasmid pMCUL115neo expressing the gene product of the UL115 ORF from CMV strain Towne to generate cell line 171-UL115-18, 171-UL115-35, 171-UL115-44, and 171-UL115-91 (lanes 9–12). CHO cell line MCMV-Adhfr (lane 1) was generated by transfection of CHO cells with the mammalian cell expression vector pMCMVAdhfr (Spaete et al. *J. Virol.* (1990) 64:2922–2931) and represents a negative control. Cells were labeled with 230 μCi/ml [$^{35}$S]cysteine for 5 hours in DME lacking cysteine plus 10% dialyzed fetal calf serum. Conditioned media were immunoprecipitated with murine monoclonal antibody 14-4b specific for CMV gH (Urban et al., *J. Virol.* (1992) 66:1303–1311). The protein molecular mass standards are shown on the left of the autoradiogram in kilodaltons, and the mobility of gH and the UL115 precipitated products are indicated on the right.

Plasmid pMCUL115neo described in Example 7D was transfected into stable gH secreting cell line 171 (Example 2), or GRP2gH previously transfected with gH expression plasmid pMCGRP2gH, in order to generate new gH secreting cell lines. Plasmid pMCGRP2gH was generated by ligating a 2166 bp NotI/XbaI fragment encoding gH taken from pCMgH6 into NotI/XbaI digested mammalian cell expression vector pMCGRP2SR, a derivative of pMCMVAdhrf (Spaete et al. *J. Virol.* (1990) 64:2922–2931). Plasmid vector pSV2neo was transfected into cell lines 171 and GRP2gH as a control. Clones were selected for resistance to neomycin and 96 clones from each transfection series were picked and assayed by ELISA. Clones secreting the highest amounts of gH were expanded to 6-well plates and reassayed by ELISA. Selected cell lines were further assayed by radioimmunoprecipitation using MAb 14-4b (Urban et al., *J. Virol.* (1992) 66:1303–1311). As shown in FIG. 8, cell lines secreting gH at levels detectable by RIP are also those which express the gene product of the UL115 ORF. Additional characterization of the coprecipiated UL115/gH complex under nonreducing conditions revealed that UL115 and gH are linked by disulfide bonds.

Example 10

Coexpression of truncated CMV gH with the Soluble FGF Receptor

CHO cell line 171 described in Example 2 was transfected with plasmid pFGFrtpaneo#3 designed to express a soluble form of the $FGF_r$. Plasmid pFGFrtpaneo#3 was generated by ligating a 3 kbp SFiI/HindIII fragment from $pFGF_r$tpa, encoding the human CMV immediate early promoter, tpa leader and C-terminally truncated $FGF_r$ into EcoRI/BamHI digested pSV2neo (Southern and Berg, *J. Molec. and App. Gen.* (1982) 1:327–341). The fragments were treated with Klenow fragment to blunt the ends prior to ligation. Plasmid $pFGF_r$tpa was constructed by ligating a 1 kbp PCR generated NhoI/HindIII fragment encoding the C-terminally truncated $FGF_r$ into an NhoI/HindIII digested mammalian cell expression vector pCMV6a120 (Chapman et al., *Nuc. Acids Res.* (1991) 19:3979–3986). The fragment encoding the truncated $FGF_r$ was generated with the following primer pairs:

(SEQ. NO:19) 5' GGA TCC GCT AGC AGG CCG TCC CCG ACC TTG 3'

(SEQ. NO:20) 5' GGA TCC AAG CTT TTA CTC CAG GTA CAG GGG CGA 3'.

Plasmid PB5 flg5 was used as the template.

Transfected cells were selected for resistance to neomycin and resistant clones were picked and assayed for levels of gH secretion by ELISA. Cell line 171-3-16 is representative of one such selected cell line (FIG. 8, lane 2). Radioimmunoprecipitation of selected gH secreting cell lines revealed gH specific bands on autoradiographs after a five day exposure. However, growth of the cell lines at 30° C. prior to RIP resulted in increased secretion of gH with the consequence of being able to see a detectable band on autoradiographs in 24 hours after labeling the cells 4 hours in 250 μCi/ml [$^{35}$S]methionine. A coprecipitated 60 kDa molecule was shown to be C-terminally truncated $FGF_r$ by radioimmunoprecipitation using anti-$FGF_r$ antibodies and an $FGF_r$ competion assay, as described in Example 6A. Thus, secretion of gH is facilitated by coexpression of truncated $FGF_r$.

Example 11

Specificity of Receptor/Ligand Coexpression

As a test of the generality of receptor/ligand coexpression strategies, cell lines transfected with an expression plasmid encoding heparan sulfate proteoglycan were assayed for the effect on gH secretion. 159 clones selected to express heparan sulfate proteoglycan were compared by ELISA for levels of gH secretion with 60 vector control lines. There was no difference in levels of gH secretion from either population of selected clones, suggesting that there is specificity involved in successful coexpression strategies.

Thus, methods for increasing cell surface expression of proteins using escorts are described. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as convenience to those of skill in the art, and are not an admission that a deposit is required under 35 USC §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| pACgH6 (in *E. coli* HB101) | 7/27/90 | 68373 |
| pUL115 (in *E. coli* HB101) | 7/23/92 | 69036 |
| pCMAdgH6 (in *E. coli* HB101) | 7/23/92 | 69035 |

I claim:

1. A method for recombinantly producing an immunologically reactive truncated cytomegalovirus glycoprotein H wherein said truncated glycoprotein H lacks all or a portion of a transmembrane binding domain which is present in native human cytomegalovirus glycoprotein H, said method comprising (a) coexpressing in a host cell a first gene encoding said truncated glycoprotein H with a second gene encoding soluble fibroblast growth factor receptor, under conditions whereby said truncated glycoprotein H is secreted from said host cell; and (b) recovering said secreted glycoprotein H.

2. The method of claim 1 wherein from 10 to 22 amino acids are deleted from the C-terminus of the amino acid sequence of cytomegalovirus glycoprotein H.

3. The method of claim 1 wherein from 10 to 23 amino acids are deleted from the C-terminus of the amino acid sequence of cytomegalovirus glycoprotein H.

4. A method for recombinantly producing an immunologically reactive truncated cytomegalovirus glycoprotein H wherein said truncated glycoprotein H lacks all or a portion of a transmembrane binding domain which is present in native human cytomegalovirus glycoprotein H, said method comprising (a) coexpressing in a host cell a first gene encoding said truncated glycoprotein H with a second gene encoding a UL115 polypeptide, under conditions whereby said truncated glycoprotein H is secreted by said host cell; and (b) recovering said secreted glycoprotein H.

5. The method of claim 4 wherein from 10 to 22 amino acids are deleted from the C-terminus of the amino acid sequence of cytomegalovirus glycoprotein H.

6. The method of claim 4 wherein from 10 to 23 amino acids are deleted from the C-terminus of the amino acid sequence of cytomegalovirus glycoprotein H.

* * * * *